US011267795B2

United States Patent
Del Rio Gancedo et al.

(10) Patent No.: US 11,267,795 B2
(45) Date of Patent: Mar. 8, 2022

(54) CRYSTALLINE PPAR-DELTA AGONIST

(71) Applicant: Reneo Pharmaceuticals, Inc., San Diego, CA (US)

(72) Inventors: Susana Del Rio Gancedo, Cambridge (GB); Osama Suleiman, Cambridge (GB); Emma Sharp, Cambridge (GB); Cristina Balogh, Cambridge (GB); Rachael Lee, Billingham (GB); Julie Macrae, Sandwich (GB); Neil Feeder, Sandwich (GB)

(73) Assignee: RENEO PHARMACEUTICALS, INC., San Diego, CA (US)

(*) Notice: Subject to any disclaimer, the term of this patent is extended or adjusted under 35 U.S.C. 154(b) by 0 days.

(21) Appl. No.: 17/381,005

(22) Filed: Jul. 20, 2021

(65) Prior Publication Data

US 2022/0024888 A1 Jan. 27, 2022

Related U.S. Application Data

(60) Provisional application No. 63/118,431, filed on Nov. 25, 2020, provisional application No. 63/055,235, filed on Jul. 22, 2020.

(51) Int. Cl.

| *A61K 9/08* | (2006.01) |
| *C07D 295/096* | (2006.01) |
| *A61K 9/00* | (2006.01) |
| *A61K 9/20* | (2006.01) |
| *A61K 9/48* | (2006.01) |

(52) U.S. Cl.
CPC ........ *C07D 295/096* (2013.01); *A61K 9/0019* (2013.01); *A61K 9/0053* (2013.01); *A61K 9/08* (2013.01); *A61K 9/2054* (2013.01); *A61K 9/4825* (2013.01); *A61K 9/4866* (2013.01); *C07B 2200/13* (2013.01)

(58) Field of Classification Search
CPC .. C07B 2200/13; C07D 295/096; A61K 9/08; A61K 9/0053; A61K 9/4866; A61K 9/2054
USPC ...................................... 514/239.2
See application file for complete search history.

(56) References Cited

U.S. PATENT DOCUMENTS

| 4,148,915 A | 4/1979 | Thuillier et al. |
| 4,920,132 A | 4/1990 | Huang et al. |
| 5,324,743 A | 6/1994 | Dillard et al. |
| 5,773,469 A | 6/1998 | Kanojia et al. |
| 5,919,793 A | 7/1999 | Brown et al. |
| 6,448,293 B1 | 9/2002 | Andrews et al. |
| 6,525,094 B1 | 2/2003 | Zhang et al. |
| 6,555,577 B1 | 4/2003 | Mogensen et al. |
| 6,569,901 B2 | 5/2003 | Mogensen et al. |
| 6,630,504 B2 | 10/2003 | Andrews |
| 6,867,218 B2 | 3/2005 | Mogensen et al. |
| 6,869,967 B2 | 3/2005 | Jeppesen et al. |
| 6,869,975 B2 | 3/2005 | Abe et al. |
| 6,875,780 B2 | 4/2005 | Auerbach et al. |
| 6,972,294 B1 | 12/2005 | Murray et al. |
| 7,067,530 B2 | 6/2006 | Jeppesen et al. |
| 7,091,245 B2 | 8/2006 | Jeppesen et al. |
| 7,129,268 B2 | 10/2006 | Jeppesen et al. |
| 7,202,213 B2 | 4/2007 | Mogensen et al. |
| 7,220,877 B2 | 5/2007 | Sauerberg et al. |
| 7,709,528 B2 | 5/2010 | Jeppesen et al. |
| 7,943,613 B2 | 5/2011 | Sauerberg et al. |
| 8,362,016 B2 * | 1/2013 | Sauerberg ............ C07D 307/79 514/239.5 |
| 8,551,993 B2 | 10/2013 | Sauerberg et al. |
| 9,487,493 B2 | 11/2016 | Valcarce Lopez et al. |
| 9,663,481 B2 | 5/2017 | Sauerberg et al. |
| 9,669,288 B2 | 6/2017 | Pertgen |
| 9,855,274 B2 | 1/2018 | Sauerberg et al. |
| 9,968,613 B2 | 5/2018 | Valcarce Lopez et al. |
| 10,456,406 B2 | 10/2019 | Valcarce Lopez et al. |
| 10,471,066 B2 | 11/2019 | Sauerberg et al. |
| 10,947,180 B2 | 3/2021 | Sauerberg et al. |
| 2004/0024034 A1 | 2/2004 | Brooks et al. |
| 2005/0080115 A1 | 4/2005 | Jeppesen et al. |
| 2008/0114036 A1 | 5/2008 | Havranek et al. |
| 2009/0012171 A1 | 1/2009 | Polivka |
| 2009/0048257 A1 | 2/2009 | Sauerberg |
| 2009/0192162 A1 | 7/2009 | Ebdrup |
| 2010/0197950 A1 | 8/2010 | Rasmussen et al. |
| 2010/0210653 A1 | 8/2010 | Havranek et al. |
| 2011/0245244 A1* | 10/2011 | Sauerberg ............ A61K 31/495 514/233.5 |

FOREIGN PATENT DOCUMENTS

| WO | WO-0063153 A1 | 10/2000 |
| WO | WO-0155085 A1 | 8/2001 |

(Continued)

OTHER PUBLICATIONS

Keraliya et al, title: Dissolution Technologies, published Feb. 2010. (Year: 2010).*
Berge et al. Pharmaceutical Salts. Journal of Pharmaceutical Sciences 66(1):1-19 (Jan. 1977).
Berger et al. Novel Peroxisome Proliferator-activated Receptor (PPAR) gamma and PPAR delta Ligands Produce Distinct Biological Effects. J Biol Chem 274(1):6718-6725 (1999).
Berger et al. Physiological and Therapeutic Roles of Peroxisome Proliferator-Activated Receptors. Diabetes Technology & Therapeutics 4(2):163-174 (2002).
Byrn et al. Chapter II: Hydrates and Solvates. Solid-State Chemistry of Drugs, 2nd edition pp. 233-248 (1999).

(Continued)

*Primary Examiner* — Ali Soroush
(74) *Attorney, Agent, or Firm* — Wilson Sonsini Goodrich & Rosati

(57) ABSTRACT

Described herein is crystalline sodium (E)-2-(4-((3-(4-fluorophenyl)-3-(4-(3-morpholinoprop-1-yn-1-yl)phenyl)allyl)oxy)-2-methylphenoxy)acetate, uses of such crystalline material in the preparation of pharmaceutical compositions for the treatment of diseases or conditions that would benefit by administration with a PPARδ agonist compound.

16 Claims, 27 Drawing Sheets

(56) References Cited

FOREIGN PATENT DOCUMENTS

| | | |
|---|---|---|
| WO | WO-0155086 A1 | 8/2001 |
| WO | WO-0179150 A1 | 10/2001 |
| WO | WO-03011807 A1 | 2/2003 |
| WO | WO-03011814 A1 | 2/2003 |
| WO | WO-03033453 A1 | 4/2003 |
| WO | WO-2004022533 A1 | 3/2004 |
| WO | WO-2004037775 A1 | 5/2004 |
| WO | WO-2004037776 A2 | 5/2004 |
| WO | WO-2005105725 A1 | 11/2005 |
| WO | WO-2005105735 A1 | 11/2005 |
| WO | WO-2005105736 A1 | 11/2005 |
| WO | WO-2007003581 A1 | 1/2007 |
| WO | WO-2007071766 A2 | 6/2007 |
| WO | WO-2007101864 A2 | 9/2007 |
| WO | WO-2007141295 A1 | 12/2007 |
| WO | WO-2015035171 A1 | 3/2015 |

OTHER PUBLICATIONS

Caira. Crystalline Polymorphism of Organic Compounds. Topics in Current Chemistry. 198:163-208 (Jan. 1998).

Fan et al. PPARγ Promotes Running Endurance by Preserving Glucose. Cell Metab. 25:1186-1193.e4 (2017).

Giron. Applications of Thermal Analysis and Coupled Techniques in Pharmaceutical Industry. J Therm Anal Calorim 68:335-357 (2002).

Giron. Investigations of Polymorphism and Pseudo-polymorphism in Pharmaceuticals by Combined Thermoanalytical Techniques. J Therm Anal Calorim 64:37-60 (2001).

Guillory. Chapter 5: Generation of Polymorphs, Hydrates, Solvates, and Amorphous Solids. Polymorphism in Pharmaceutical Solids pp. 183-226 (Brittain, H.G., ed., 1999).

Kadayat et al. Targeting Peroxisome Proliferator-Activated Receptor Delta (PPARδ): A Medicinal Chemistry Perspective. J. Med. Chem. 63(18):10109-10134 (2020).

Kersten et al. Roles of PPARs in health and disease. Nature 405:421-424 (2000).

Liu et al. Identification of a Series of PPAR gamme/delta Dual Agonists via Solid-Phase Parallel Synthesis. Bioorg. Med. Chem. Lett. 11:2959-2962 (2001).

Luquet et al. Peroxisome proliferator-activated receptor delta controls muscle development and oxydative capability. FASEB J 17(13): 209-226 (2003).

Michalik et al. Peroxisone proliferator-activated receptors: three isotypes for a multitude of functions. Curr Opin Biotechnology 10:564-570 (1999).

Narkar et al. AMPK and PPAR-sigma agonists are exercise mimetics. Cell 134(3):405-415 (2008).

Rodriguez-Spong et al. General principles of pharmaceutical solid polymorphism: a supramolecular perspective. Adv Drug Deliv Rev 56:241-274 (2004).

Sauerberg et al. Identification and Synthesis of a Novel Selective Partial PPAR-delta Agonist with Full Efficacy on Lipid Metabolism In Vitro and In Vivo. J Med Chem 50:1495-1503 (2007).

Souillac et al. Characterization of Delivery Systems, Differential Scanning Calorimetry. Encyclopedia of Controlled Drug Delivery pp. 212-227 (John Wiley & Sons 1999).

Vamecq et al. Medical Significance of Peroxisome Proliferator-Activated Receptors The Lancet, 354:141-148 (1999).

Vippagunta et al. Crystalline Solids. Advanced Drug Delivery Reviews 48:3-26 (2001).

Wahli. Peroxisome Proliferator-Activated Receptors (PPARs): from metabolic control to epidermal wound healing. Swiss Med Weekly 132:83-91 (2002).

Wang et al. Regulation of Muscle Fiber Type and Running Endurance by PPAR-delta. PLoS Biol. 2:e294 (2004).

Wilson et al. The PPARs: From Orphan Receptors to Drug Discovery. J Med Chem 43(4):527-550 (2000).

PCT/US2021/042412 International Search Report and Written Opinion dated Nov. 10, 2021.

* cited by examiner

CRYSTALLINE PPAR-DELTA AGONIST

CROSS-REFERENCE TO RELATED APPLICATIONS

This application claims the benefit of U.S. Provisional Application No. 63/118,431, filed Nov. 25, 2020, and U.S. Provisional Application No. 63/055,235, filed Jul. 22, 2020, each of which is incorporated herein by reference in its entirety.

FIELD OF THE INVENTION

Described herein are crystalline forms of a peroxisome proliferator-activated receptor delta (PPARδ) agonist compound, as well as pharmaceutical compositions thereof, and methods of use thereof in the treatment of diseases or conditions that would benefit from treatment with a PPARS agonist compound.

BACKGROUND OF THE INVENTION

PPARδ, a member of the nuclear regulatory superfamily of ligand-activating transcriptional regulators, is expressed throughout the body. PPARS agonists induce genes related to fatty acid oxidation and mitochondrial biogenesis. PPARS also has anti-inflammatory properties.

SUMMARY OF THE INVENTION

The present disclosure relates to various solid state forms of the PPARS agonist sodium (E)-2-(4-((3-(4-fluorophenyl)-3-(4-(3-morpholinoprop-1-yn-1-yl)phenyl)allyl)oxy)-2-methylphenoxy)acetate. Such forms of sodium (E)-2-(4-((3-(4-fluorophenyl)-3-(4-(3-morpholinoprop-1-yn-1-yl)phenyl)allyl)oxy)-2-methylphenoxy)acetate are useful for modulating the activity PPARS in mammals that would benefit from such activity.

Described herein is crystalline sodium (E)-2-(4-((3-(4-fluorophenyl)-3-(4-(3-morpholinoprop-1-yn-1-yl)phenyl)allyl)oxy)-2-methylphenoxy)acetate (Compound II).

In some embodiments, Compound II is crystalline Form 1. In some embodiments, crystalline Form 1 is characterized as having:
  (a) an XRPD pattern substantially the same as shown in FIG. 1;
  (b) an XRPD pattern with peaks at about 2.8° 2-Theta, about 7.2° 2-Theta, about 13.4° 2-Theta, about 17.8° 2-Theta, about 19.7° 2-Theta, about 19.9° 2-Theta, and about 20.6° 2-Theta as measured using Cu Kα radiation;
  (c) a DSC thermogram substantially the same as shown in FIG. 2;
  (d) a DSC thermogram with an endotherm having onset at about 179.5° C. and peak at about 181.6° C.;
  (e) a TGA pattern substantially the same as shown in FIG. 3;
  (f) a TGA pattern with a 0.1% w/w loss from 25 to 60° C. and degradation onset at about 250° C.;
  (g) an FTIR spectroscopy pattern substantially the same as shown in FIG. 4;
  (h) an FTIR spectroscopy pattern with peaks at about 103 $cm^{-1}$, about 838 $cm^{-1}$, about 1220 $cm^{-1}$, about 1504 $cm^{-1}$, and about 1612 $cm^{-1}$;
  (i) a Raman spectroscopy pattern substantially the same as shown in FIG. 5;
  (j) a Raman spectroscopy pattern with peaks at about 103 $cm^{-1}$, about 126 $cm^{-1}$, about 810 $cm^{-1}$, about 1158 $cm^{-1}$, about 1238 $cm^{-1}$, about 1604 $cm^{-1}$, and about 1629 $cm^{-1}$;
  (k) unit cell parameters substantially equal to the following at 100 K:

| Crystal System | Monoclinic |
|---|---|
| Space Group | P2/c |
| a (Å) | 31.581(3) |
| b (Å) | 6.1180(4) |
| c (Å) | 27.2046(18) |
| α° | 90 |
| β° | 94.447(7) |
| γ° | 90 |
| V (Å$^3$) | 5240.4(7) |
| Z | 8 |
| Calculated Density (Mg/m$^3$) | 1.363 |
| Absorption coefficient (mm$^{-1}$) | 0.937 |
| F(000) | 2256 | or
  (l) combinations thereof.

In some embodiments, the crystalline Compound II is unsolvated.

In some embodiments, the crystalline Compound II is a solvate. In some embodiments, crystalline compound II is an acetone solvate, 1-propanol solvate, 2-methyltetrahydrofuran solvate, methyl isobutyl ketone solvate, 1,4-dioxane solvate, chloroform solvate, tetrahydrofuran solvate, or dichloromethane solvate.

In some embodiments, the crystalline Compound II is a hydrate. In some embodiments described herein, the crystalline hydrate is crystalline Form 2 of Compound II. In some embodiments, crystalline Form 2 of Compound II is characterized as having:
  (a) an XRPD pattern substantially the same as shown in FIG. 6;
  (b) an XRPD pattern with peaks at about 4.5 2-Theta, about 13.8° 2-Theta, about 17.6° 2-Theta, about 19.0° 2-Theta, about 19.6° 2-Theta, about 19.9° 2-Theta, about 20.5° 2-Theta, and about 23.0° 2-Theta as measured using Cu Kα radiation;
  (c) a DSC thermogram substantially the same as shown in FIG. 7;
  (d) a DSC thermogram with six endothermic events having:
    i. an onset at about 44.1° C. and a peak at about 72.4° C.;
    ii. a peak at about 92.4° C.;
    iii. an onset at about 107.0° C. and a peak at about 118.5° C.;
    iv. an onset at about 127.6° C. and a peak at about 130.0° C.;
    v. an onset at about 146.9° C. and a peak at about 149.9° C.; and
    vi. an onset at about 179.5° C. and a peak at about 181.1° C.;
  (e) a TGA pattern substantially the same as shown in FIG. 8;
  (f) a TGA pattern with a 17.2% w/w loss from 25 to 145° C., and degradation onset at about 275° C.;
  (g) reversible water uptake (~25% w/w) between 0 and 90% Relative Humidity (RH);
  (h) an unchanged XRPD after GVS analysis at 90% RH and 25° C.;

(i) an unchanged XRPD after storage at 97% RH and 25° C. over 7 days;
(j) an unchanged XRPD after storage at 75% RH and 40° C. over 7 days;
or
(k) combinations thereof.

In some embodiments, the crystalline Compound II is a 2-methyltetrahydrofuran solvate. In some embodiments described herein, the crystalline 2-methyltetrahydrofuran solvate is crystalline Form 3 of Compound II. In some embodiments, crystalline Form 3 of Compound II is characterized as having:
(a) an XRPD pattern substantially the same as shown in FIG. 9;
(b) a DSC thermogram substantially the same as shown in FIG. 10;
(c) a DSC thermogram with three endothermic events having:
  i. an onset at about 58.7° C. and a peak at about 73.2° C.;
  ii. an onset at about 114.5° C. and a peak at about 136.2° C.; and
  iii. an onset at about 172.5° C. and a peak at about 178.6° C.;
(d) a TGA pattern substantially the same as shown in FIG. 11;
(e) a TGA pattern with a 2.3% w/w loss from 25 to 82° C., a further 3.8% w/w loss from 82° C. to 155° C., and a degradation onset at about 275° C.;
(f) reversible water uptake (~9.0% w/w) between 0 and 90% Relative Humidity (RH);
(g) an XRPD that converts to Form 1 after GVS analysis at 90% RH and 25° C.;
(h) an XRPD that converts to Form 1 after storage at 75% RH and 40° C. for 7 days;
or
(i) combinations thereof.

In some embodiments, the crystalline Compound II is a tetrahydrofuran solvate. In some embodiments described herein, the crystalline tetrahydrofuran solvate is crystalline Form 4 of Compound II. In some embodiments, crystalline Form 4 of Compound II is characterized as having:
(a) an XRPD pattern substantially the same as shown in FIG. 12;
(b) an XRPD pattern with peaks at about 3.3° 2-Theta, about 6.7° 2-Theta, about 20.1° 2-Theta, and about 20.7° 2-Theta as measured using Cu Kα radiation;
(c) a DSC thermogram substantially the same as shown in FIG. 13;
(d) a DSC thermogram with two endothermic events having:
  i. an onset at about 111.7° C. and a peak at about 114.5° C. with a broad shoulder starting at about 70° C.; and
  ii. an onset at about 142.5° C. and a peak at about 147.2° C. with a broad shoulder starting at about 130.6° C.;
(e) a TGA pattern substantially the same as shown in FIG. 14;
(f) a TGA pattern with a 14.3% w/w loss from 25 to 175° C., and degradation onset at about 285° C.;
(g) reversible water uptake (~23% w/w) between 0 and 90% Relative Humidity (RH);
(h) an XRPD that converts to Form 2 after GVS analysis at 90% RH and 25° C.;
(i) an unchanged XRPD after heating to 110° C.;
(j) an XRPD that converts to Form 2 after storage at 97% RH and 25° C. over 7 days;
(k) an XRPD that converts to Form 1 after storage at 75% RH and 40° C. over 7 days;
or
(l) combinations thereof.

In some embodiments, the crystalline Compound II is an acetone solvate. In some embodiments described herein, the crystalline acetone solvate is crystalline Form 5 of Compound II.

In some embodiments, crystalline Form 5 of Compound II is characterized as having:
(a) an XRPD pattern substantially the same as shown in FIG. 15;
(b) an XRPD pattern with peaks at about 2.8 2-Theta, about 8.3° 2-Theta, about 8.7° 2-Theta, about 13.1° 2-Theta, about 19.4° 2-Theta, about 20.2° 2-Theta, about 21.3° 2-Theta, and about 24.6° 2-Theta as measured using Cu Kα radiation;
(c) a DSC thermogram substantially the same as shown in FIG. 16;
(d) a DSC thermogram with two endothermic events having:
  i. an onset at 75.8° C. and two peaks at about 85.8° C. and 97.2° C.; and
  ii. onset at 180.4° C. and a peak at 182.2;
(e) an FTIR spectroscopy pattern substantially the same as shown in FIG. 17; or
(f) an FTIR spectroscopy pattern with peaks at about 810 cm$^{-1}$, about 838 cm$^{-1}$, about 1220 cm$^{-1}$, about 1504 cm$^{-1}$, and about 1612 cm$^{-1}$;
or
(g) combinations thereof.

In some embodiments, crystalline Form 5 of Compound II is further characterized as having: an XRPD that converts to Form 1 after drying; an XRPD that converts to Form 1 after GVS analysis at 90% RH and 25° C.; or combinations thereof.

Also described herein, in some embodiments, is amorphous sodium (E)-2-(4-((3-(4-fluorophenyl)-3-(4-(3-morpholinoprop-1-yn-1-yl)phenyl)allyl)oxy)-2-methylphenoxy)acetate (Compound II). In some embodiments, amorphous Compound II is characterized as having:
(a) an XRPD pattern showing a lack of crystallinity;
(b) a DSC thermogram substantially the same as shown in FIG. 22;
(c) a DSC thermogram with:
  i. a broad endotherm with onset at 43.1° C. and peak at about 60.3° C.;
  ii. a broad exotherm with onset at 107.0° C. and peak at 112.9° C.; and
  iii. an endotherm with onset at 125.0° C. peak a 130.4° C.;
(d) a TGA pattern substantially the same as shown in FIG. 23;
(e) a TGA pattern with a 3.7% w/w loss from 25 to 150° C., and a degradation onset at about 260° C.;
(f) an unchanged XRPD after storage at ambient temperature over 24 hours, 48 hours, 7 days, or 10 days;
(g) an unchanged XRPD after storage at 75% RH and 40° C. over 10 days;
or
(h) combinations thereof.

Also described herein, in some embodiments, is a pharmaceutical composition comprising a crystalline form Compound II and at least one pharmaceutically acceptable excipient. In other embodiments, is a pharmaceutical composition comprising amorphous Compound II and at least one pharmaceutically acceptable excipient. In some embodiments, the pharmaceutical composition is formulated for administration to a mammal by oral administration. In some embodiments, the pharmaceutical composition is formulated for administration to a mammal by oral administration in the form of a tablet, a pill, a capsule, a suspension, or a solution. In some embodiments, the pharmaceutical composition is in the form of a solid form pharmaceutical composition. In some embodiments, the pharmaceutical composition is in the form of a tablet, a pill, or a capsule.

Also described herein is a process for the preparation of sodium (E)-2-(4-((3-(4-fluorophenyl)-3-(4-(3-morpholinoprop-1-yn-1-yl)phenyl)allyl)oxy)-2-methylphenoxy)acetate (Compound II) comprising treating (E)-2-(4-((3-(4-fluorophenyl)-3-(4-(3-morpholinoprop-1-yn-1-yl)phenyl)allyl) oxy)-2-methylphenoxy)acetic acid (Compound I), or the alkyl ester of Compound I, or a salt thereof, with a sodium hydroxide solution in the presence of a suitable solvent to provide Compound II. In some embodiments, the alkyl ester is a $C_1$-$C_6$ alkyl ester. In some embodiments, the suitable solvent is water, methanol, ethanol, tetrahydrofuran, ethyl acetate, acetone, acetonitrile, or a combination thereof. In some embodiments, the preparation of the Compound II comprises treating Compound I with a sodium hydroxide solution in the presence of a suitable solvent, wherein the suitable solvent is water, methanol, ethanol, tetrahydrofuran, ethyl acetate, acetone, acetonitrile, or a combination thereof. In some embodiments, the preparation of the Compound II comprises treating Compound I with a sodium hydroxide solution in the presence of a suitable solvent, wherein the suitable solvent is a combination of acetone and acetonitrile. In some embodiments, Compound II is Crystalline Form 1 as described herein.

Articles of manufacture, which include packaging material, a compound described herein, or a pharmaceutically acceptable salt thereof, within the packaging material, and a label that indicates that the compound or composition, or pharmaceutically acceptable salt, pharmaceutically active metabolite, pharmaceutically acceptable prodrug, or pharmaceutically acceptable solvate thereof, is used for modulating the activity of PPARδ, or for the treatment, prevention or amelioration of one or more symptoms of a disease or condition that would benefit from modulation of PPARδ activity, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

Figure 1:
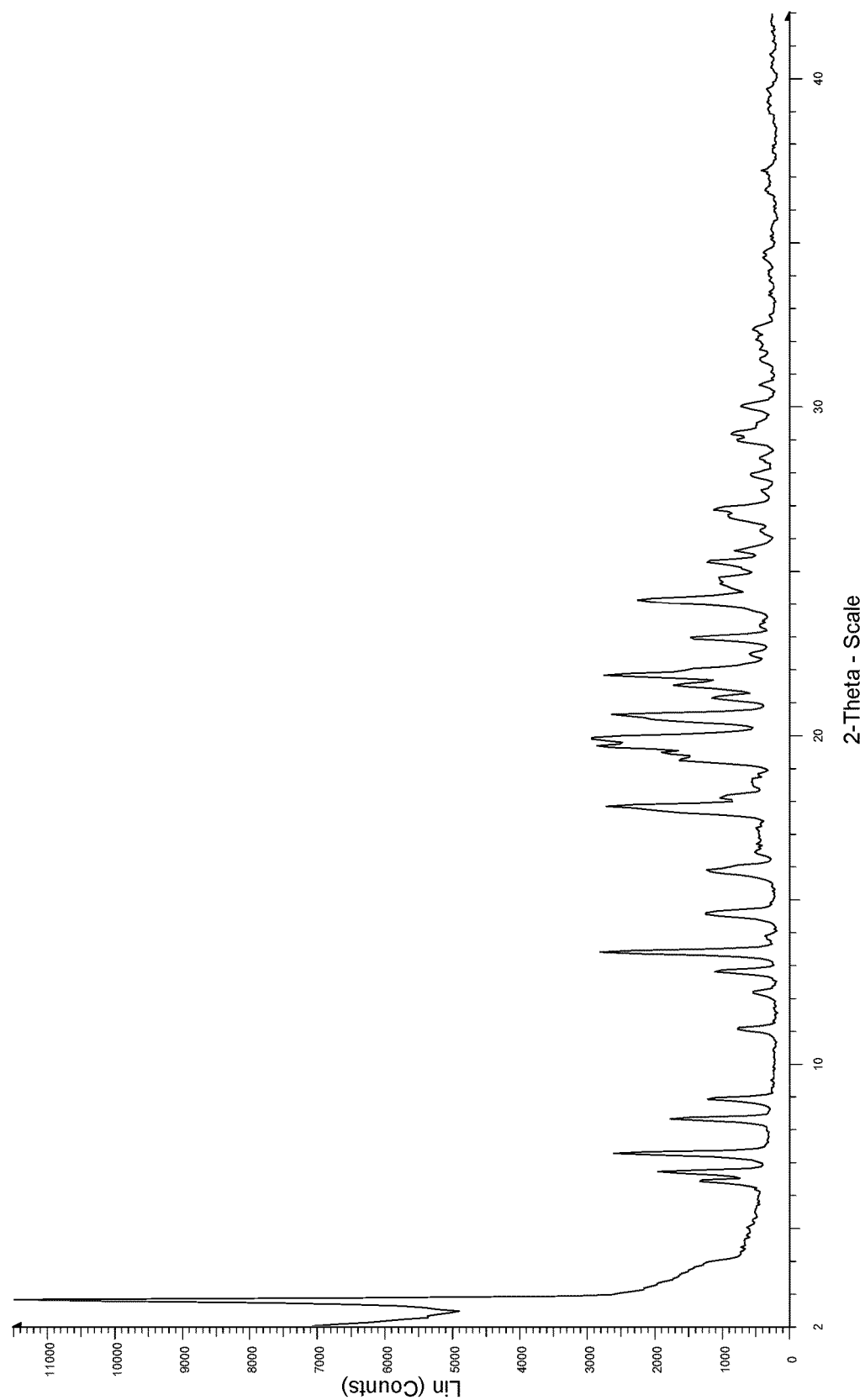
FIG. 1 illustrates a representative XRPD pattern for Form 1 of Compound II.

DETAILED DESCRIPTION OF THE INVENTION (E)-2-(4-((3-(4-Fluorophenyl)-3-(4-(3-morpholinoprop-1-yn-1-yl)phenyl)allyl)oxy)-2-methylphenoxy)acetic acid (Compound I) is a potent, selective and orally bioavailable PPARδ agonist. The PPARs are members of the nuclear receptor superfamily, which are ligand-modulated transcription factors that regulate gene expression of many cellular processes. The three PPARs, α, γ, and δ, are activated by lipids and are targets for current drug therapies for components of the metabolic syndrome. PPARα, a target for the fibrate class of triglyceride (TG)-lowering drugs, is primarily expressed in liver, where it upregulates genes involved in lipid oxidation in the fasted state. PPARγ is highly expressed in adipose tissue and regulates adipogenesis and insulin sensitivity. Pioglitazone is a drug from the thiazolidinedione class that increase insulin sensitivity through activating PPARγ. Compound I exhibits a significantly greater selectivity for PPARδ over PPARα and PPARγ (by 100-fold and 400-fold, respectively), and acts as a full agonist of PPARδ and only a partial agonist for both PPARα and PPARγ.

PPARδ controls genes involved in cellular metabolic processes such as glucose homeostasis, fatty acid synthesis and storage, and fatty acid mobilization and metabolism. PPARδ is expressed in several metabolically active tissues including liver, muscle, and fat. It is the most abundant PPAR isoform in skeletal muscle and has a higher expression in oxidative type I muscle fibers compared with glycolytic type II muscle fibers. A number of different physiological and pathological factors are reported to influence skeletal muscle PPARδ content. Both short term exercise and endurance training lead to increased PPARδ expression in human and rodent skeletal muscle. There is currently no marketed drug available targeting PPARδ.

Both genetic overexpression and pharmacological activation of PPARδ in mouse muscles results in increased number of fibers with high mitochondrial content and improves fatty acid oxidation. Overexpression of a constitutively active PPARδ (VP16-PPARδ) in skeletal muscles of transgenic mice pre-programs an increase in oxidative muscle fibers, enhancing running endurance in untrained adult mice (Wang, Y.-X., et al. (2004). Regulation of muscle fiber type and running endurance by PPARδ. *PLoS Biol.* 2, e294). The PPARδ agonist, GW1516, in combination with exercise (for 4 weeks) synergistically induced fatigue-resistant oxidative muscle fibers and mitochondrial biogenesis in mice, and therefore enhanced physical performance (Narkar, V. A., et al. (2008). AMPK and PPARδ agonists are exercise mimetics. *Cell* 134, 405-415). When mice were treated with GW1516 for a longer time (8 weeks compared to 4 weeks) a clear shift in energy substrate usage from glucose to fatty acid oxidation to a level similar to exercise training was observed, indicative of increased fatty acid metabolism (Fan, W., et al. (2017). PPARS Promotes Running Endurance by Preserving Glucose. *Cell Metab.* 25, 1186-1193.e4).

Compound I

Compound I is a PPARS agonist that is useful in the methods of treatment described herein. In human cell lines expressing the three peroxisome proliferator-activated receptor (PPAR) isotypes, Compound I is a potent (EC50<100 nM) and selective human PPARS agonist (PPARα (EC50>10 μM) and PPARγ (EC50>10 μM)). Compound I is a full PPARS agonist. Additionally, exposure human cells expressing the nuclear receptors RXR, FXR, LXRα or LXRβ has not resulted in activation of these nuclear receptors.

In vivo experiments demonstrated that Compound I treatment altered the expression patterns of several well-known PPARS regulated genes in pathways involved in the beta-oxidation of long chain fatty acids (CPT1b) and mitochondrial biogenesis (PGC-1α) in mice muscle. In rat muscle, Compound I treatment increased the expression of a known PPAR regulated target gene, Angiopoietin-like 4 (ANGPTL4).

The preparation and uses of Compound I have been previously described (see, WO 2007/071766, U.S. Pat. Nos. 7,943,613, 8,362,016, 8,551,993, 9,663,481, 9,855,274, WO 2015/035171, U.S. Pat. Nos. 9,487,493, 9,968,613, each of which is incorporated by reference in its entirety).

Compound I refers to (E)-2-(4-((3-(4-fluorophenyl)-3-(4-(3-morpholinoprop-1-yn-1-yl)phenyl)allyl)oxy)-2-methylphenoxy)acetic acid, which has the chemical structure shown below.

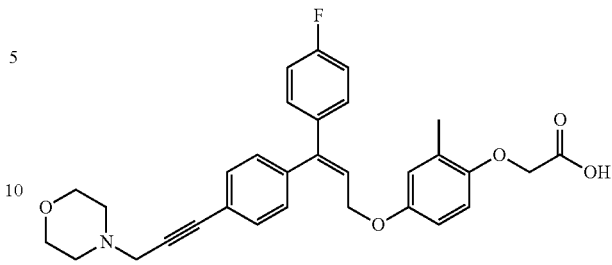

Compound I

In some embodiments, Compound I exists in a zwitterionic form.

Compound II refers to sodium (E)-2-(4-((3-(4-fluorophenyl)-3-(4-(3-morpholinoprop-1-yn-1-yl)phenyl)allyl)oxy)-2-methylphenoxy)acetate, which has the chemical structure shown below.

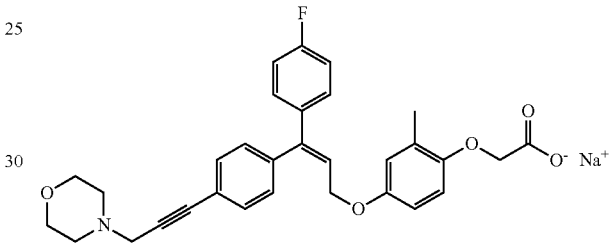

Compound II

In some embodiments, Compound II is amorphous.

As used herein, the term "amorphous" or "amorphous solid form" refers to a solid form lacking crystallinity.

In some embodiments, Compound II is crystalline.

In some embodiments, crystallinity of a solid form is determined by methods known in the art. In some embodiments, crystallinity of a solid form is determined by X-Ray Powder Diffraction (XRPD). In some embodiments, crystallinity of a solid form is determined by solid state NMR.

Amorphous Compound II

Figure 22:
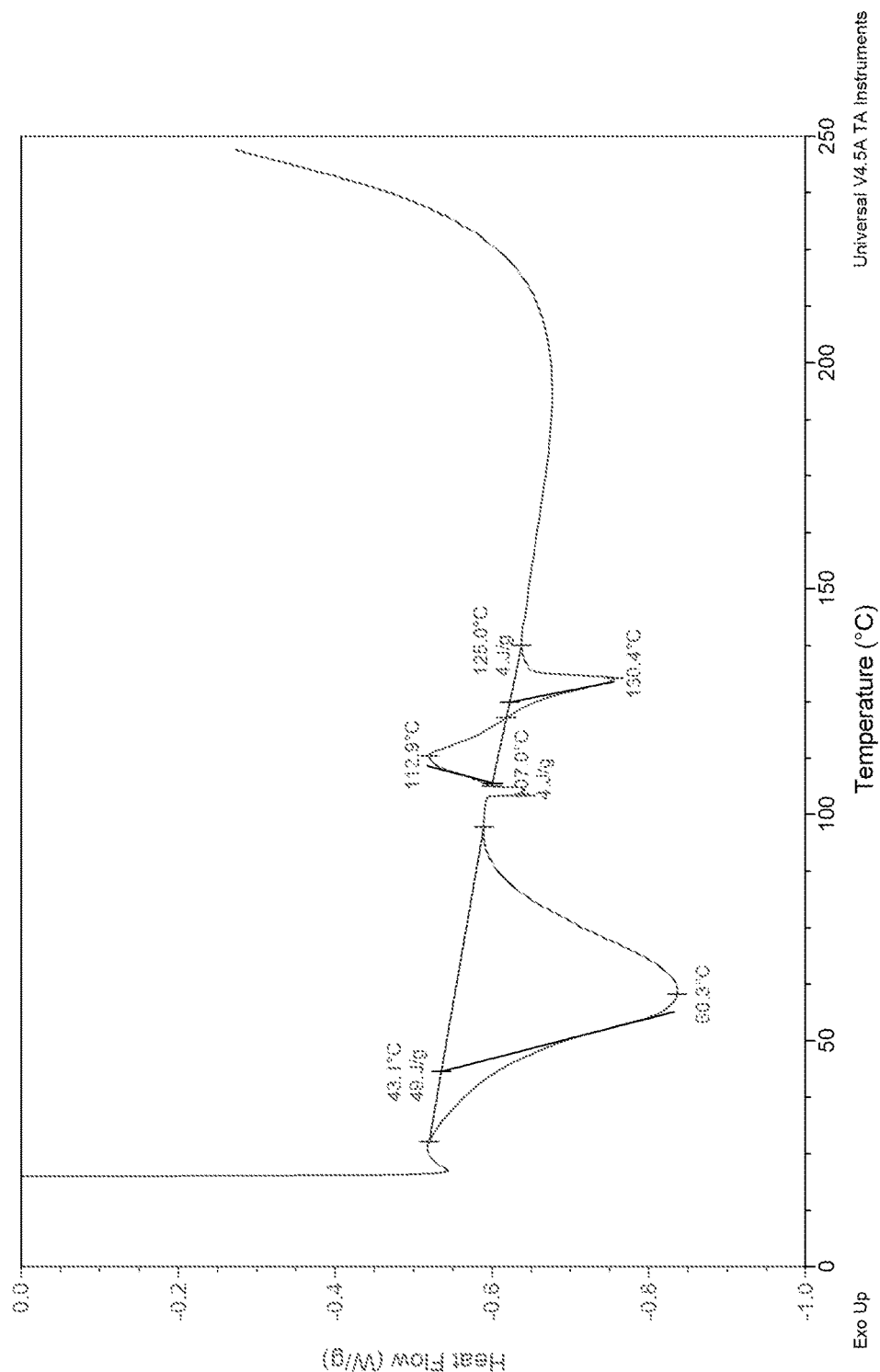
FIG. 22 illustrates a representative DSC thermogram for amorphous Compound II.
Figure 23:
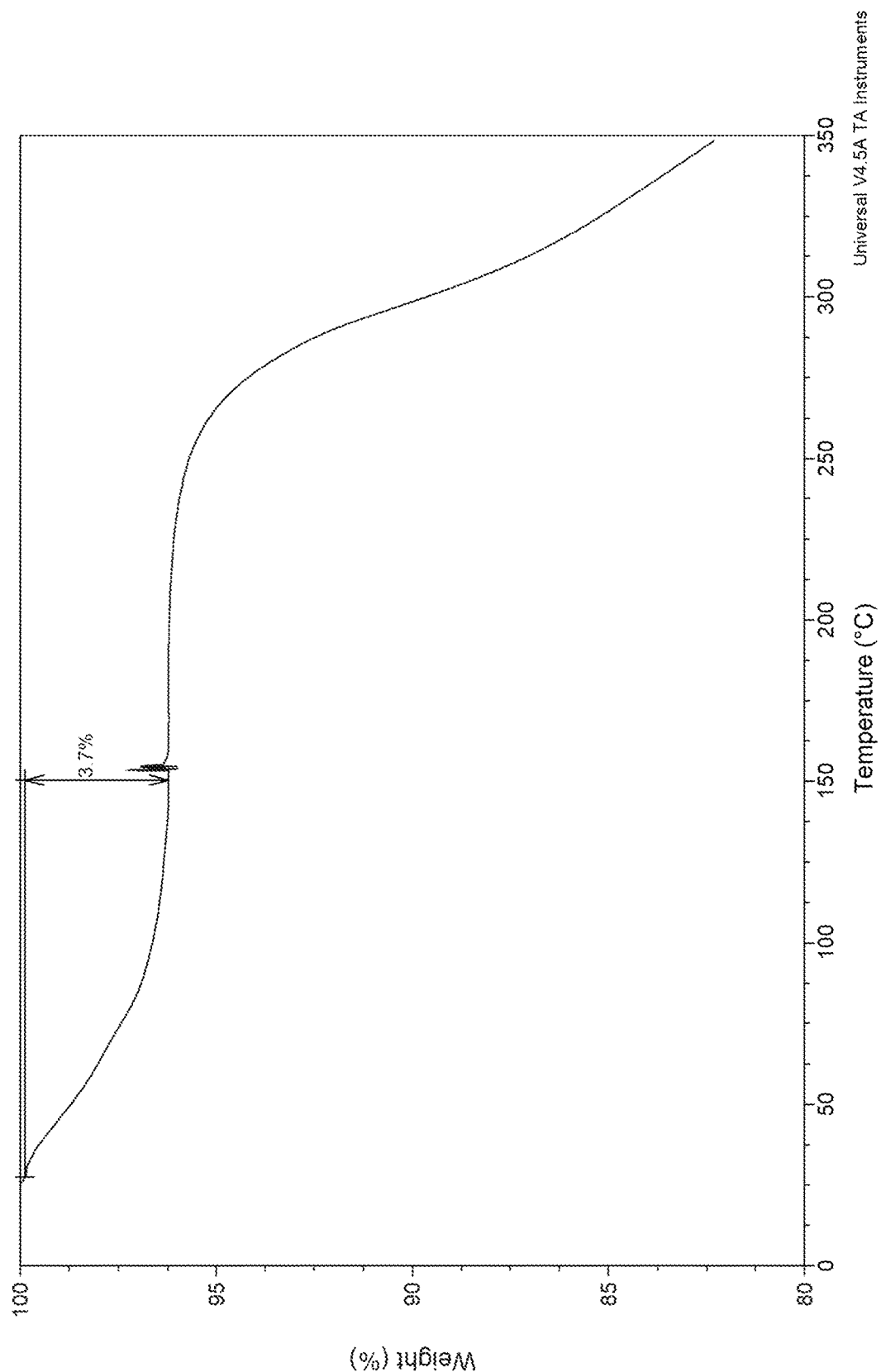
FIG. 23 illustrates a representative TGA thermogram for amorphous Compound II.

Provided herein is the amorphous Compound II. Some embodiments provide a composition comprising amorphous Compound II. In some embodiments, amorphous Compound II has one of the following properties:

a) an XRPD pattern showing a lack of crystallinity;
b) a DSC thermogram substantially the same as shown in FIG. 22;
c) a DSC thermogram with:
   i. a broad endotherm with onset at 43.1° C. and peak at about 60.3° C.;
   ii. a broad exotherm with onset at 107.0° C. and peak at 112.9° C.; and
   iii. an endotherm with onset at 125.0° C. peak a 130.4° C.;
d) a TGA pattern substantially the same as shown in FIG. 23;
e) a TGA pattern with a 3.7% w/w loss from 25 to 150° C., and a degradation onset at about 260° C.;
f) an unchanged XRPD after storage at ambient temperature over 24 hours, 48 hours, 7 days, or 10 days;

g) an unchanged XRPD after storage at 75% RH and 40° C. over 10 days;
or
h) combinations thereof.

Figure 21:
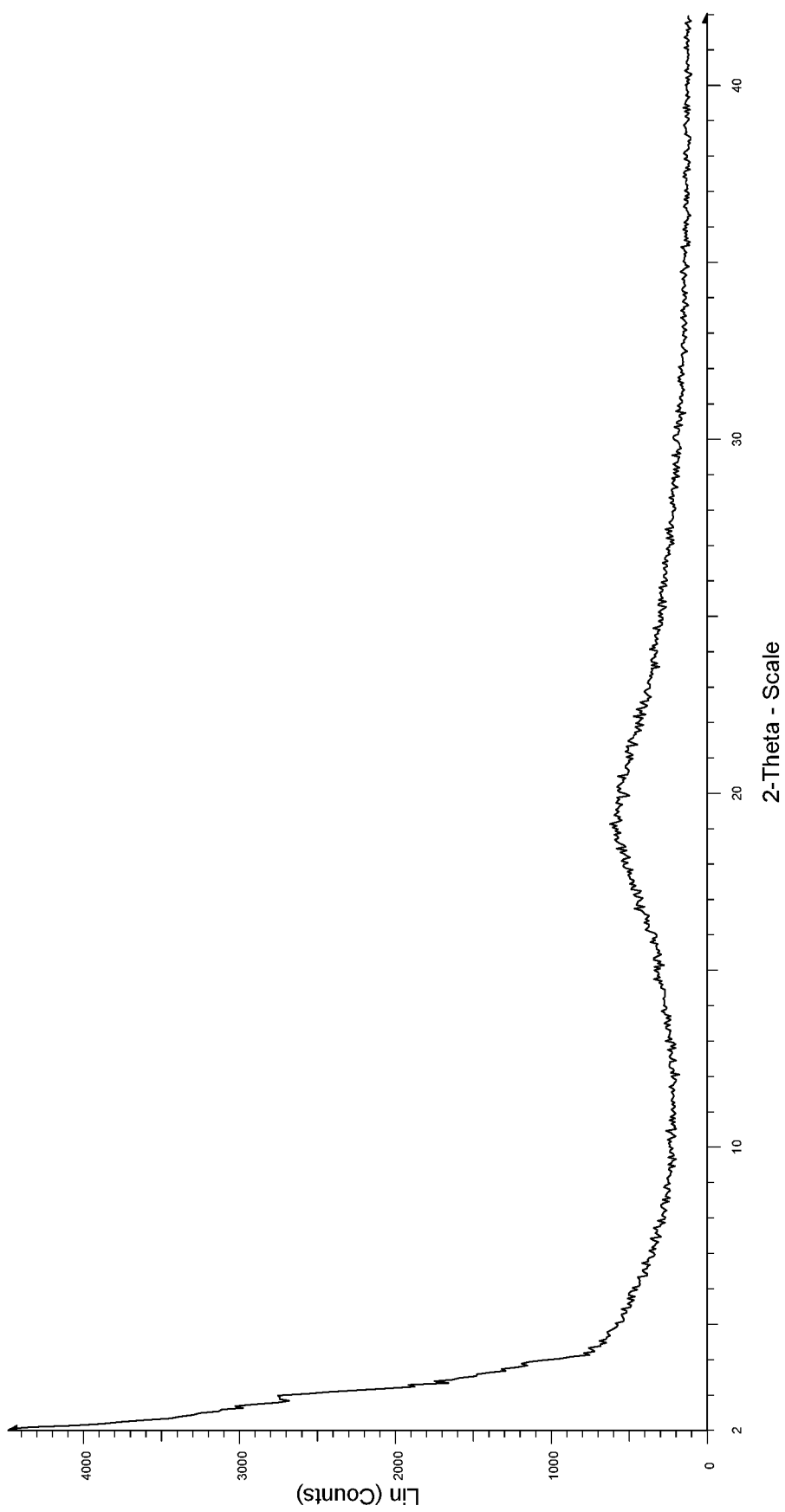
FIG. 21 illustrates a representative XRPD pattern for amorphous Compound II.

In some embodiments, amorphous Compound II has an XRPD pattern showing a lack of crystallinity. In some embodiments, amorphous Compound II has an XRPD pattern substantially the same as shown in FIG. 21. In some embodiments, amorphous Compound II has a DSC thermogram substantially the same as shown in FIG. 22. In some embodiments, amorphous Compound II has a DSC thermogram with: a broad endotherm with onset at 43.1° C. and peak at about 60.3° C.; a broad exotherm with onset at 107.0° C. and peak at 112.9° C.; and an endotherm with onset at 125.0° C. peak a 130.4° C. In some embodiments, amorphous Compound II has a TGA pattern substantially the same as shown in FIG. 23. In some embodiments, amorphous Compound II has a TGA pattern with a 3.7% w/w loss from 25 to 150° C., and a degradation onset at about 260° C. In some embodiments, amorphous Compound II has an unchanged XRPD after storage at ambient temperature over 24 hours, 48 hours, 7 days, or 10 days. In some embodiments, amorphous Compound II exhibits an unchanged XRPD after the GVS analysis at 75% RH and 40° C. over 10 days.

In some embodiments, amorphous Compound II is substantially free of impurities. In some embodiments, amorphous Compound II is at least about 90% pure. In some embodiments, amorphous Compound II is at least about 95%, about 96%, about 97%, about 98%, or about 99% pure. In some embodiments, amorphous Compound II is at least about 95% pure. In some embodiments, amorphous Compound II is at least about 96% pure. In some embodiments, amorphous Compound II is at least about 97% pure. In some embodiments, amorphous Compound II is at least about 98% pure. In some embodiments, amorphous Compound II is at least about 99% pure. In some embodiments, amorphous Compound II is at least about 99.1%, about 99.2%, about 99.3%, about 99.4%, about 99.5%, about 99.6%, about 99.7%, about 99.8%, about 99.9%, or about 100% pure.

Crystalline Compound II

Also provided herein is crystalline Compound II.

In some embodiments, the crystalline Compound II is unsolvated.

In some embodiments, the crystalline Compound II is solvated. In some embodiments, the crystalline Compound II is an acetone solvate, 1-propanol solvate, 2-methyltetrahydrofuran solvate, methyl isobutyl ketone solvate, 1,4-dioxane solvate, chloroform solvate, tetrahydrofuran solvate, or dichloromethane solvate. In some embodiments, the crystalline Compound II is an acetone solvate.

In some embodiments, the crystalline Compound II is a 2-methyltetrahydrofuran solvate. In some embodiments, the crystalline Compound II is a tetrahydrofuran solvate.

In some embodiments, the crystalline Compound II is a hydrate.

In some embodiments, amorphous Compound II is substantially free of impurities. In some embodiments, amorphous Compound II is at least about 90% pure. In some embodiments, amorphous Compound II is at least about 95%, about 96%, about 97%, about 98%, or about 99% pure. In some embodiments, amorphous Compound II is at least about 95% pure. In some embodiments, amorphous Compound II is at least about 96% pure. In some embodiments, amorphous Compound II is at least about 97% pure. In some embodiments, amorphous Compound II is at least about 98% pure. In some embodiments, amorphous Compound II is at least about 99% pure. In some embodiments, amorphous Compound II is at least about 99.1%, about 99.2%, about 99.3%, about 99.4%, about 99.5%, about 99.6%, about 99.7%, about 99.8%, about 99.9%, or about 100% pure.

Crystalline Form 1 of Compound II

In some embodiments, the crystalline Compound II is crystalline Form 1 of Compound II.

Figure 2:
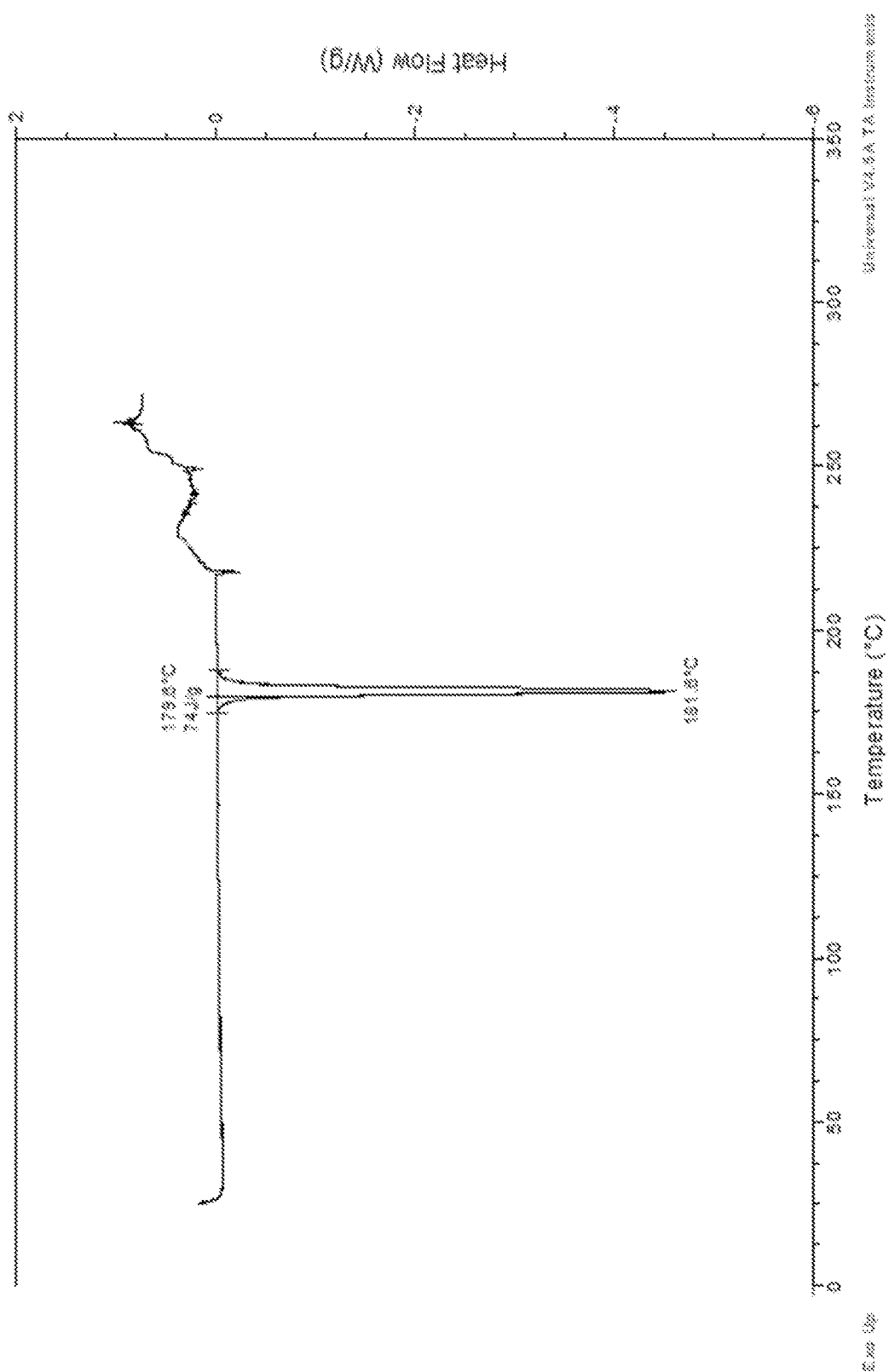
FIG. 2 illustrates a representative DSC thermogram for Form 1 of Compound II.
Figure 3:
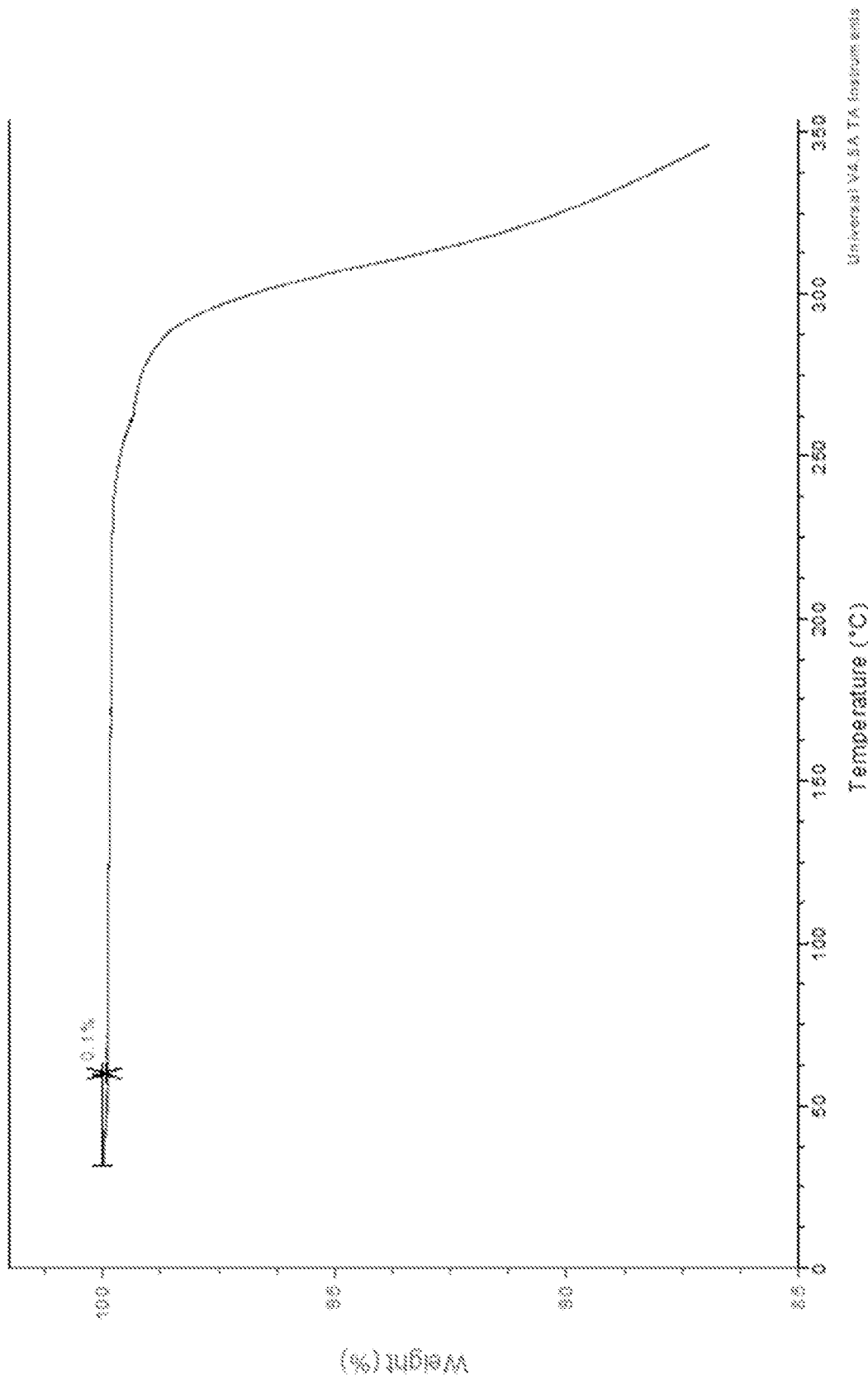
FIG. 3 illustrates a representative TGA thermogram for Form 1 of Compound II.
Figure 4:
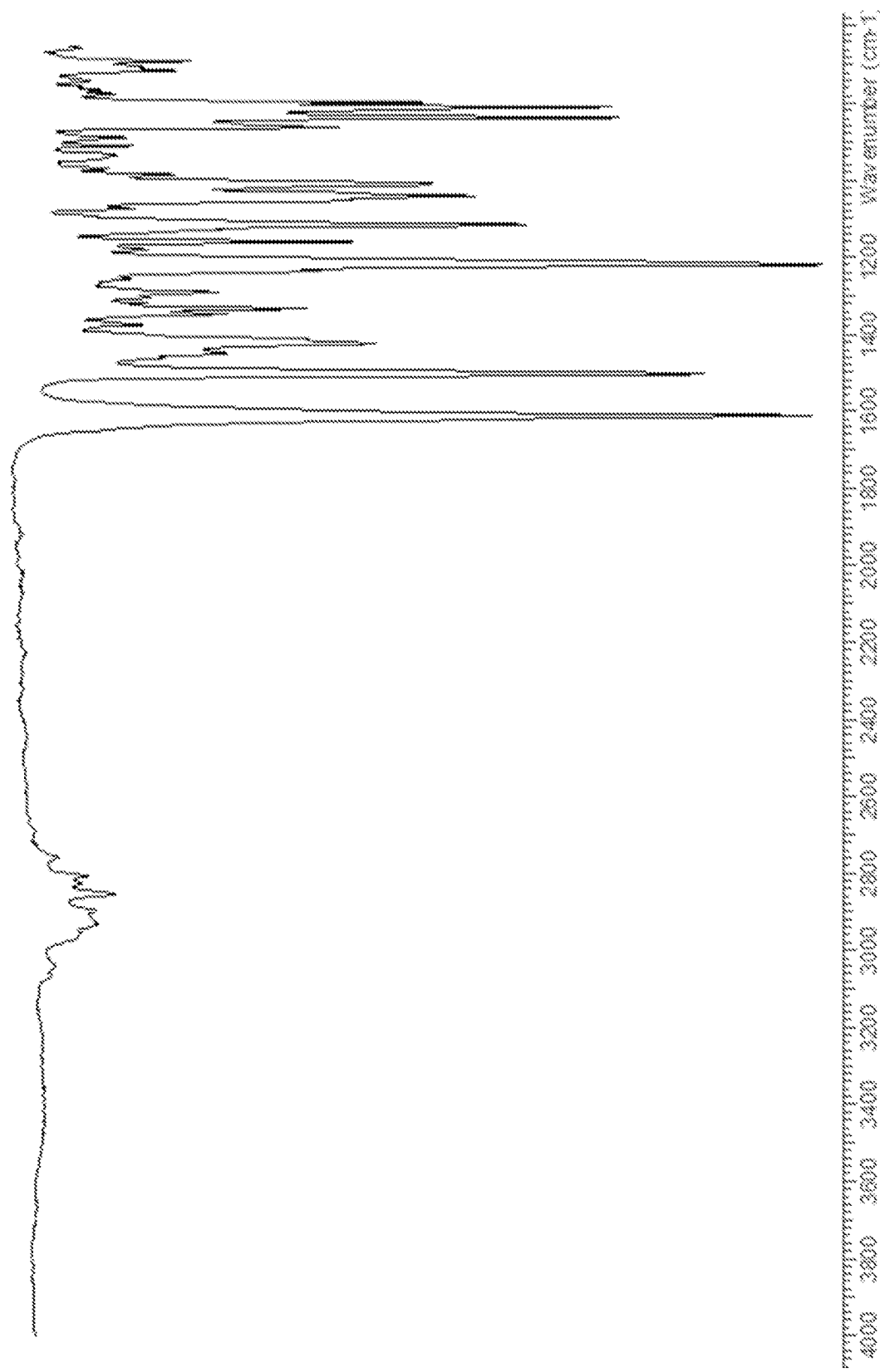
FIG. 4 illustrates a representative FTIR spectrum for Form 1 of Compound II.
Figure 5:
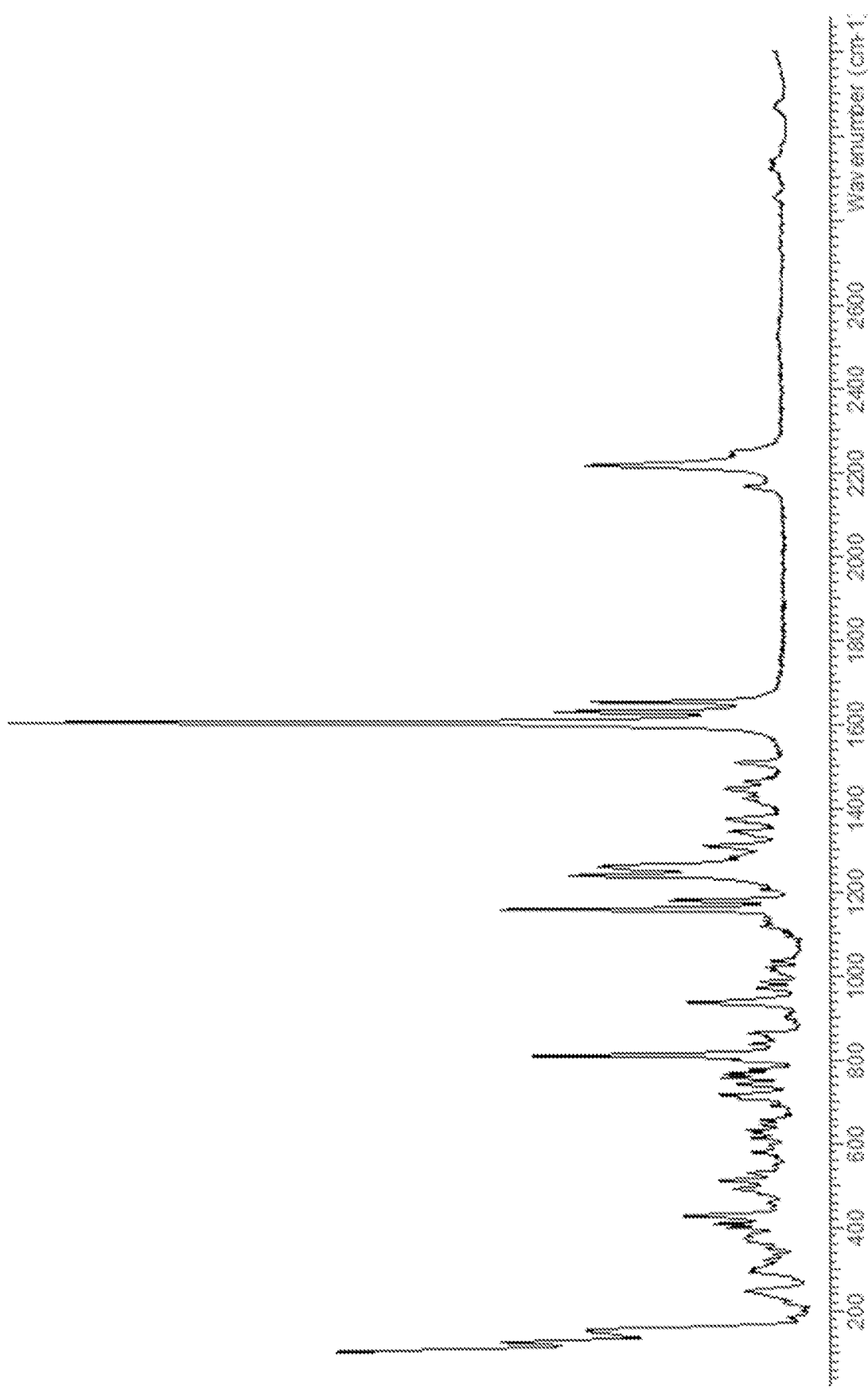
FIG. 5 illustrates a representative Raman spectrum for Form 1 of Compound II.

In some embodiments, described herein is a composition comprising crystalline Form 1 of Compound II. In some embodiments, crystalline Form 1 of Compound II is characterized as having:

a) an XRPD pattern substantially the same as shown in FIG. 1;
b) an XRPD pattern with peaks at about 2.8° 2-Theta, about 7.2° 2-Theta, about 13.4° 2-Theta, about 17.8° 2-Theta, about 19.7° 2-Theta, about 19.9° 2-Theta, and about 20.6° 2-Theta as measured using Cu Kα radiation;
c) a DSC thermogram substantially the same as shown in FIG. 2;
d) a DSC thermogram with an endotherm having onset at about 179.5° C. and peak at about 181.6° C.;
e) a TGA pattern substantially the same as shown in FIG. 3;
f) a TGA pattern with a 0.1% w/w loss from 25 to 60° C. and degradation onset at about 250° C.;
g) an FTIR spectroscopy pattern substantially the same as shown in FIG. 4;
h) an FTIR spectroscopy pattern with peaks at about 103 $cm^{-1}$, about 838 $cm^{-1}$, about 1220 $cm^{-1}$, about 1504 $cm^{-1}$, and about 1612 $cm^{-1}$;
i) a Raman spectroscopy pattern substantially the same as shown in FIG. 5;
j) a Raman spectroscopy pattern with peaks at about 103 $cm^{-1}$, about 126 $cm^{-1}$, about 810 $cm^{-1}$, about 1158 $cm^{-1}$, about 1238 $cm^{-1}$, about 1604 $cm^{-1}$, and about 1629 $cm^{-1}$;
k) unit cell parameters substantially equal to the following at 100 K:

| Crystal System | Monoclinic |
|---|---|
| Space Group | P2/c |
| a (Å) | 31.581(3) |
| b (Å) | 6.1180(4) |
| c (Å) | 27.2046(18) |
| α° | 90 |
| β° | 94.447(7) |
| γ° | 90 |
| V (Å³) | 5240.4(7) |
| Z | 8 |
| Calculated Density (Mg/m³) | 1.363 |
| Absorption coefficient ($mm^{-1}$) | 0.937 |
| F(000) | 2256 | or
l) combinations thereof.

In some embodiments, crystalline Form 1 of Compound II has an XRPD pattern substantially the same as shown in FIG. 1. In some embodiments, crystalline Form 1 of Compound II has an XRPD pattern with peaks at about 2.8° 2-Theta, about 7.2° 2-Theta, about 13.4° 2-Theta, about 17.8° 2-Theta, about 19.7° 2-Theta, about 19.9° 2-Theta, and about 20.6° 2-Theta as measured using Cu Kα radiation. In some embodiments, crystalline Form 1 of Compound II has a DSC thermogram substantially the same as shown in FIG. 2. In some embodiments, crystalline Form 1 of Compound II has a DSC thermogram with an endotherm having onset at about 179.5° C. and peak at about 181.6° C. In some embodiments, crystalline Form 1 of Compound II has a TGA pattern substantially the same as shown in FIG. 3. In some embodiments, crystalline Form 1 of Compound II has a TGA pattern with a 0.1% w/w loss from 25 to 60° C. and degradation onset at about 250° C. In some embodiments, crystalline Form 1 of Compound II has an FTIR spectroscopy pattern substantially the same as shown in FIG. 4. In some embodiments, crystalline Form 1 of Compound II has an FTIR spectroscopy pattern with peaks at about 103 cm$^{-1}$, about 838 cm$^{-1}$, about 1220 cm$^{-1}$, about 1504 cm$^{-1}$, and about 1612 cm$^{-1}$. In some embodiments, crystalline Form 1 of Compound II has a Raman spectroscopy pattern substantially the same as shown in FIG. 5. In some embodiments, crystalline Form 1 of Compound II has a Raman spectroscopy pattern with peaks at about 103 cm$^{-1}$, about 126 cm$^{-1}$, about 810 cm$^{-1}$, about 1158 cm$^{-1}$, about 1238 cm$^{-1}$, about 1604 cm$^{-1}$, and about 1629 cm$^{-1}$. In some embodiments, crystalline Form 1 of Compound II has a reversible water uptake (~13.0% w/w) between 0 and 90% Relative Humidity (RH).

In some embodiments, crystalline Form 1 of Compound II has unit cell parameters substantially equal to the following at 100 K:

| Crystal System | Monoclinic |
|---|---|
| Space Group | P2/c |
| a (Å) | 31.581(3) |
| b (Å) | 6.1180(4) |
| c (Å) | 27.2046(18) |
| α° | 90 |
| β° | 94.447(7) |
| γ° | 90 |
| V (Å$^3$) | 5240.4(7) |
| Z | 8 |
| Calculated Density (Mg/m$^3$) | 1.363 |
| Absorption coefficient (mm$^{-1}$) | 0.937 |
| F(000) | 2256 |

In some embodiments, crystalline Form 1 of Compound II has an XRPD pattern reflection at about 2.8° 2-Theta as measured using Cu Kα radiation. In some embodiments, crystalline Form 1 is further characterized by XRPD pattern reflections at about 7.2° 2-Theta, about 13.4° 2-Theta, about 17.8° 2-Theta, about 19.7° 2-Theta, about 19.9° 2-Theta, and about 20.6° 2-Theta. In some embodiments, crystalline Form 1 is further characterized by at least one XRPD pattern reflection selected from about 7.2° 2-Theta, about 13.4° 2-Theta, about 17.8° 2-Theta, about 19.7° 2-Theta, about 19.9° 2-Theta, and about 20.6° 2-Theta. In some embodiments, crystalline Form 1 is further characterized by at least two XRPD pattern reflections selected from about 7.2° 2-Theta, about 13.4° 2-Theta, about 17.8° 2-Theta, about 19.7° 2-Theta, about 19.9° 2-Theta, and about 20.6° 2-Theta.

In some embodiments, crystalline Form 1 is further characterized by at least three XRPD pattern reflections selected from about 7.2° 2-Theta, about 13.4° 2-Theta, about 17.8° 2-Theta, about 19.7° 2-Theta, about 19.9° 2-Theta, and about 20.6° 2-Theta.

Crystalline Form 2 of Compound II

Figure 6:
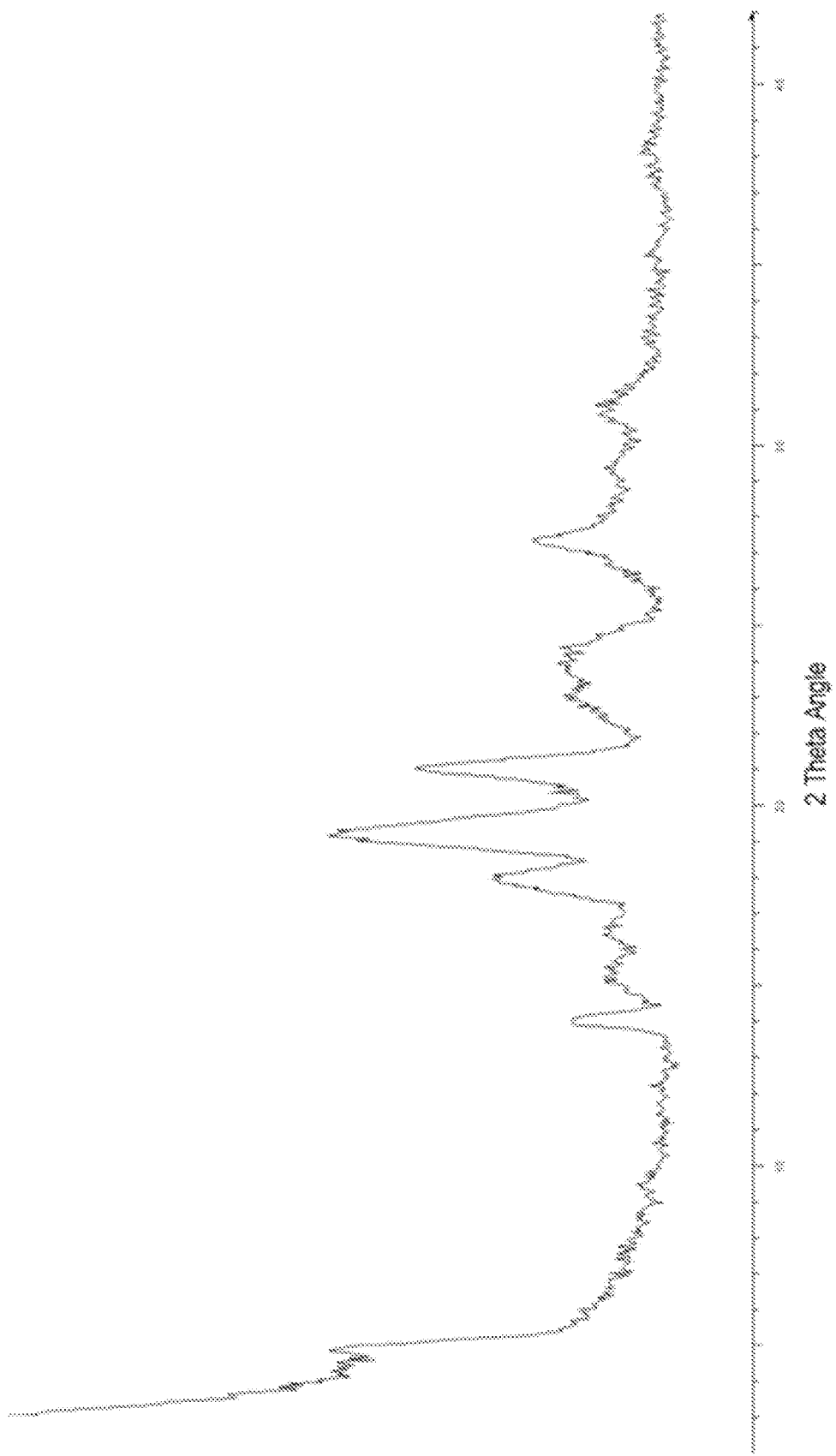
FIG. 6 illustrates a representative XRPD pattern for Form 2 of Compound II.
Figure 7:
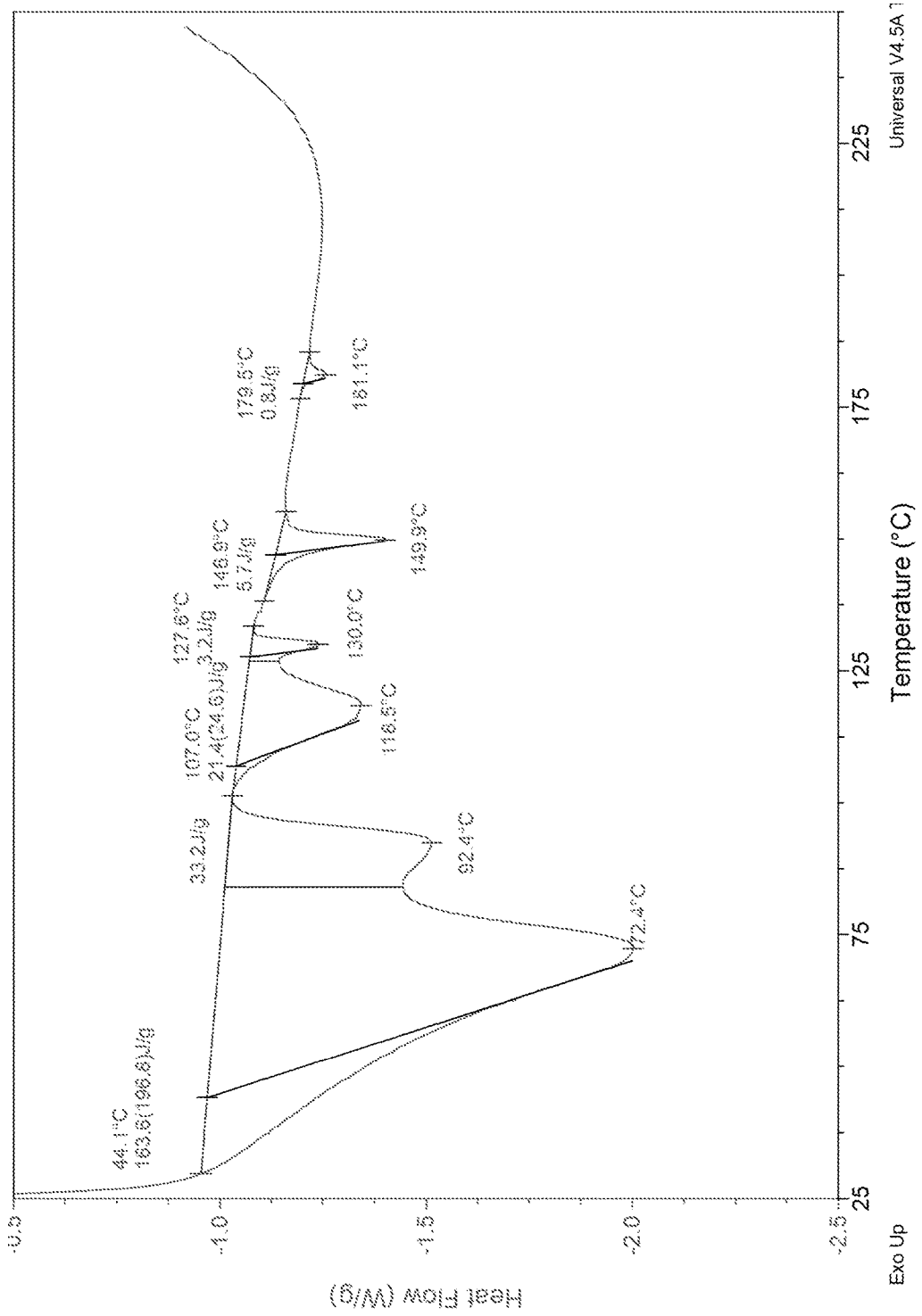
FIG. 7 illustrates a representative DSC thermogram for Form 2 of Compound II.
Figure 8:
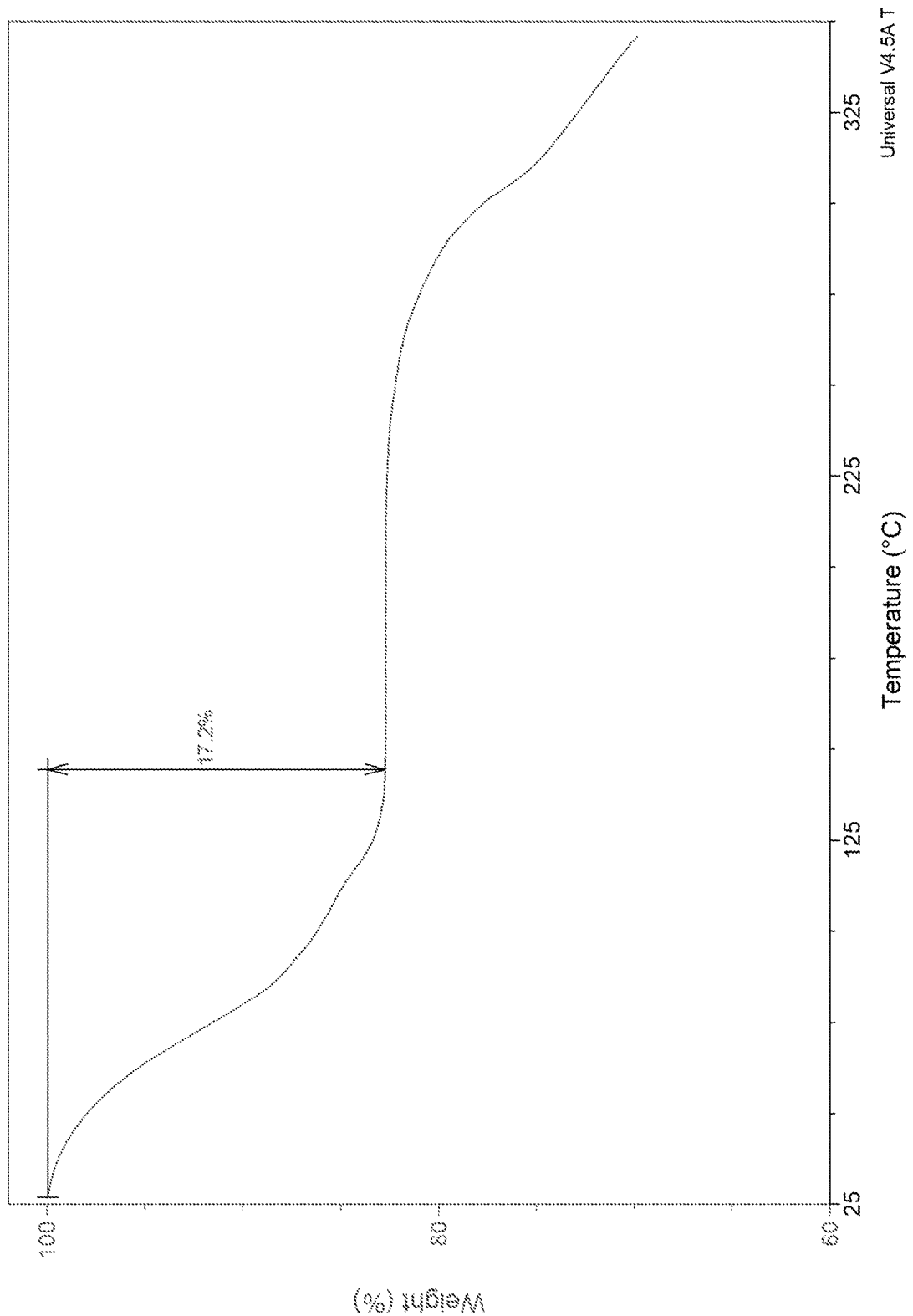
FIG. 8 illustrates a representative TGA thermogram for Form 2 of Compound II.

In some embodiments, crystalline Compound II is crystalline Form 2 of Compound II. Crystalline Form 2 is a hydrate of Compound II. In some embodiments, described herein is a composition comprising crystalline Form 2 of Compound II. In some embodiments, crystalline Form 2 of Compound II is characterized as having:

a) an XRPD pattern substantially the same as shown in FIG. 6;
b) an XRPD pattern with peaks at about 4.5 2-Theta, about 13.8° 2-Theta, about 17.6° 2-Theta, about 19.0° 2-Theta, about 19.6° 2-Theta, about 19.9° 2-Theta, about 20.5° 2-Theta, and about 23.0° 2-Theta as measured using Cu Kα radiation;
c) a DSC thermogram substantially the same as shown in FIG. 7;
d) a DSC thermogram with six endothermic events having:
  i. an onset at about 44.1° C. and a peak at about 72.4° C.;
  ii. a peak at about 92.4° C.;
  iii. an onset at about 107.0° C. and a peak at about 118.5° C.;
  iv. an onset at about 127.6° C. and a peak at about 130.0° C.;
  v. an onset at about 146.9° C. and a peak at about 149.9° C.; and
  vi. an onset at about 179.5° C. and a peak at about 181.1° C.;
e) a TGA pattern substantially the same as shown in FIG. 8;
f) a TGA pattern with a 17.2% w/w loss from 25 to 145° C., and degradation onset at about 275° C.;
g) reversible water uptake (~25% w/w) between 0 and 90% Relative Humidity (RH);
h) an unchanged XRPD after GVS analysis at 90% RH and 25° C.;
i) an unchanged XRPD after storage at 97% RH and 25° C. over 7 days;
j) an unchanged XRPD after storage at 75% RH and 40° C. over 7 days;
  or
k) combinations thereof.

In some embodiments, crystalline Form 2 of Compound II has an XRPD pattern substantially the same as shown in FIG. 6. In some embodiments, crystalline Form 2 of Compound II has an XRPD pattern with peaks at about 4.5 2-Theta, about 13.8° 2-Theta, about 17.6° 2-Theta, about 19.0° 2-Theta, about 19.6° 2-Theta, about 19.9° 2-Theta, about 20.5° 2-Theta, and about 23.0° 2-Theta as measured using Cu Kα radiation. In some embodiments, crystalline Form 2 of Compound II has a DSC thermogram substantially the same as shown in FIG. 7. In some embodiments, crystalline Form 2 of Compound II has a DSC thermogram with six endothermic events having: an onset at about 44.1° C. and a peak at about 72.4° C.; a peak at about 92.4° C.; an onset at about 107.0° C. and a peak at about 118.5° C.; an onset at about 127.6° C. and a peak at about 130.0° C.; an onset at about 146.9° C. and a peak at about 149.9° C.; and an onset at about 179.5° C. and a peak at about 181.1° C. In some embodiments, Form 2 of Compound II has a TGA pattern substantially the same as shown in FIG. 8. In some embodiments, crystalline Form 2 of Compound II has a TGA pattern with a 17.2% w/w loss from 25 to 145° C., and degradation onset at about 275° C. In some embodiments, crystalline Form 2 of Compound II has reversible water uptake (~25% w/w) between 0 and 90% Relative Humidity (RH). In some embodiments, crystalline Form 2 of Compound II an unchanged XRPD after GVS analysis at 90% RH and 25° C. In some embodiments, crystalline Form 2 of Compound II has an unchanged XRPD after storage at 97% RH and 25° C. over 7 days. In some embodiments, crystalline Form 2 of Compound II has an unchanged XRPD after storage at 75% RH and 40° C. over 7 days.

In some embodiments, crystalline Form 2 of Compound II has an XRPD pattern reflection at 4.5° 2-Theta as measured using Cu Kα radiation. In some embodiments, crystalline Form 2 is further characterized by XRPD pattern reflections at about 13.8° 2-Theta, about 17.6° 2-Theta, about 19.0° 2-Theta, about 19.6° 2-Theta, about 19.9° 2-Theta, about 20.5° 2-Theta, and about 23.0° 2-Theta. In some embodiments, crystalline Form 2 is further characterized by at least one XRPD pattern reflection selected from about 13.8° 2-Theta, about 17.6° 2-Theta, about 19.0° 2-Theta, about 19.6° 2-Theta, about 19.9° 2-Theta, about 20.5° 2-Theta, and about 23.0° 2-Theta. In some embodiments, crystalline Form 2 is further characterized by at least two XRPD pattern reflections selected from about 13.8° 2-Theta, about 17.6° 2-Theta, about 19.0° 2-Theta, about 19.6° 2-Theta, about 19.9° 2-Theta, about 20.5° 2-Theta, and about 23.0° 2-Theta. In some embodiments, crystalline Form 2 is further characterized by at least three XRPD pattern reflections selected from about 13.8° 2-Theta, about 17.6° 2-Theta, about 19.0° 2-Theta, about 19.6° 2-Theta, about 19.9° 2-Theta, about 20.5° 2-Theta, and about 23.0° 2-Theta.

Crystalline Form 3 of Compound II

In some embodiments, crystalline Compound II is crystalline Form 3 of Compound II. Crystalline Form 3 of Compound II is a solvate of Compound II. In some embodiments, described herein is a composition comprising crystalline Form 3 of Compound II. In some embodiments, crystalline Form 3 of Compound II is an isostructural solvate form that is formed with multiple solvents. In some embodiments, crystalline Form 3 of Compound II is a solvate with toluene, methyl isobutyl ketone (MIBK), or 2-methyltetrahydrofuran.

In some embodiments, crystalline Form 3 of Compound II is a crystalline 2-methyltetrahydrofuran solvate of Compound II.

Figure 9:
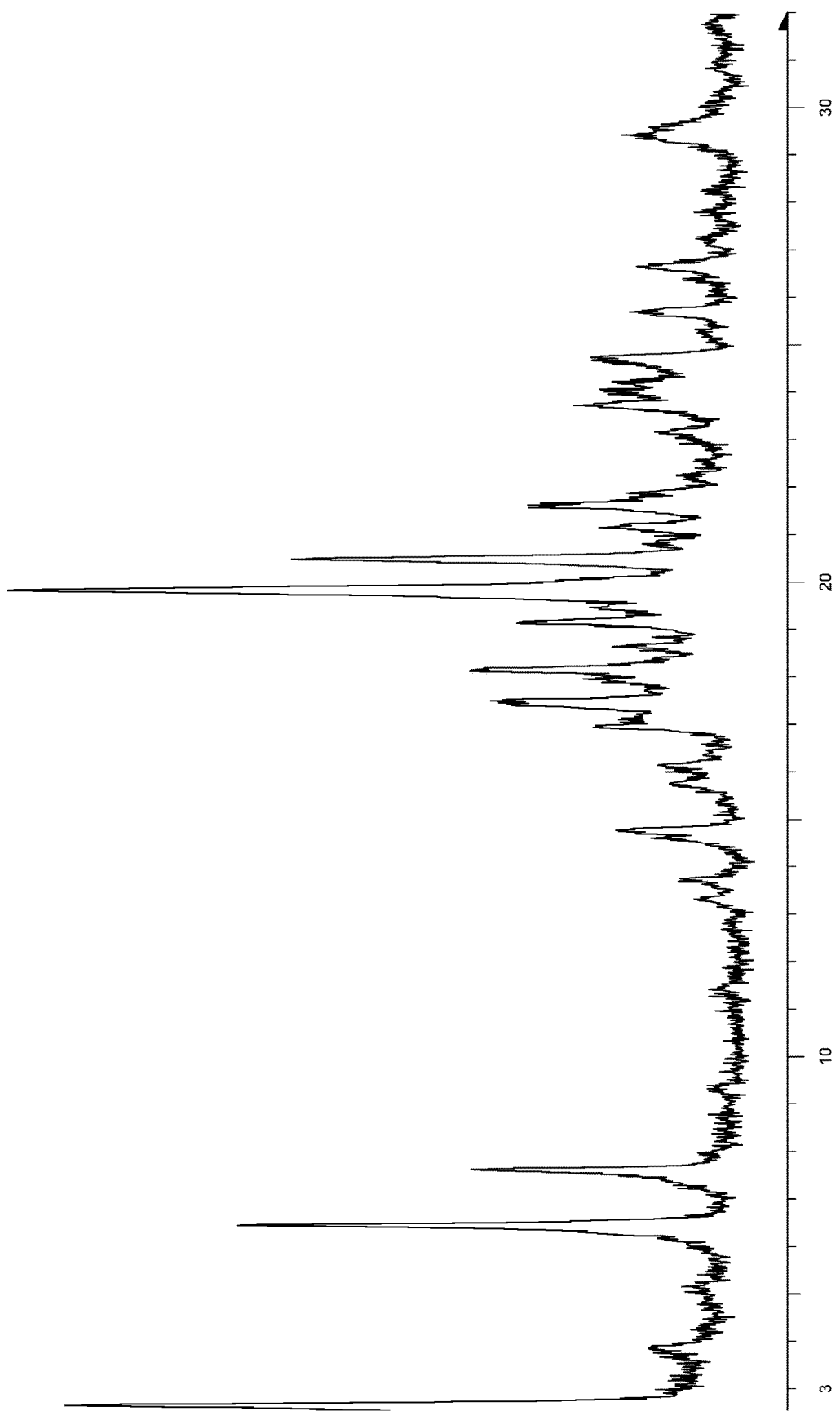
FIG. 9 illustrates a representative XRPD pattern for Form 3 of Compound II.
Figure 10:
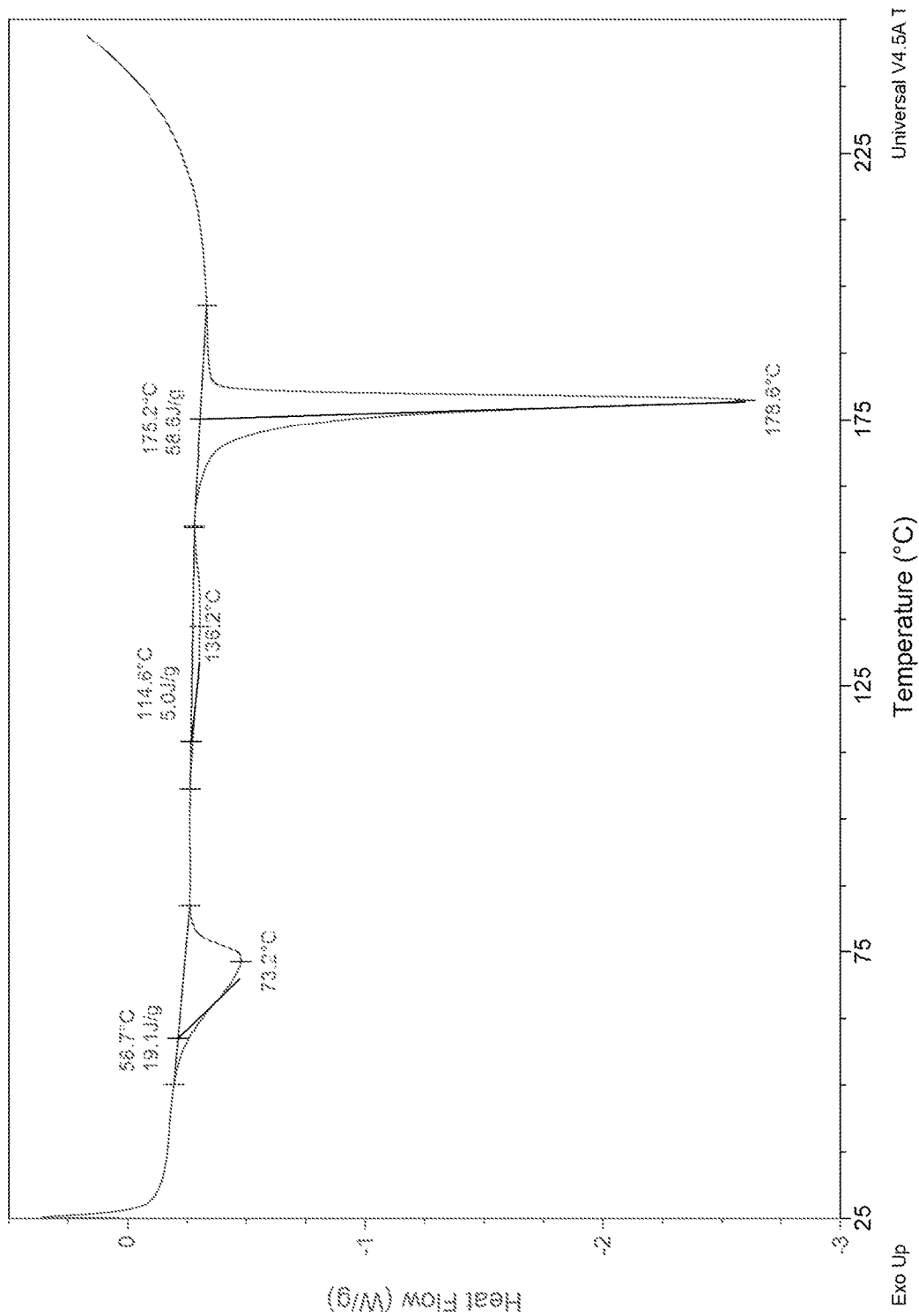
FIG. 10 illustrates a representative DSC thermogram for Form 3 of Compound II.
Figure 11:
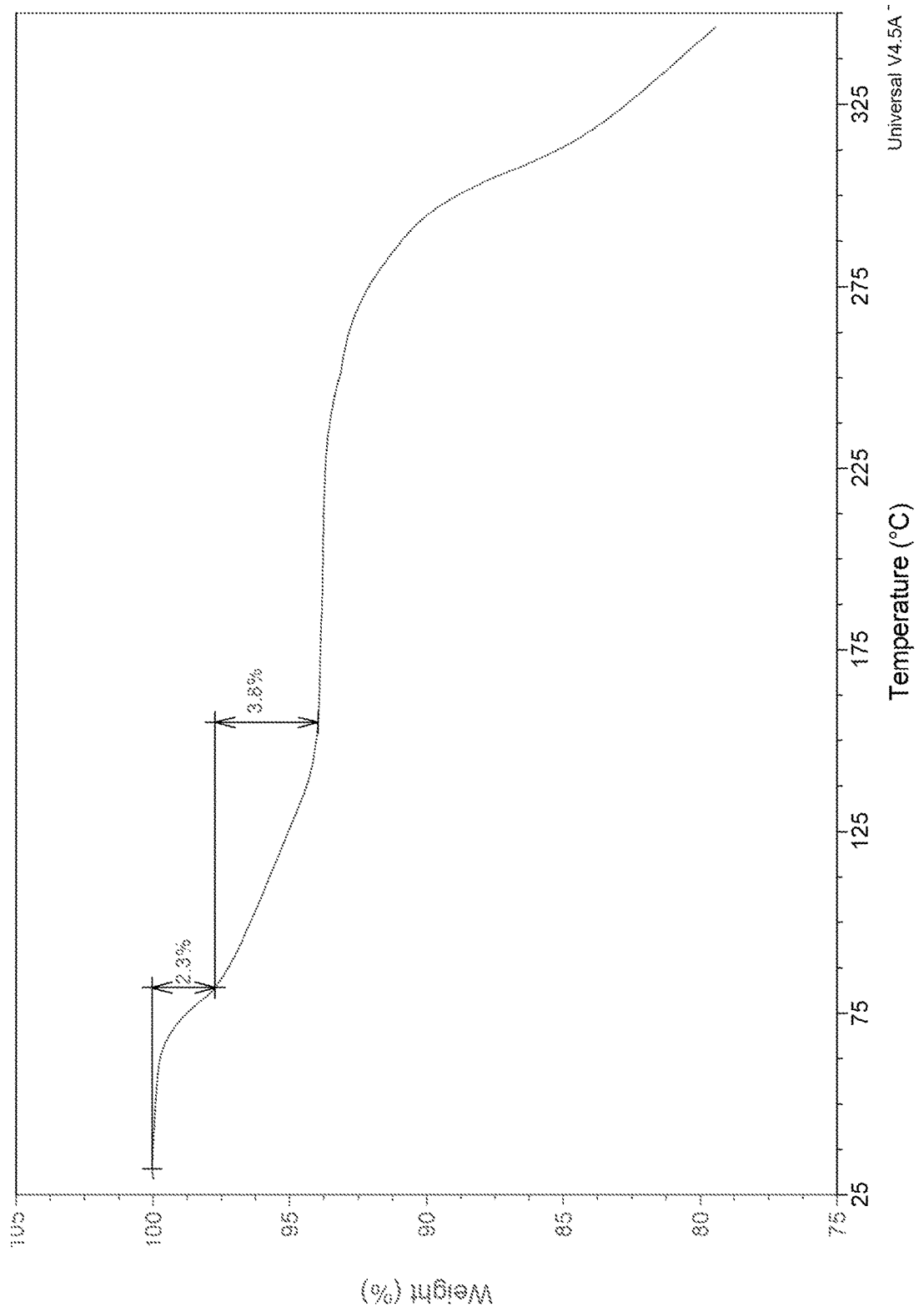
FIG. 11 illustrates a representative TGA thermogram for Form 3 of Compound II.

In some embodiments, crystalline Form 3 of Compound II is characterized as having:
a) an XRPD pattern substantially the same as shown in FIG. 9;
b) a DSC thermogram substantially the same as shown in FIG. 10;
c) a DSC thermogram with three endothermic events having:
   i. an onset at about 58.7° C. and a peak at about 73.2° C.;
   ii. an onset at about 114.5° C. and a peak at about 136.2° C.; and
   iii. an onset at about 172.5° C. and a peak at about 178.6° C.;
d) a TGA pattern substantially the same as shown in FIG. 11;
e) a TGA pattern with a 2.3% w/w loss from 25 to 82° C., a further 3.8% w/w loss from 82° C. to 155° C., and a degradation onset at about 275° C.;
f) reversible water uptake (~9.0% w/w) between 0 and 90% Relative Humidity (RH);
g) an XRPD that converts to Form 1 after GVS analysis at 90% RH and 25° C.;
h) an XRPD that converts to Form 1 after storage at 75% RH and 40° C. for 7 days; or
i) combinations thereof.

In some embodiments, crystalline Form 3 of Compound II has an XRPD pattern substantially the same as shown in FIG. 9. In some embodiments, crystalline Form 3 of Compound II has a DSC thermogram substantially the same as shown in FIG. 10. In some embodiments, crystalline Form 3 of Compound II has a DSC thermogram with three endothermic events having: an onset at about 58.7° C. and a peak at about 73.2° C.; an onset at about 114.5° C. and a peak at about 136.2° C.; an onset at about 172.5° C. and a peak at about 178.6° C. In some embodiments, crystalline Form 3 of Compound II has a TGA pattern substantially the same as shown in FIG. 11. In some embodiments, crystalline Form 3 of Compound II has a TGA pattern with a 2.3% w/w loss from 25 to 82° C., a further 3.8% w/w loss from 82° C. to 155° C., and a degradation onset at about 275° C. In some embodiments, crystalline Form 3 of Compound II has reversible water uptake (~9.0% w/w) between 0 and 90% Relative Humidity (RH). In some embodiments, crystalline Form 3 of Compound II has an XRPD that converts to Form 1 after GVS analysis at 90% RH and 25° C. In some embodiments, crystalline Form 3 of Compound II has an XRPD that converts to Form 1 after storage at 75% RH and 40° C. for 7 days.

In some embodiments, the crystalline Form 3 of Compound II is unstable and converts to Form 1 on drying. In some embodiments, the crystalline Form 3 of Compound II is unstable and converts to Form 1 on standing in ambient conditions.

Crystalline Form 4 of Compound II

In some embodiments, crystalline Compound II is crystalline Form 4 of Compound II.

Crystalline Form 4 of Compound II is a solvate. In some embodiments, described herein is a composition comprising crystalline Form 4 of Compound II. In some embodiments, crystalline Form 4 of Compound II is an isostructural solvate form that is formed with multiple solvents. In some embodiments, crystalline Form 4 of Compound II is solvated with methyl isobutyl ketone, 1,4-dioxane, chloroform, tetrahydrofuran, or dichloromethane.

In some embodiments, crystalline Form 4 of Compound II is a tetrahydrofuran solvate.

Figure 12:
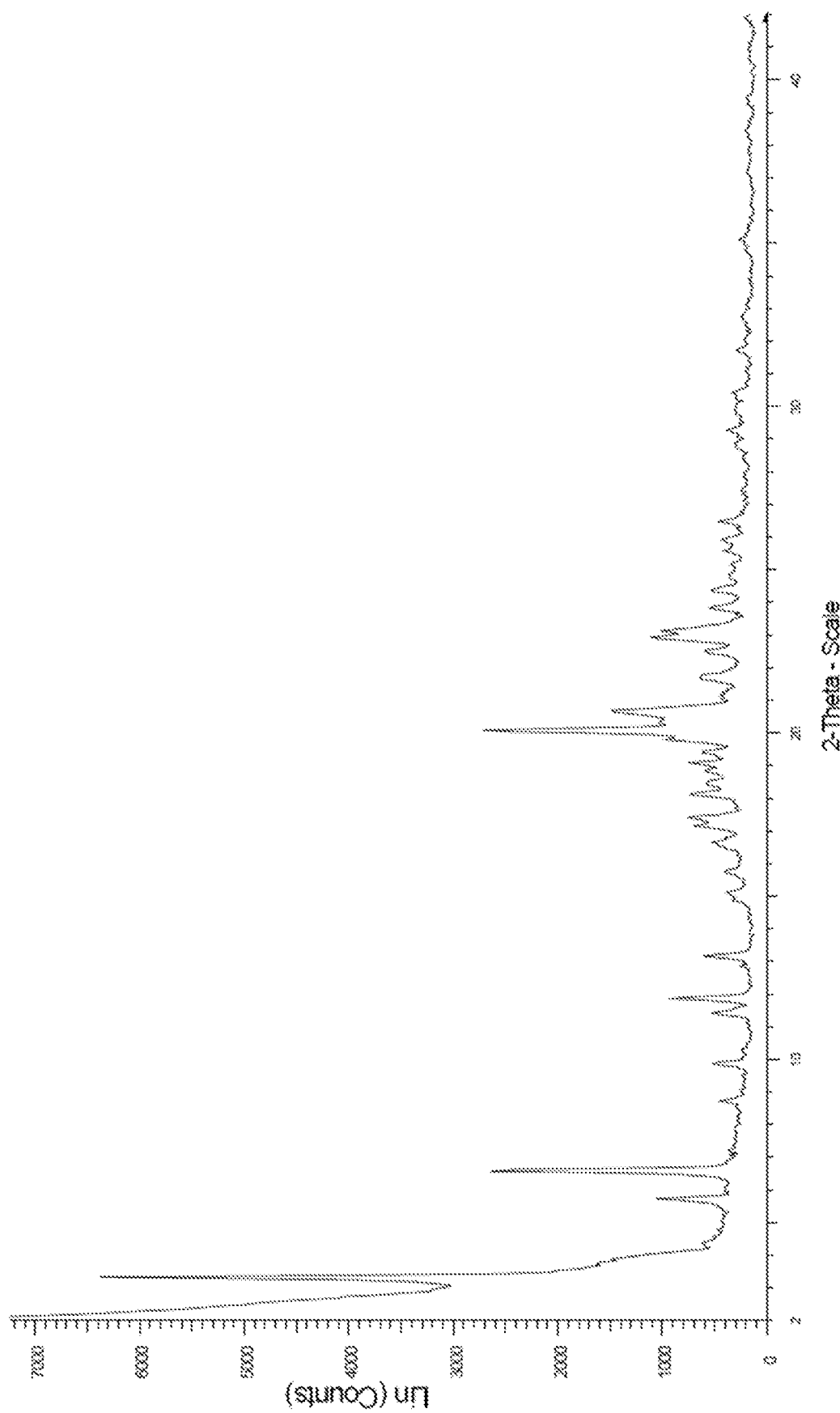
FIG. 12 illustrates a representative XRPD pattern for Form 4 of Compound II.
Figure 13:
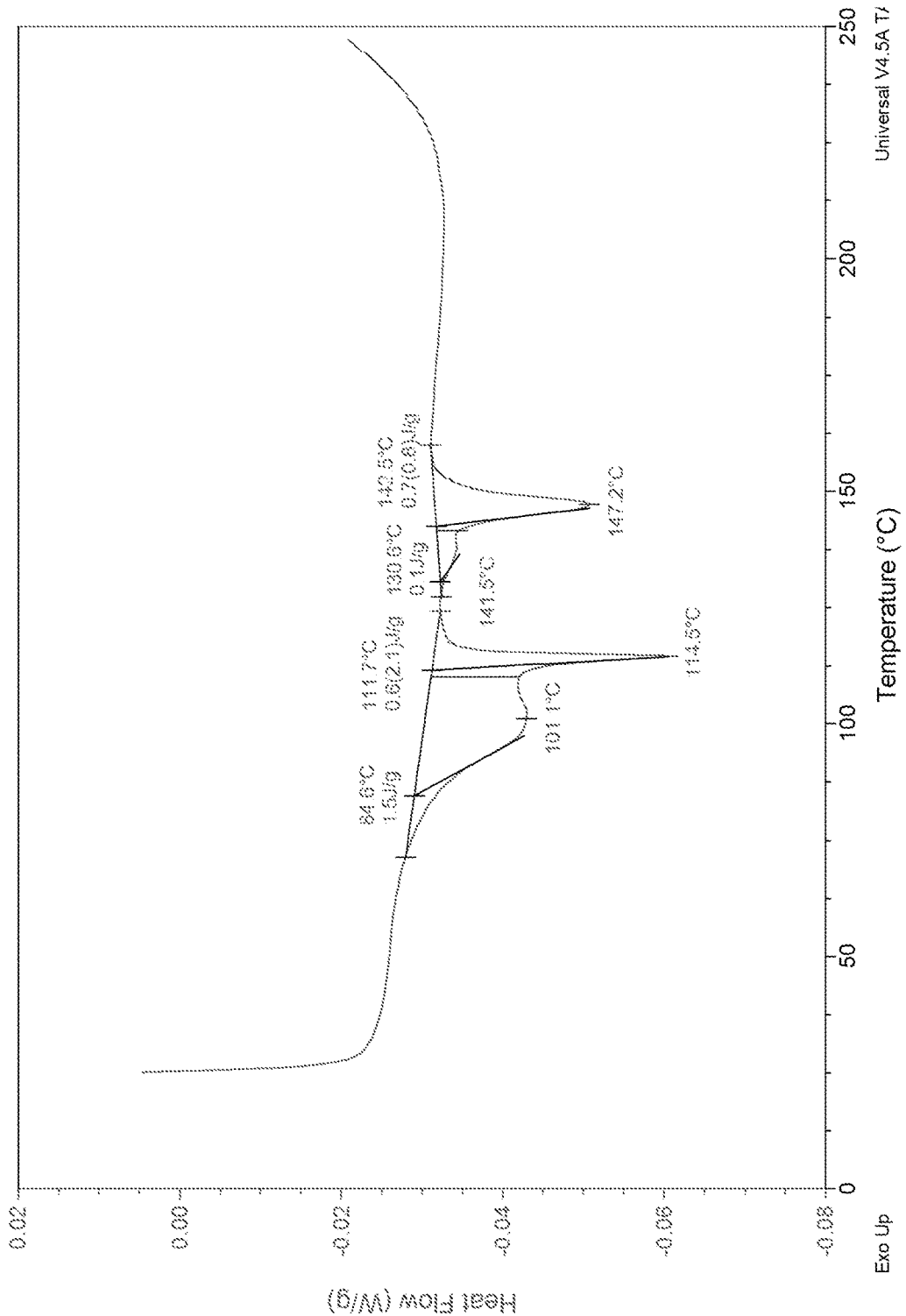
FIG. 13 illustrates a representative DSC thermogram for Form 4 of Compound II.
Figure 14:
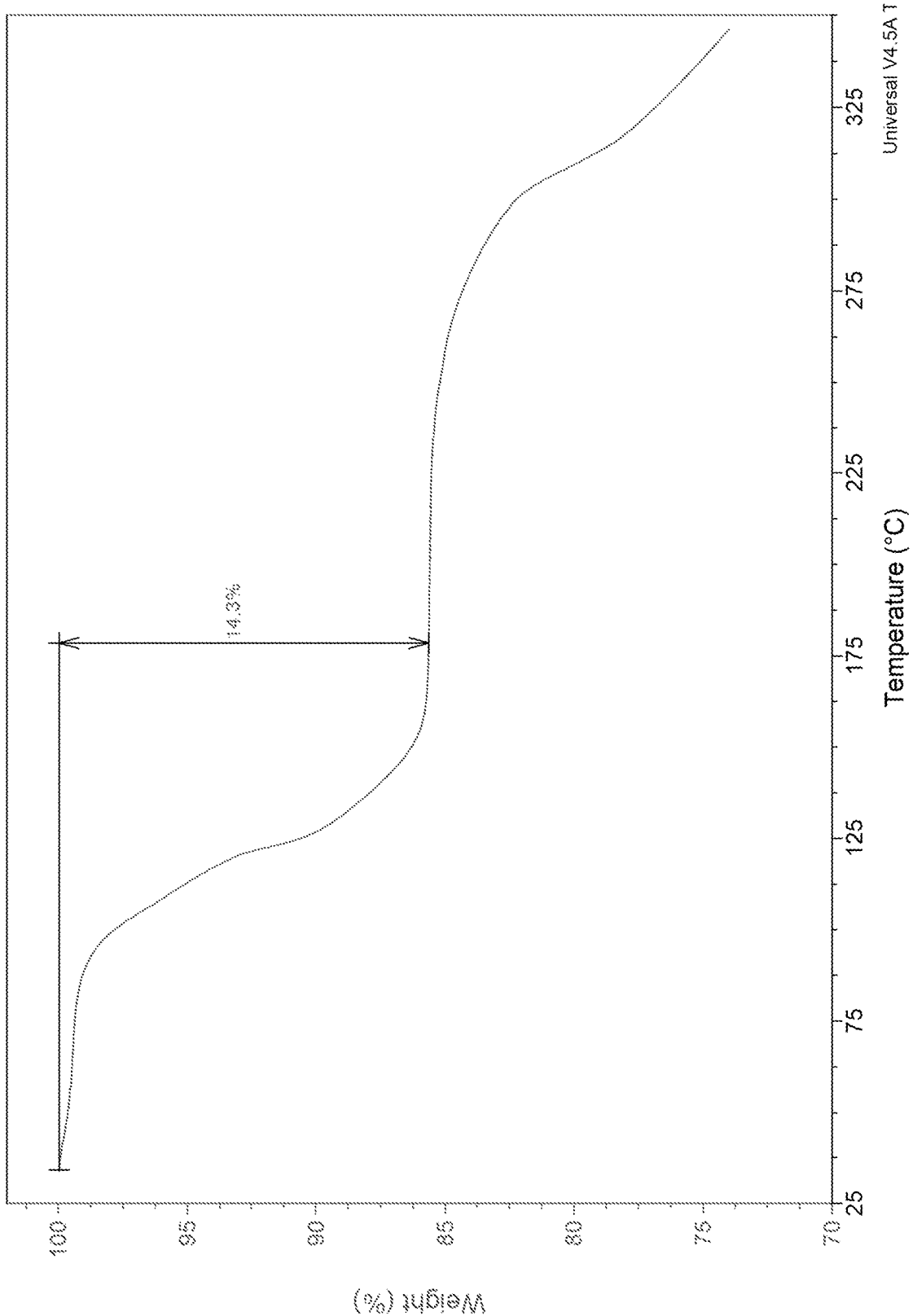
FIG. 14 illustrates a representative TGA thermogram for Form 4 of Compound II.

In some embodiments, crystalline Form 4 of Compound II is characterized as having:
a) an XRPD pattern substantially the same as shown in FIG. 12;
b) an XRPD pattern with peaks at about 3.3° 2-Theta, about 6.7° 2-Theta, about 20.1° 2-Theta, and about 20.7° 2-Theta as measured using Cu Kα radiation;
c) a DSC thermogram substantially the same as shown in FIG. 13;
d) a DSC thermogram with two endothermic events having:
   i. an onset at about 111.7° C. and a peak at about 114.5° C. with a broad shoulder starting at about 70° C.; and
   ii. an onset at about 142.5° C. and a peak at about 147.2° C. with a broad shoulder starting at about 130.6° C.;
e) a TGA pattern substantially the same as shown in FIG. 14;
f) a TGA pattern with a 14.3% w/w loss from 25 to 175° C., and degradation onset at about 285° C.;
g) reversible water uptake (~23% w/w) between 0 and 90% Relative Humidity (RH);
h) an XRPD that converts to Form 2 after GVS analysis at 90% RH and 25° C.;
i) an unchanged XRPD after heating to 110° C.;
j) an XRPD that converts to Form 2 after storage at 97% RH and 25° C. over 7 days;

k) an XRPD that converts to Form 1 after storage at 75% RH and 40° C. over 7 days;
or
l) combinations thereof.

In some embodiments, crystalline Form 4 of Compound II has an XRPD pattern substantially the same as shown in FIG. 12. In some embodiments, crystalline Form 4 of Compound II has an XRPD pattern with peaks at about 3.3° 2-Theta, about 6.7° 2-Theta, about 20.1° 2-Theta, and about 20.7° 2-Theta as measured using Cu Kα radiation. In some embodiments, crystalline Form 4 of Compound II has a DSC thermogram substantially the same as shown in FIG. 13. In some embodiments, crystalline Form 4 of Compound II has a DSC thermogram with two endothermic events having: an onset at about 111.7° C. and a peak at about 114.5° C. with a broad shoulder starting at about 70° C.; and an onset at about 142.5° C. and a peak at about 147.2° C. with a broad shoulder starting at about 130.6° C. In some embodiments, crystalline Form 4 of Compound II has a TGA pattern substantially the same as shown in FIG. 14. In some embodiments, crystalline Form 4 of Compound II has a TGA pattern with a 14.3% w/w loss from 25 to 175° C., and degradation onset at about 285° C. In some embodiments, crystalline Form 4 of Compound II has reversible water uptake (~23% w/w) between 0 and 90% Relative Humidity (RH). In some embodiments, crystalline Form 4 of Compound II has an XRPD that converts to Form 2 after GVS analysis at 90% RH and 25° C. In some embodiments, crystalline Form 4 of Compound II has an unchanged XRPD after heating to 110° C. In some embodiments, crystalline Form 4 of Compound II has an XRPD that converts to Form 2 after storage at 97% RH and 25° C. over 7 days. In some embodiments, crystalline Form 4 of Compound II has an XRPD that converts to Form 1 after storage at 75% RH and 40° C. over 7 days.

In some embodiments, crystalline Form 4 of Compound II has an XRPD pattern reflection at 3.3° 2-Theta as measured using Cu Kα radiation. In some embodiments, crystalline Form 4 is further characterized by XRPD pattern reflections at 20.1° 2-Theta and 20.7° 2-Theta. In some embodiments, crystalline Form 4 is further characterized by XRPD pattern reflections at 5.7° 2-Theta, 11.9° 2-Theta, 17.2° 2-Theta, 17.4° 2-Theta, 18.1° 2-Theta, 19.1° 2-Theta, 19.8° 2-Theta, 22.9° 2-Theta, and 23.1° 2-Theta. In some embodiments, crystalline Form 4 is further characterized by at least one XRPD pattern reflection selected from 5.7° 2-Theta, 11.9° 2-Theta, 17.2° 2-Theta, 17.4° 2-Theta, 18.1° 2-Theta, 19.1° 2-Theta, 19.8° 2-Theta, 22.9° 2-Theta, and 23.1° 2-Theta. In some embodiments, crystalline Form 4 is further characterized by at least two XRPD pattern reflections selected from 5.7° 2-Theta, 11.9° 2-Theta, 17.2° 2-Theta, 17.4° 2-Theta, 18.1° 2-Theta, 19.1° 2-Theta, 19.8° 2-Theta, 22.9° 2-Theta, and 23.1° 2-Theta. In some embodiments, crystalline Form 4 is further characterized by at least three XRPD pattern reflections selected from 5.7° 2-Theta, 11.9° 2-Theta, 17.2° 2-Theta, 17.4° 2-Theta, 18.1° 2-Theta, 19.1° 2-Theta, 19.8° 2-Theta, 22.9° 2-Theta, and 23.1° 2-Theta.

Crystalline Form 5 of Compound II

In some embodiments, crystalline Compound II is crystalline Form 5 of Compound II. Crystalline Form 5 of Compound II is a solvate. In some embodiments, described herein is a composition comprising crystalline Form 5 of Compound II. In some embodiments, crystalline Form 5 of Compound II is an isostructural solvate form that is formed with multiple solvents. In some embodiments, crystalline Form 5 of Compound II is solvated with acetone, methyl ethyl ketone, diethyl ether, or ethyl acetate.

In some embodiments, crystalline Form 5 of Compound II is an acetone solvate.

Figure 15:
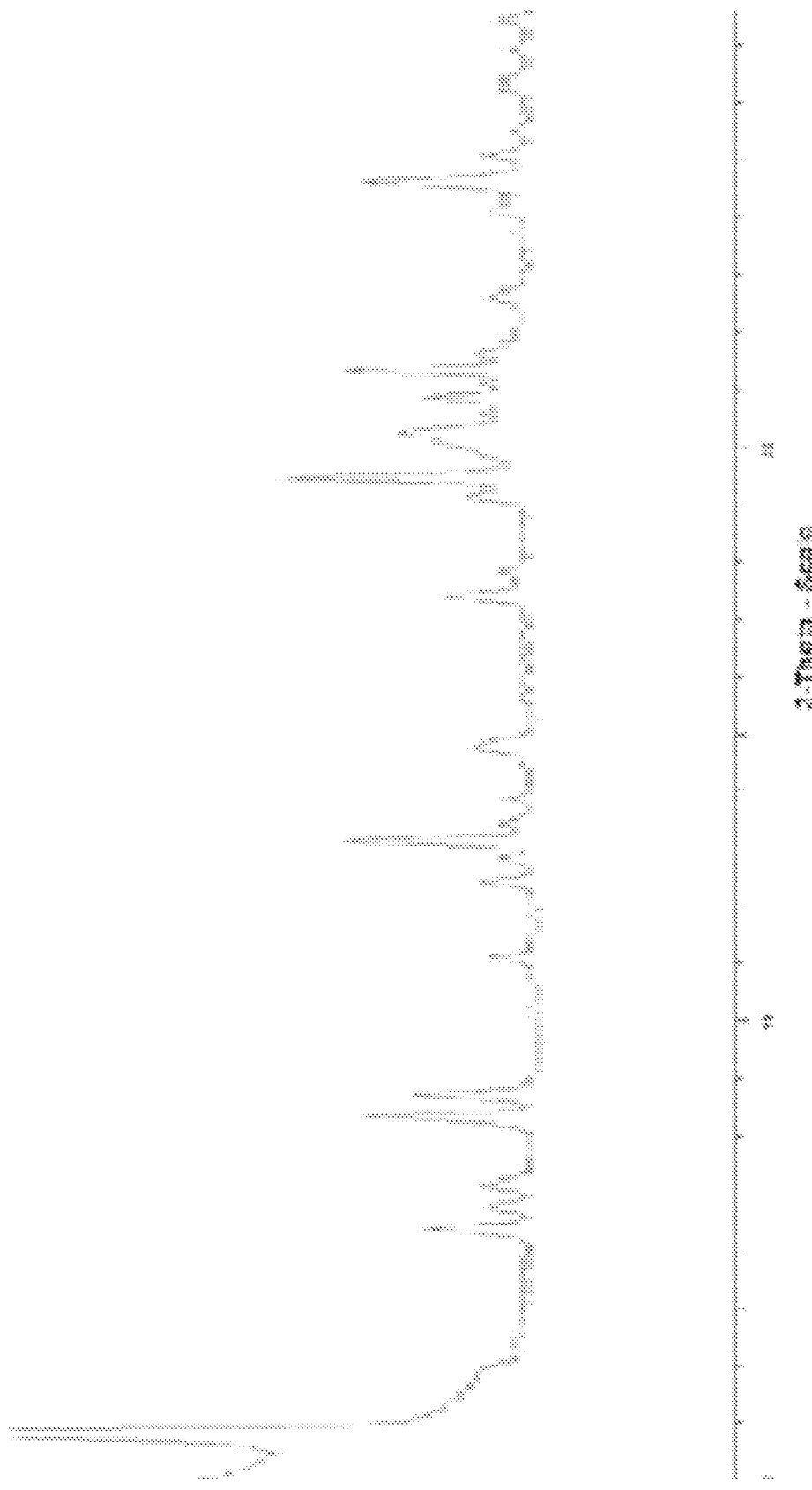
FIG. 15 illustrates a representative XRPD pattern for Form 5 of Compound II.
Figure 16:
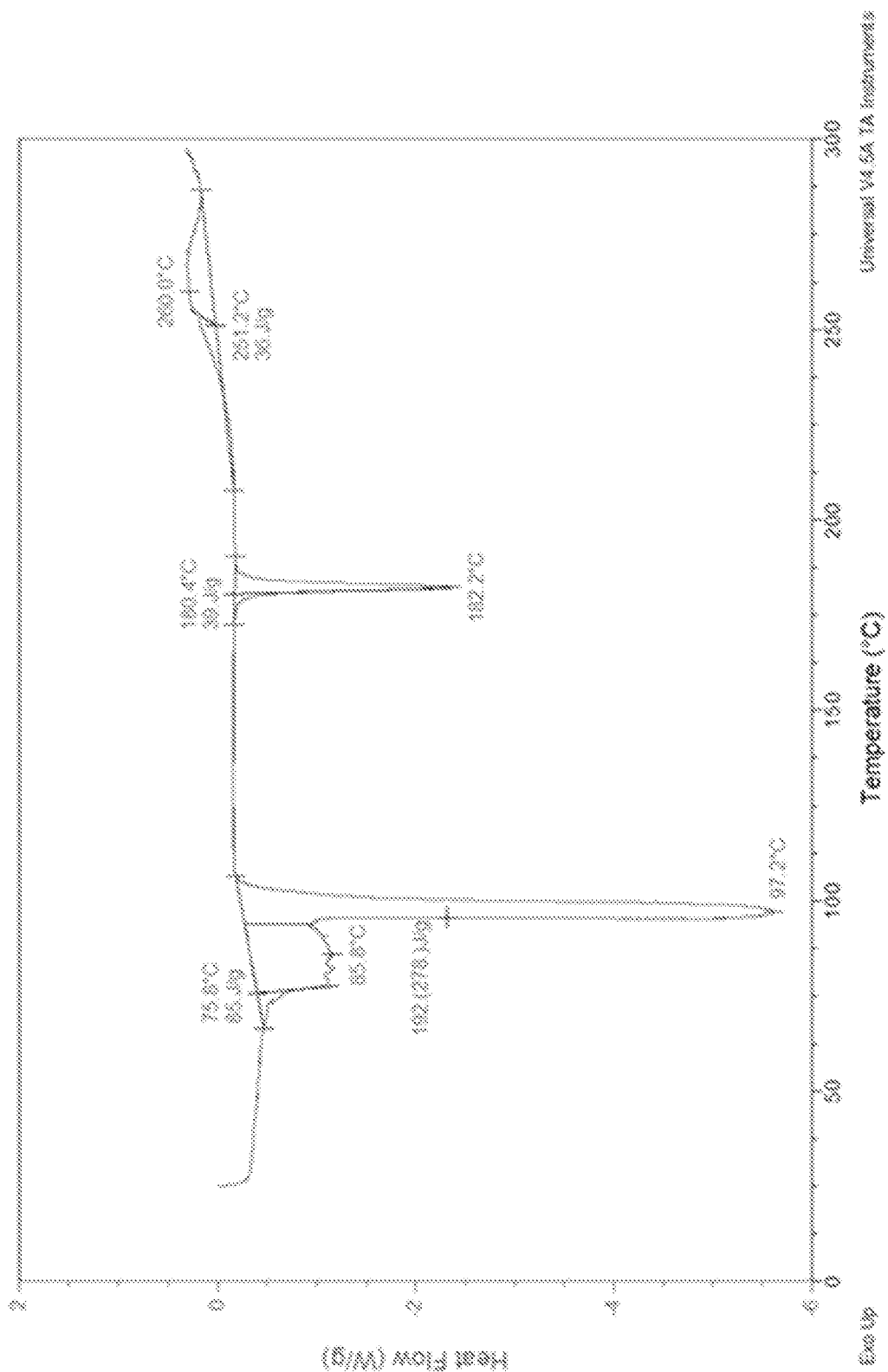
FIG. 16 illustrates a representative DSC thermogram for Form 5 of Compound II.
Figure 17:
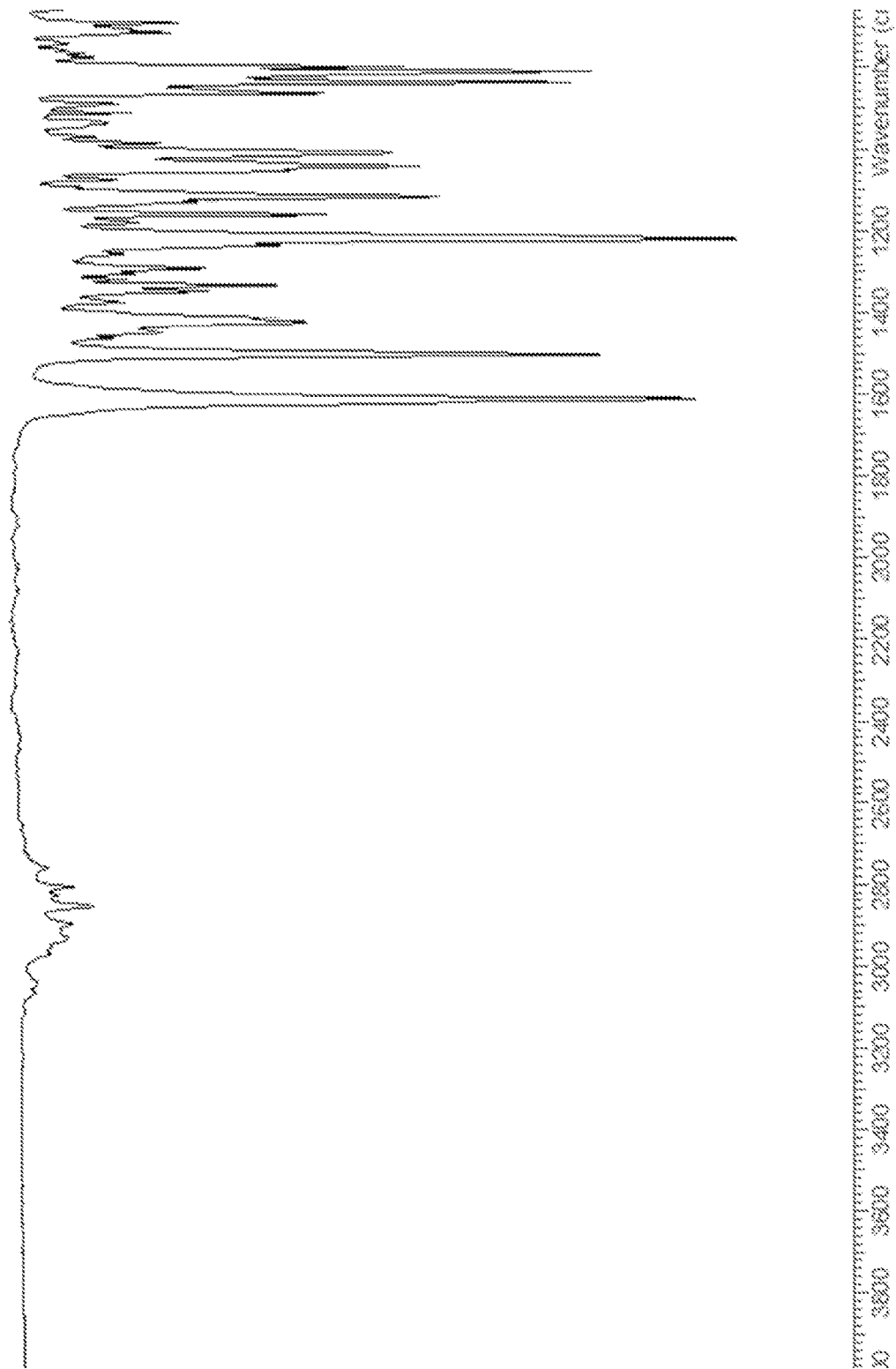
FIG. 17 illustrates a representative FTIR spectrum for Form 5 of Compound II.

In some embodiments, crystalline Form 5 of Compound II is characterized as having:
a) an XRPD pattern substantially the same as shown in FIG. 15;
b) an XRPD pattern with peaks at about 2.8 2-Theta, about 8.3° 2-Theta, about 8.7° 2-Theta, about 13.1° 2-Theta, about 19.4° 2-Theta, about 20.2° 2-Theta, about 21.3° 2-Theta, and about 24.6° 2-Theta as measured using Cu Kα radiation;
c) a DSC thermogram substantially the same as shown in FIG. 16;
d) a DSC thermogram with two endothermic events having:
i. an onset at 75.8° C. and two peaks at about 85.8° C. and 97.2° C.; and
ii. onset at 180.4° C. and a peak at 182.2;
e) an FTIR spectroscopy pattern substantially the same as shown in FIG. 17; or
f) an FTIR spectroscopy pattern with peaks at about 810 cm$^{-1}$, about 838 cm$^{-1}$, about 1220 cm$^{-1}$, about 1504 cm$^{-1}$, and about 1612 cm$^{-1}$;
or
g) combinations thereof.

In some embodiments, crystalline Form 5 of Compound II has an XRPD pattern substantially the same as shown in FIG. 15. In some embodiments, crystalline Form 5 of Compound II has an XRPD pattern with peaks at about 2.8 2-Theta, about 8.3° 2-Theta, about 8.7° 2-Theta, about 13.1° 2-Theta, about 19.4° 2-Theta, about 20.2° 2-Theta, about 21.3° 2-Theta, and about 24.6° 2-Theta as measured using Cu Kα radiation. In some embodiments, crystalline Form 5 of Compound II has a DSC thermogram substantially the same as shown in FIG. 16. In some embodiments, crystalline Form 5 of Compound II has a DSC thermogram with two endothermic events having: an onset at 75.8° C. and two peaks at about 85.8° C. and 97.2° C.; and onset at 180.4° C. and a peak at 182.2. In some embodiments, crystalline Form 5 of Compound II has an FTIR spectroscopy pattern substantially the same as shown in FIG. 17. In some embodiments, crystalline Form 5 of Compound II has an FTIR spectroscopy pattern with peaks at about 810 cm$^{-1}$, about 838 cm$^{-1}$, about 1220 cm$^{-1}$, about 1504 cm$^{-1}$, and about 1612 cm$^{-1}$. In some embodiments, crystalline Form 5 of Compound II is unstable and converts to Form 1 on drying. In some embodiments, crystalline Form 5 of Compound II has an XRPD that converts to Form 1 after drying. In some embodiments, crystalline Form 5 of Compound II has an XRPD that converts to Form 1 after GVS analysis at 90% RH and 25° C.

In some embodiments, crystalline Form 5 of Compound II has an XRPD pattern reflection at 2.8° 2-Theta as measured using Cu Kα radiation. In some embodiments, crystalline Form 5 is further characterized by XRPD pattern reflections at about 8.3° 2-Theta, about 8.7° 2-Theta, about 13.1° 2-Theta, about 19.4° 2-Theta, about 20.2° 2-Theta, about 21.3° 2-Theta, and about 24.6° 2-Theta. In some embodiments, crystalline Form 5 is further characterized by at least one XRPD pattern reflection selected from about 8.3° 2-Theta, about 8.7° 2-Theta, about 13.1° 2-Theta, about 19.4° 2-Theta, about 20.2° 2-Theta, about 21.3° 2-Theta, and about 24.6° 2-Theta. In some embodiments, crystalline Form 5 is further characterized by at least two XRPD pattern reflections selected from about 8.3° 2-Theta, about 8.7° 2-Theta, about 13.1° 2-Theta, about 19.4° 2-Theta, about 20.2° 2-Theta, about 21.3° 2-Theta, and about 24.6°

2-Theta. In some embodiments, crystalline Form 5 is further characterized by at least three XRPD pattern reflections selected from about 8.3° 2-Theta, about 8.7° 2-Theta, about 13.1° 2-Theta, about 19.4° 2-Theta, about 20.2° 2-Theta, about 21.3° 2-Theta, and about 24.6° 2-Theta.

In some embodiments, disclosed herein is crystalline Compound II solvate. In some embodiments, the crystalline Compound II solvate is an isostructural solvate that is formed with multiple solvents. In some embodiments, the crystalline Compound II solvate is a solvate with diethyl ether, ethyl acetate, methyl isobutyl ketone, methyl ethyl ketone, 1-propanol, 1,4-dioxane, toluene, chloroform, tetrahydrofuran, dichloromethane, or 2-methyltetrahydrofuran. In some embodiments, the crystalline Compound II solvate is a crystalline solvate with 1,4-dioxane, tetrahydrofuran, or 2-methyltetrahydrofuran.

In some embodiments, disclosed herein is a crystalline Compound II hydrate.

Crystalline Pattern 9 of Compound II

Figure 19:
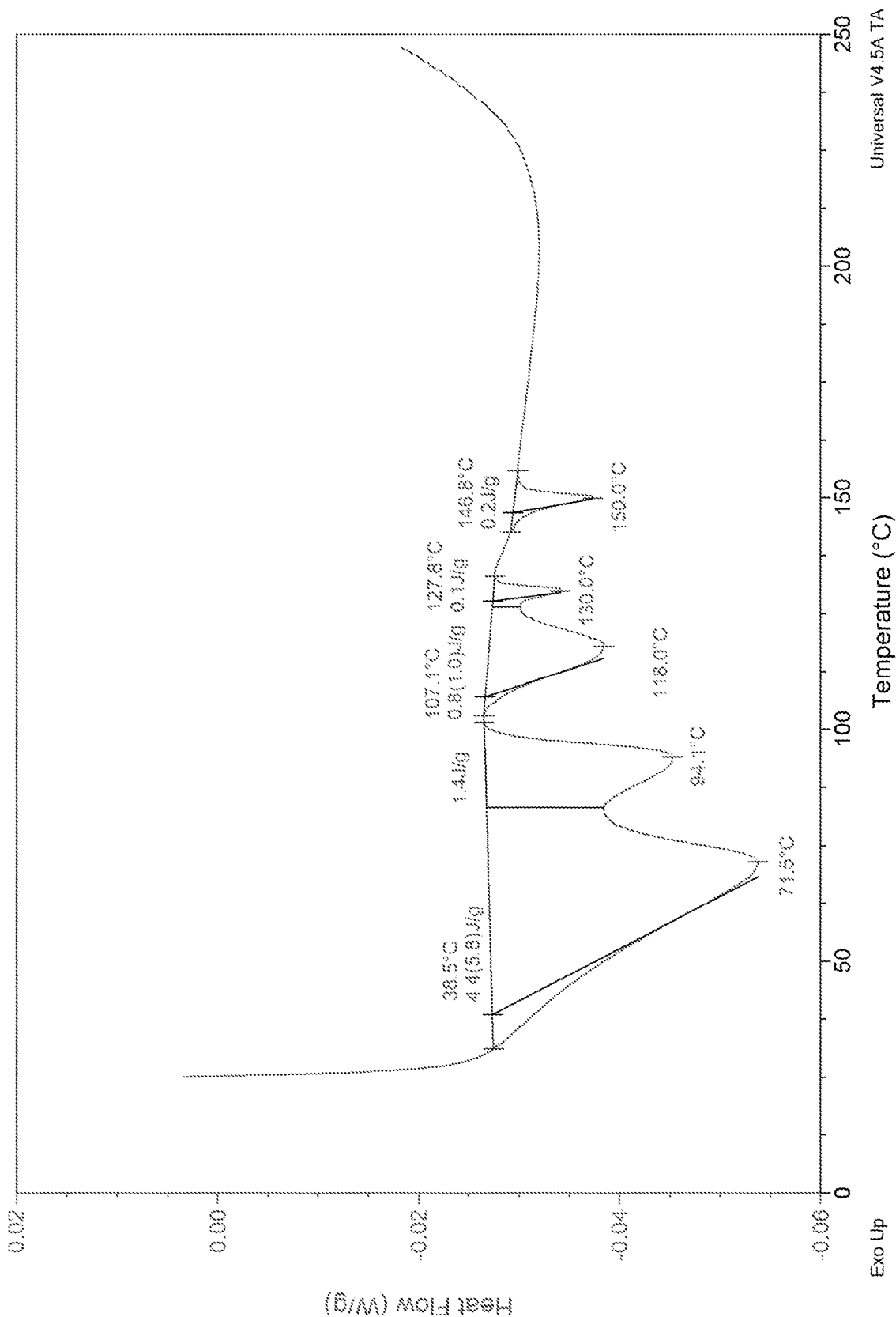
FIG. 19 illustrates a representative DSC thermogram for Pattern 9 of Compound II.
Figure 20:
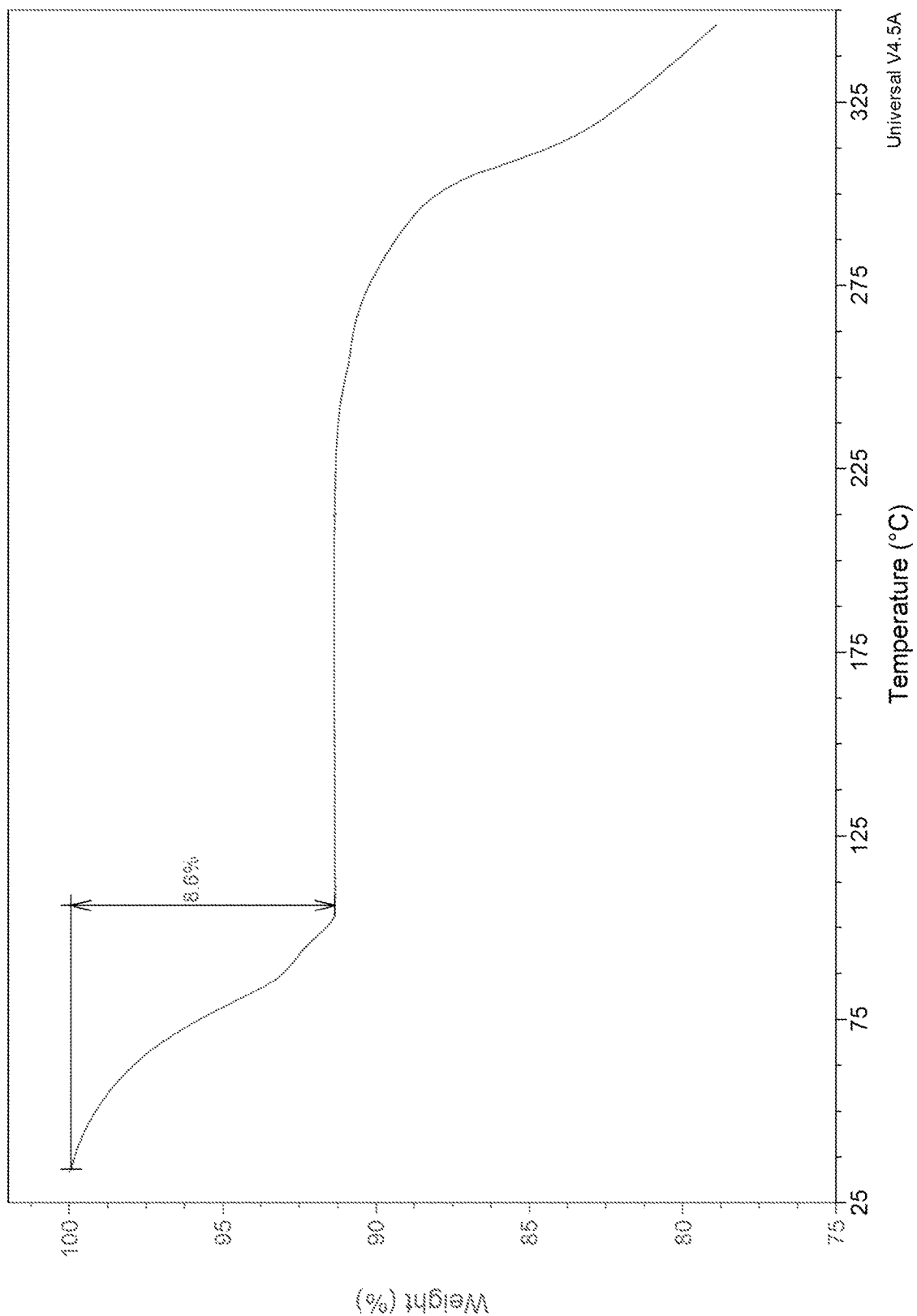
FIG. 20 illustrates a representative TGA thermogram for Pattern 9 of Compound II.

In some embodiments, crystalline Compound II is crystalline Pattern 9 of Compound II. Pattern 9 of Compound II is a hydrate. In some embodiments, crystalline Pattern 9 of Compound II is characterized as having:
a) an XRPD pattern substantially the same as shown in FIG. 18;
b) a DSC thermogram substantially the same as shown in FIG. 19;
c) a DSC thermogram with three endothermic events having:
  i. an onset at about 38.5° C. and two peaks at about 71.5° C. and 94.1° C.;
  ii. an onset at about 107.1° C. and two peaks at about 118.0° C. and 130.0° C.; and
  iii. an onset at about 146.8° C. and a peak at about 150.0° C.;
d) a TGA pattern substantially the same as shown in FIG. 20;
e) a TGA pattern with a 8.6% w/w loss from 25 to 105° C., and degradation onset at about 270° C.;
f) reversible water uptake (~27% w/w) between 0 and 90% Relative Humidity (RH); and
g) an unchanged XRPD after GVS analysis at 90% RH and 25° C.;
or
h) combinations thereof.

Figure 18:
FIG. 18 illustrates a representative XRPD pattern for Pattern 9 of Compound II.

In some embodiments, crystalline Pattern 9 of Compound II has an XRPD pattern substantially the same as shown in FIG. 18. In some embodiments, crystalline Pattern 9 of Compound II has a DSC thermogram substantially the same as shown in FIG. 19. In some embodiments, crystalline Pattern 9 of Compound II has a DSC thermogram with three endothermic events having: an onset at about 38.5° C. and two peaks at about 71.5° C. and 94.1° C.; an onset at about 107.1° C. and two peaks at about 118.0° C. and 130.0° C.; and an onset at about 146.8° C. and a peak at about 150.0° C. In some embodiments, crystalline Pattern 9 of Compound II has a TGA pattern substantially the same as shown in FIG. 20. In some embodiments, crystalline Pattern 9 of Compound II has a TGA pattern with a 8.6% w/w loss from 25 to 105° C., and degradation onset at about 270° C. In some embodiments, crystalline Pattern 9 of Compound II has reversible water uptake (~27% w/w) between 0 and 90% Relative Humidity (RH). In some embodiments, crystalline Pattern 9 of Compound II has an unchanged XRPD after GVS analysis at 90% RH and 25° C.

In some embodiments, provided herein is crystalline Compound II 2-methyltetrahydrofuran solvate (Pattern 5). In some embodiments, the crystalline Compound II 2-methyltetrahydrofuran solvate (Pattern 5) is unstable.

In some embodiments, provided herein is crystalline Compound II 1,4-dioxane solvate (Pattern 6). In some embodiments, the crystalline Compound II 1,4-dioxane solvate (Pattern 6) is unstable.

In some embodiments, provided herein is crystalline Compound II solvate Pattern 8. In some embodiments, crystalline Compound II solvate Pattern 8 is an isostructural solvate form that is formed with multiple solvents. In some embodiments, crystalline Compound II solvate Pattern 8 is a crystalline solvate with ethyl acetate. In some embodiments, the crystalline Compound II solvate Pattern 8 is unstable and converts to Form 1 on drying.

Figure 24:
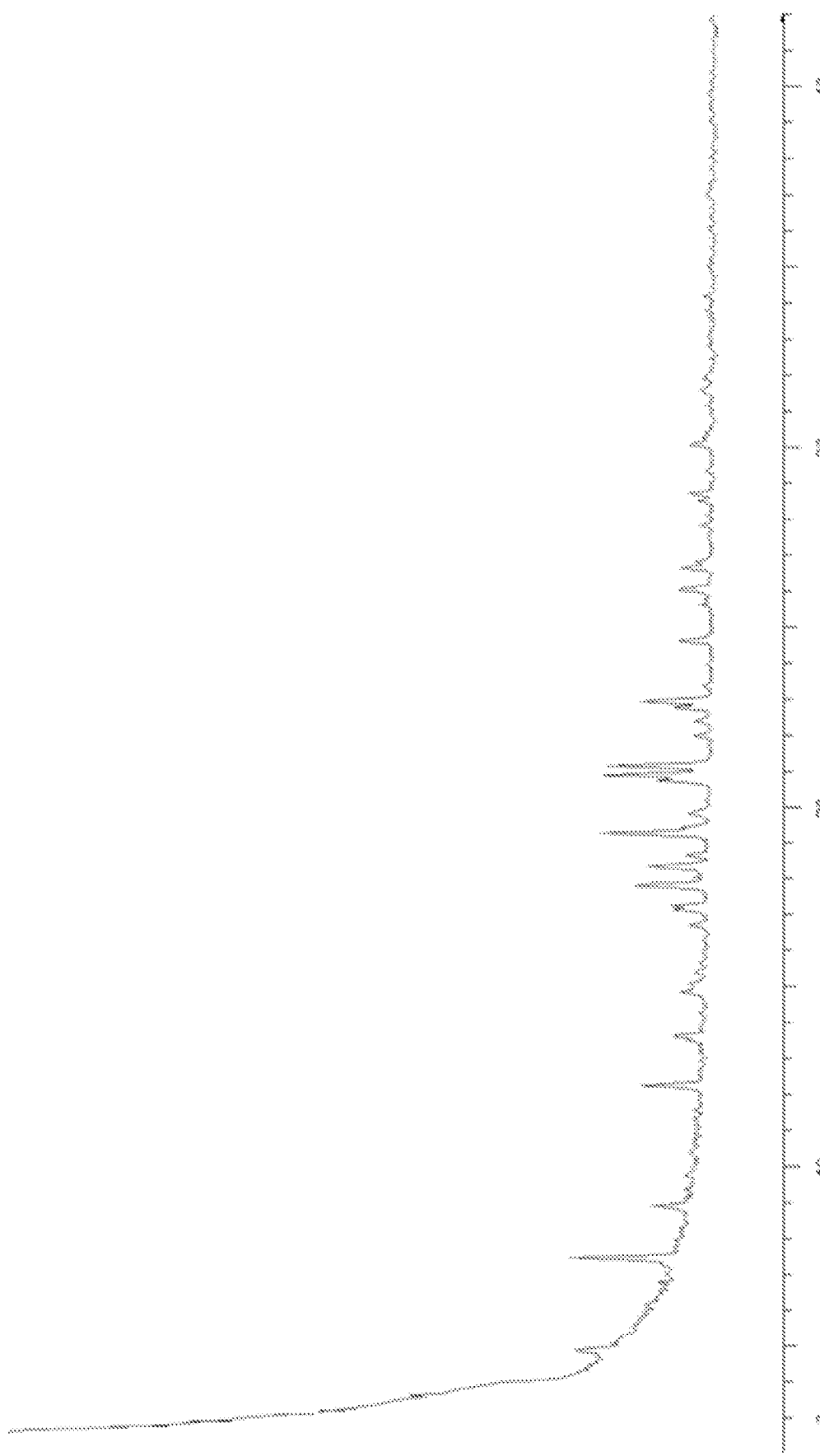
FIG. 24 illustrates a representative XRPD pattern for Pattern 12 of Compound II.
Figure 25:
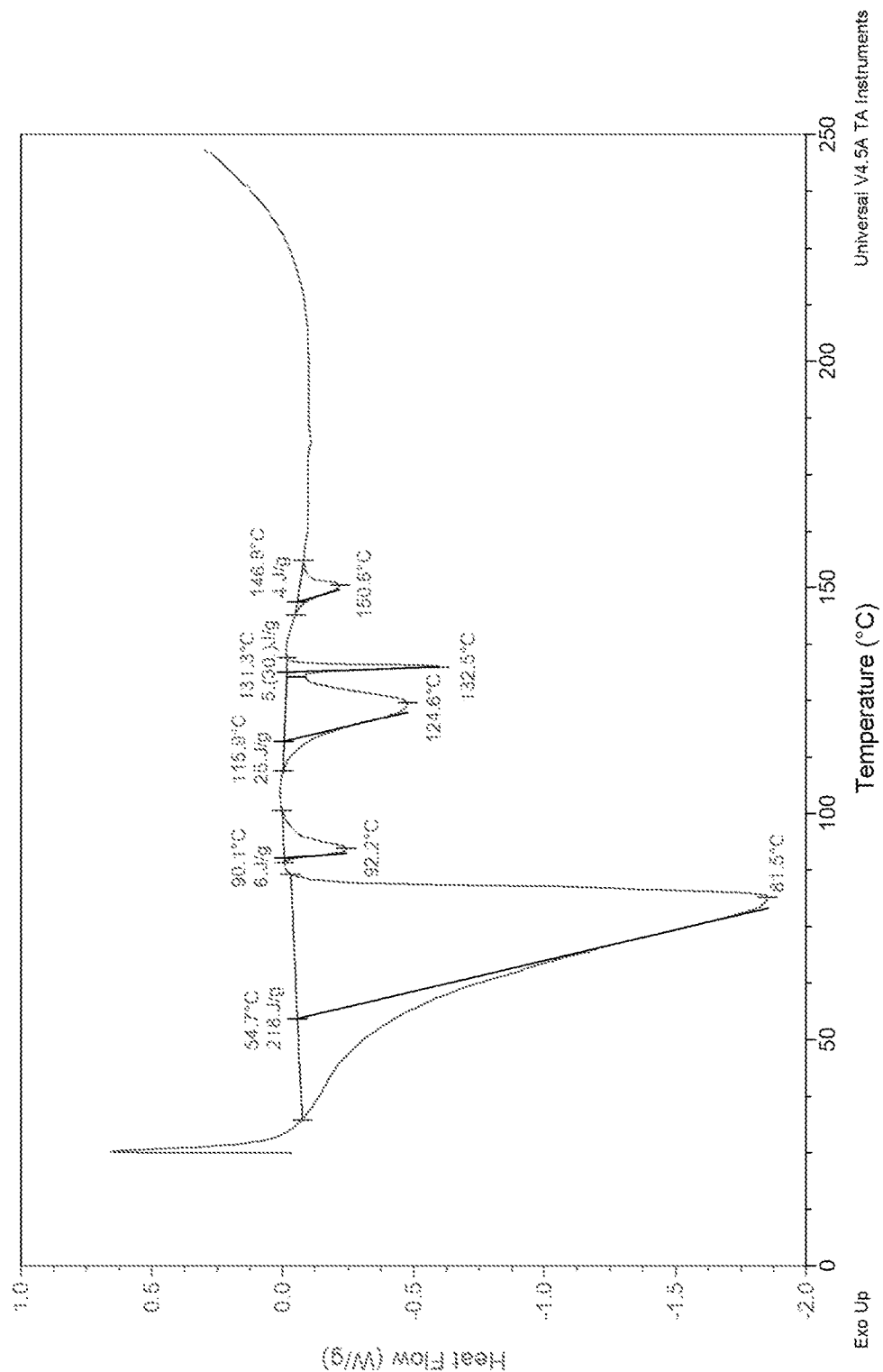
FIG. 25 illustrates a representative DSC thermogram for Pattern 12 of Compound II.

In some embodiments, provided herein is crystalline Compound II solvate Pattern 12. In some embodiments, crystalline Compound II Pattern 12 is characterized as having:
a) an XRPD pattern substantially the same as shown in FIG. 24;
b) a DSC thermogram substantially the same as shown in FIG. 25;
c) a DSC thermogram with five endothermic events having:
  i. an onset at about 54.7° C. and peak at about 81.5° C.;
  ii. an onset at about 90.1° C. and peak at about 92.2° C.;
  iii. an onset at about 115.9° C. and peak at about 124.6° C.;
  iv. an onset at about 131.3° C. and peak at about 132.5° C.; and
  v. an onset at about 146.8° C. and peak at about 150.6° C.;
or
d) combinations thereof.

In one aspect, described herein is a process for the preparation of sodium (E)-2-(4-((3-(4-fluorophenyl)-3-(4-(3-morpholinoprop-1-yn-1-yl)phenyl)allyl)oxy)-2-methylphenoxy)acetate (Compound II):

Compound II

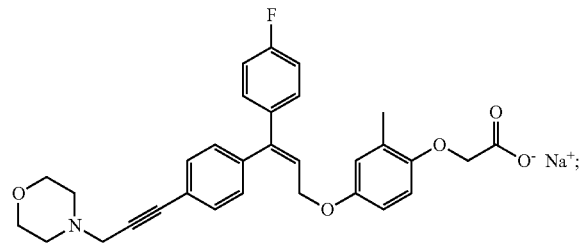

comprising treating:
Compound I:

Compound I

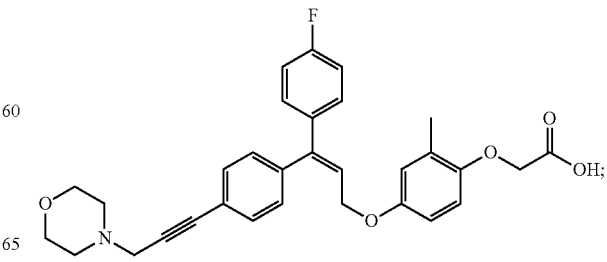

or the alkyl ester of Compound I, or a salt thereof:

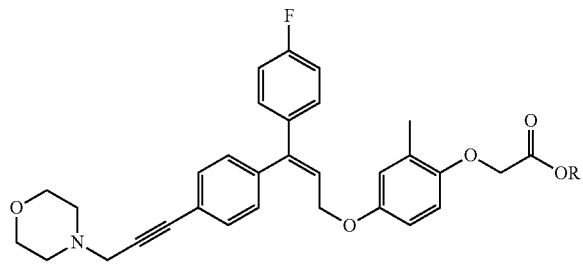

wherein R is $C_1$-$C_6$ alkyl;
   with a sodium hydroxide solution in the presence of a suitable solvent to provide Compound II.

In some embodiments, R is methyl, ethyl, propyl, isopropyl, butyl, isobutyl, tert-butyl, isoamyl, pentyl, or hexyl. In some embodiments, R is methyl or ethyl. In some embodiments, R is methyl. In some embodiments, R is ethyl.

In some embodiments, the suitable solvent is water, methanol, ethanol, tetrahydrofuran, ethyl acetate, acetone, acetonitrile, or a combination thereof.

In some embodiments, the preparation of the Compound II comprises treating Compound I with a sodium hydroxide solution in the presence of a suitable solvent, wherein the suitable solvent is water, methanol, ethanol, tetrahydrofuran, ethyl acetate, acetone, acetonitrile, or a combination thereof.

In some embodiments, the preparation of the Compound II comprises treating Compound I with a sodium hydroxide solution in the presence of a suitable solvent, wherein the suitable solvent is a combination of acetone and acetonitrile. In some embodiments, Compound II is Crystalline Form 1 as described herein.

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Ztrich:Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviors. Also, because the salt-forming molecule can be in equilibrium with a neutral form, passage through biological membranes can be adjusted.

In some embodiments, pharmaceutically acceptable salts are obtained by reacting a compound disclosed herein with an acid. In some embodiments, the compound disclosed herein (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (–L); malonic acid; mandelic acid (DL); methanesulfonic acid; naphthalene-1, 5-disulfonic acid; naphthalene-2-sulfonic acid; nicotinic acid; oleic acid; oxalic acid; palmitic acid; pamoic acid; phosphoric acid; proprionic acid; pyroglutamic acid (–L); salicylic acid; sebacic acid; stearic acid; succinic acid; sulfuric acid; tartaric acid (+L); thiocyanic acid; toluenesulfonic acid (p); and undecylenic acid.

In some embodiments, a compound disclosed herein is prepared as a hydrochloride salt.

In some embodiments, pharmaceutically acceptable salts are obtained by reacting a compound disclosed herein with a base. In some embodiments, the compound disclosed herein is acidic and is reacted with a base. In such situations, an acidic proton of the compound disclosed herein is replaced by a metal ion, e.g., lithium, sodium, potassium, magnesium, calcium, or an aluminum ion. In some cases, compounds described herein coordinate with an organic base, such as, but not limited to, ethanolamine, diethanolamine, triethanolamine, tromethamine, meglumine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt.

In some embodiments, a compound disclosed herein is prepared as the sodium salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

In additional or further embodiments, the compounds described herein are metabolized upon administration to an organism in need to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulfhydryl groups.

Metabolites of the compounds disclosed herein are optionally identified either by administration of compounds to a host and analysis of tissue samples from the host, or by incubation of compounds with hepatic cells in vitro and analysis of the resulting compounds.

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used herein, "alkyl" refers to an aliphatic hydrocarbon group. The alkyl group is branched or straight chain. In some embodiments, the "alkyl" group has 1 to 10 carbon atoms, i.e. a $C_1$-$C_{10}$alkyl. In some embodiments, an alkyl is a $C_1$-$C_6$alkyl. In one aspect the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, tert-butyl, isoamyl, pentyl, and hexyl.

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an agonist.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound disclosed herein, or a pharmaceutically acceptable salt thereof, and a co-agent, are both administered to a patient simultaneously in the form of a single entity or dosage. The term "non-fixed combination" means that the active ingredients, e.g. a compound disclosed herein, or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "article of manufacture" and "kit" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions

In some embodiments, the compounds and solid state forms described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins1999), herein incorporated by reference for such disclosure.

In some embodiments, the compounds and solid state forms described herein are administered either alone or in combination with pharmaceutically acceptable carriers, excipients or diluents, in a pharmaceutical composition. Administration of the compounds and compositions described herein can be effected by any method that enables delivery of the compounds to the site of action.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

It should be understood that in addition to the ingredients particularly mentioned above, the compounds and compositions described herein may include other agents conventional in the art having regard to the type of formulation in question, for example those suitable for oral administration may include flavoring agents.

Methods of Dosing and Treatment Regimens

In one embodiment, the compounds and solid state forms disclosed herein, or a pharmaceutically acceptable salt thereof, are used in the preparation of medicaments for the treatment of diseases or conditions in a mammal that would benefit from modulation of PPARS activity. Methods for treating any of the diseases or conditions described herein in a mammal in need of such treatment, involves administration of pharmaceutical compositions that include at least one compound disclosed herein or a pharmaceutically acceptable salt, active metabolite, prodrug, or pharmaceutically acceptable solvate thereof, in therapeutically effective amounts to said mammal.

In certain embodiments, the compositions containing the compounds and solid state forms described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-2000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound and solid state forms disclosed herein, or a pharmaceutically acceptable salt thereof, described herein are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

In any of the aforementioned aspects are further embodiments in which the effective amount of the compound disclosed herein, or a pharmaceutically acceptable salt thereof, is: (a) systemically administered to the mammal; and/or (b) administered orally to the mammal.

In some embodiments, compound II, a solid state form thereof, or a pharmaceutically acceptable salt thereof, is administered is dose selected from about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, and about 400 mg. In some embodiments, the dose is administered once a day. In some embodiments, the dose is administered twice a day.

Articles of Manufacture and Kits

Disclosed herein, in certain embodiments, are kits and articles of manufacture for use with one or more methods described herein. In some embodiments, additional components of the kit comprises a carrier, package, or container that is compartmentalized to receive one or more containers such as vials, tubes, and the like, each of the container(s) comprising one of the separate elements to be used in a method described herein. Suitable containers include, for example, bottles, vials, plates, syringes, and test tubes. In one embodiment, the containers are formed from a variety of materials such as glass or plastic.

The articles of manufacture provided herein contain packaging materials. Examples of pharmaceutical packaging materials include, but are not limited to, bottles, tubes, bags, containers, and any packaging material suitable for a selected formulation and intended mode of use.

For example, the container(s) include one or more of the compounds described herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

EXAMPLES

| Abbreviations: | | |
|---|---|---|
| 2-Me-THF or 2-MeTHF | = | 2-methyltetrahydrofuran; |
| ACN or MeCN | = | acetonitrile; |
| Compound I | = | (E)-2-(4-((3-(4-fluorophenyl)-3-(4-(3-morpholinoprop-1-yn-1-yl)phenyl)allyl)oxy)-2-methylphenoxy)acetic acid |
| Compound II | = | sodium (E)-2-(4-((3-(4-fluorophenyl)-3-(4-(3-morpholinoprop-1-yn-1-yl)phenyl)allyl)oxy)-2-methylphenoxy)acetate |
| CPME | = | cyclopropyl methyl ether; |
| DCM | = | dichloromethane; |
| DI | = | dionized; |
| DSC | = | differential scanning calorimetry; |
| EtOAc | = | ethyl acetate; |
| EtOH | = | ethanol; |
| equiv or eq. | = | equivalent(s); |
| FTIR or FT-IR | = | Fourier transform infrared; |
| g | = | gram(s); |

| Abbreviations: | | |
|---|---|---|
| GC-MS or GCMS or GC/MS | = | gas chromatography-mass spectrometry; |
| GVS | = | gravimetric vapor sorption; |
| h or hr | = | hour; |
| hrs | = | hours; |
| HPLC | = | high-performance liquid chromatography; |
| IC | = | ion chromatography; |
| IPA | = | isopropyl alcohol; |
| IPAc | = | isopropyl acetate; |
| KF | = | Karl Fisher titration; |
| kg or KG or Kg | = | kilogram(s); |
| L | = | liter; |
| LAG | = | liquid assisted grinding; |
| LC-MS or LCMS or LC/MS | = | liquid chromatography-mass spectrometry; |
| M | = | molar; |
| MEK | = | methyl ethyl ketone; |
| MIBK | = | methyl isobutyl ketone; |
| MeOAc | = | methyl acetate; |
| MeOH | = | methanol; |
| mg | = | milligram(s); |
| mins or mm | = | minutes; |
| mol. | = | mole; |
| mL or ml | = | milliliter; |
| µL | = | microliter; |
| MTBE or TBME | = | tert-butyl methyl ether; |
| NMP | = | N-methyl-2-pyrrolidone; |
| PPAR-delta or PPARδ | = | peroxisome proliferator-activated receptor delta; |
| ppm | = | parts per million; |
| rbf or RBF | = | round bottom flask; |
| RH | = | relative humidity; |
| Rpm | = | revolutions per minute; |
| rt or RT | = | room temperature; |
| Rt | = | retention time; |
| TFA | = | trifluoroacetic acid; |
| TGA | = | thermogravimetric analysis; |
| THF | = | tetrahydrofuran; |
| vol or vols | = | volume(s); |
| w/w | = | weight ratio; and |
| XRPD | = | X-ray powder diffraction. |

The following examples are provided for illustrative purposes only and not to limit the scope of the claims provided herein.

Example 1: Preparation of (E)-2-(4-((3-(4-fluorophenyl)-3-(4-(3-morpholinoprop-1-yn-1-yl)phenyl)allyl)oxy)-2-methylphenoxy)acetic acid (Compound I)

The preparation of Compound I has been previously described (see, WO 2007/071766, U.S. Pat. Nos. 7,943,613, 8,362,016, 8,551,993, 9,663,481, 9,855,274, WO 2015/035171, U.S. Pat. Nos. 9,487,493, 9,968,613, each of which is incorporated by reference in its entirety).

Example 2: Preparation of Sodium (E)-2-(4-((3-(4-fluorophenyl)-3-(4-(3-morpholinoprop-1-yn-1-yl)phenyl)allyl)oxy)-2-methylphenoxy)acetate (Compound II)

To a 72 L open head round bottom flask containing a solution of compound I (1089.4 g, 2.113 mol) in ethyl acetate (43 L) was added a solution of sodium hydroxide (82.0 g, 2.050 mol) in water (675 ml). The solution was heated to 40° C. and was filtered. The filtrates were concentrated under reduced pressure at 40° C. until 35 L of solvent were removed. The solution was stirred at 20° C. for 1 hr and was filtered. The filter cake was washed with ethyl acetate (4 L) and air-dried on the filter for 24 hrs followed by drying in a vacuum oven at 50° C. for 36 hrs to afford 1079.6 g of a beige solid. This solid was suspended in ethanol (22 L) in a 72 L rbf. The solution was stirred 3 hrs at room temp and then was filtered. The filter cake was air-dried 2 hrs and then was slurried with ethanol (2×4 L) followed by filtration. The filter cake was air-dried 24 hrs and then transferred to a vacuum oven at 50° C. for 24 hrs to afford Compound II (937.2 g. 82.5%) as a beige solid. This reaction was run twice in this manner to yield: 905.7 g (Sample #1, HPLC=99.85%, KF=0.65%, Acetic acid=19 ppm) and 968.7 g (Sample #2, HPLC=99.87%, KF=0.53%, Acetic acid=44 ppm). Total=1874.4 g (82.5% yield).

The two samples above were blended in a rotovap flask at room temperature for 1 hr to yield 1859.0 g of Compound II. The XRPD analysis of the collected solid was consistent with Compound II, Form 1. $^1$H-NMR was consistent with the structure.

Example 2-1: Preparation of Form 1 of Compound II

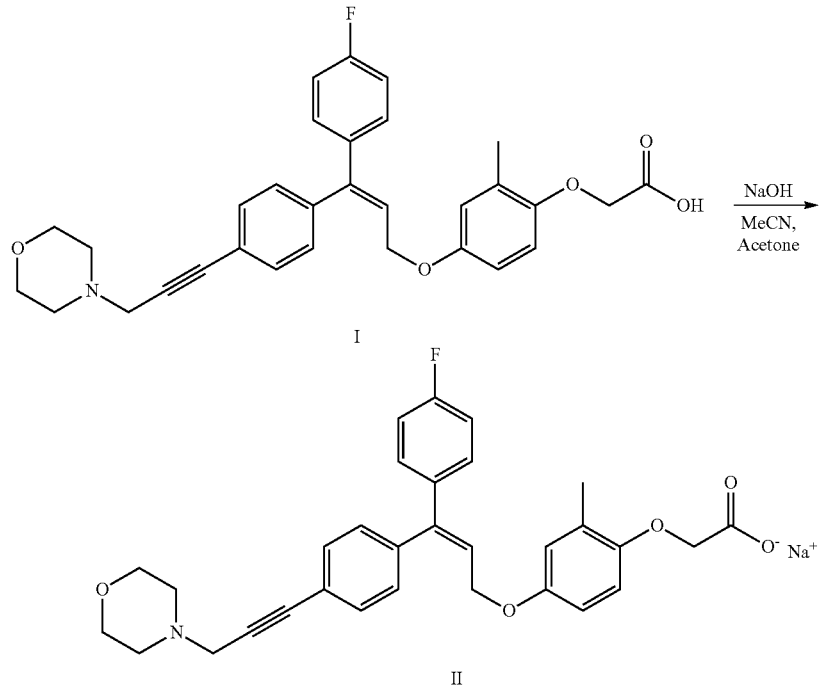

A solution of NaOH (1.1 eq) in water (1 ml/g) was added to Compound I in acetone (9 ml/g) at 50° C. and the mixture was stirred for 1-3 h to obtain a solution which was polish filtered. This solution was added to acetonitrile (12.5 ml/g), which was seeded with 4.2% w/w of Compound II (Form 1), at 35° C. over no less than 1.5 h. The resulting slurry was stirred at 35° C. for 1-3 h, cooled to 5° C., filtered under $N_2$, and twice washed with 2 ml/g cold acetone under a stream of $N_2$. The product was then dried at 45-55° C. for 15-20 h. $^1$H-NMR (300 MHz, 1:1 CDCl$_3$/DMSO-d6): δ 7.45 (d, 2H), 7.22 (m, 2H), 7.15 (d, 2H), 7.04 (m, 2H), 6.65 (d, 1H), 6.59 (d, 1H), 6.50 (dd, 1H), 6.24 (t, 1H), 4.44 (d, 2H), 4.18 (s, 2H), 3.67 (m, 4H), 3.50 (s, 2H), 2.57 (m, 4H), 2.16 (s, 3H). The XRPD analysis of the collected solid was consistent with Compound II, Form 1.

Example 3: Preparation of Amorphous Compound II from Crystalline Form 1 of Compound II Crystalline Form 1 of Compound II (500 mg) was dissolved in tBuOH/H$_2$O (1:1; 5.0 mL, 10 vol) at RT and filtered through a 0.45 m syringe tip filter and transferred to a clean 100 ml RBF. The solution was frozen in a cardice-acetone bath and dried under vacuum overnight. The resulting solid was analyzed by XRPD, $^1$H-NMR, DSC, TGA, KF and HPLC. Data was consistent with the amorphous material.

One sample was retained for analysis whilst additional samples were used as input to further polymorph screening.

Example 4: Preparation of Crystalline Hydrate Form 2 of Compound II from Crystalline Form 1 of Compound II Crystalline Form 1 of Compound II (4 g) was placed in a crystallization dish and stored in a stability chamber at 25° C./97% RH. XRPD analysis was regularly performed to verify the conversion to Form 2. Complete conversion was observed after 4 weeks at 25° C./97% RH.

The XRPD pattern was consistent with Form 2. The $^1$H-NMR spectrum was consistent with the proposed structure.

Example 5: Preparation of Crystalline Acetone Solvate Form 5 of Compound II from Crystalline Form 1 of Compound II Crystalline Form 1 of Compound II (25 mg) was weighed into HPLC vials and solvent was added (500 μl). The suspensions were stirred for 1 hr at 35° C. before being analyzed by XRPD. For XRPD analysis, two drops of suspension were pipetted onto the sample holder using the 4-minute method.

Results of the solvent screen are found in the following table:

| Solvent | XRPD |
|---|---|
| Acetone | initially Form 5; reverts to Form 1 |
| ACN | Form 1 |
| Acetone: ACN (1:1) | initially Form 5; reverts to Form 1 |
| Acetone: Water (99:1) | initially Form 5; reverts to Form 1 |
| ACN: Water (99:1) | Form 1 |
| Acetone: ACN: Water (49.5:49.5:1) | initially Form 5; reverts to Form 1 |

The XRPD performed on the aliquots recovered from the solvent mixtures showed that aliquots analyzed from acetone, acetone:acetonitrile, acetone:water and acetone:acetonitrile:water presented Form 5 initially but converted to Form 1 by the end of the run. The XRPD performed on the aliquots recovered from acetonitrile and acetonitrile:water showed the material remained as Form 1.

These additional experiments on Form 1 indicate that Form 5 is an acetone solvate as it was only observed from acetone and acetone solvent mixtures. Slurries in acetonitrile showed that Form 1 remained unchanged. Moreover, it was found that the conversion of Form 5 to Form 1 is reversible under these conditions and that Form 5 is the most stable form in acetone solvent systems. Form 5 proved difficult to isolate and fully characterize.

Example 6: Preparation of Crystalline Tetrahydrofuran Solvate Form 4 of Compound II from Crystalline Form 1 of Compound II Crystalline Form 1 of Compound 11(499.3 mg) was weighed into a 100 ml RBF with stir bar and THF (5 mL, 10 vol) was added at 60° C. The sample was allowed to stir (500 rpm) for 24 h after which time an aliquot was taken and analyzed by XRPD, showing Form 4 to have been produced. The material was then isolated using a Buchner funnel and left to dry under suction vacuum for about 45 mins. The sample was produced with a 70.8% yield, showed Form 4 by XRPD, and the $^1$H-NMR spectrum was consistent with the structure, showing 1.1 mol eq of THF.

Example 7: Preparation of Crystalline Pattern 9 of Compound II from Crystalline Form 2 of Compound II Crystalline Hydrate Form 2 of Compound II was portioned into two and half was placed in the vacuum oven at RT. After 24 h the sample was analyzed by XRPD. Some small differences between the XRPD pattern and the Form 2 reference were noted. After 4 days in the vacuum oven complete conversion was observed. The material showed Pattern 9 by XRPD and a purity of 99.7%. The $^1$H-NMR spectrum was consistent with the proposed structure and showed no residual solvent to be present.

Example 8: Polymorph Screen 1: Solvent Screen; Preparation of Additional Solid State Forms of Compound II Crystalline Form 1 of Compound II (20 mg) was added into HPLC vials with a stir bar. Each sample was treated with increasing amounts of solvent (100-200 μL, 5-10 vol) at 25° C. After each addition the sample was stirred for 20 min and observations recorded before further solvent additions. If complete dissolution was observed, no further additions of solvent were made. If dissolution was not observed in 100 vol solvent (2 mL), the temperature was raised to 40° C. and held for 30 min to encourage dissolution. Clear solutions obtained were placed in the fridge (5° C.) and suspensions were matured (40° C./5° C., 8 h/cycle) for 24 h. After 24 hours an aliquot was taken (filtered and dried under suction) and analyzed by XRPD.

Maturation and subsequent XRPD analysis of the suspensions showed either poorly crystalline materials or XRPD patterns which matched or were similar to Form 1. A single sample, 2-methyltetrahydrofuran, showed significant enough differences to Form 1 for a new crystalline form to be acknowledged. This was denoted as Form 3 and displayed an absence of several Form 1 peaks at low 2θ values, as well as some peak shifts at higher 2θ angles.

All remaining material (suspensions or solutions) was placed for evaporation to encourage solid formation.

The evaporation of all the samples resulted in solids which displayed either Form 1, either with or without some small additional peaks, or predominantly amorphous samples by XRPD. Two samples, 1,4-dioxane and tetrahydrofuran, displayed a new pattern by XRPD, denoted as Form 4.

Example 9: Polymorph Screen 2: Low Temperature Slurry; Preparation of Additional Solid State Forms of Compound II Amorphous Compound II was slurried in a selection of solvents (5, 10 or 20 vol as appropriate to maintain adequate stirring) at 5° C. for 24 h. The slurries were then analyzed by XRPD.

After 24 h at 5° C. a number of samples showed differences by XRPD; five samples (methyl isobutyl ketone, 1,4-dioxane, chloroform, tetrahydrofuran, and dichloromethane) displayed Form 4, with varying levels of crystallinity and a single sample (diethyl ether) showed a new pattern, similar to a combination of Form 1 and Form 4 and was denoted as Form 5. A number of samples were poorly crystalline and a pattern not able to be identified, and the remainder of the samples displayed Form 1 with varying degrees of crystallinity.

The slurries were left stirring at 5° C. and analyzed again after 4 days.

After an extended period (4 days) at 5° C. the XPRD analysis results were similar, with a few samples displaying an increased level of crystallinity. Two samples showed a change relative to the 24 h data: 2-methyltetrahydrofuran showed a more crystalline pattern than seen after 24 h, which was denoted as Pattern 5, and EtOAc/H$_2$O (97.3:2.7) showed a poorly crystalline material with some differences with respect to the known patterns.

Example 10: Polymorph Screen 3: Liquid Assisted Grinding; Preparation of Additional Solid State Forms of Compound II To the Amorphous Compound II, two small ball bearings were added along with the appropriate solvent (5 μL). The samples were subjected to mechanical stress using a Fritsch Planetary Mill (500 rpm, 2 h) and N-Methyl-2-Pyrrolidone the recovered materials analyzed by XRPD.

A number of samples (total of 10) remained amorphous or predominantly amorphous with a single small peak between 2.8-3.0° 2θ, after the grinding. Two samples, sample 14 (1,4-dioxane) and sample 16 (chloroform) solvents respectively, displayed Form 4 by XRPD. A further four samples also displayed differences by XRPD: samples 15 (toluene), 4 (methyl isobutyl ketone), 19 (2-methyltetrahydrofuran) and 24 (N-methyl-2-pyrrolidone). The latter three were identified as Form 3. The XRPD pattern obtained from sample 15 was denoted as Form 3. The remainder of the samples converted to Form 1 during the grinding.

Example 11: Polymorph Screen 4: High Temperature Slurry; Additional Solid State Forms of Compound II Appropriate solvent was added to Amorphous Compound II (300 µL, 10 vol/150 µL, 5 vol) and slurried for 24 h at 60° C. Where necessary the samples were left at either 50° C. or RT to slurry (solvent dependent).

The slurry samples were analyzed after 24 h and showed predominantly Form 1 by XRPD, with varying degrees of crystallinity. Five samples, however, showed differences by XRPD: sample obtained from methyl isobutyl ketone was assigned as Form 3, sample obtained from methyl ethyl ketone was assigned as Form 5, sample obtained from 1,4-dioxane was assigned as pattern 6, sample obtained from tetrahydrofuran was assigned as Form 4, and sample obtained from 2-methyltetrahydrofuran was assigned as pattern 5 (poorly crystalline).

Example 12: Preparation of Crystalline Ethyl Acetate Solvate Pattern 8 of Compound II from Amorphous Compound II EtOAc/H$_2$O (97.3:2.7; 300 µL, 10 vol) was added to amorphous Compound II and placed in the fridge under stirring. A portion was taken and analyzed by XRPD after 24 h, and the slurry left stirring at 4° C. The sample was further analyzed after 48 h and 6 days.

At all time-points analyzed, the same pattern was observed by XRPD, however this was different to that targeted in this experiment. The new pattern was denoted as Pattern 8.

Example 13: Preparation of Crystalline 2-Methyltetrahydrofuran Solvate Form 3 of Compound II from Crystalline Form 1 of Compound II Crystalline Form 1 of Compound II (506.8 mg) was weighed into a 100 ml RBF with stirrer bar and 2-methyltetrahydrofuran solvent (5 µL, 10 vol) added at 60° C. The sample was left to stir (500 rpm) for 3 days total, with an aliquot taken after 24 h and analyzed by XRPD. This showed that Pattern 5 had not been obtained and the sample was left for a prolonged duration.

After a further 2 days a second aliquot was taken and XPRD analysis indicated Form 3 to have formed. Additional 2-methyltetrahydrofuran (5 µL, 10 vol) was added and the sample cooled to 5° C. and left to stir over the weekend. The sample was filtered using a Buchner funnel and dried under suction vacuum for 15 min.

The aliquots of the attempted scale up of Pattern 5 analyzed by XRPD displayed Form 3 during the preparation at high temperature. Upon cooling, the sample also displayed From 3. This XRPD pattern persisted upon isolation. The sample was prepared with a yield of 84%. The $^1$H-NMR spectrum was consistent with the proposed structure and indicated 0.17 mol eq residual 2-methyltetrahydrofuran to be present.

Example 14: Thermodynamic Stability and Preparation of Crystalline Pattern 12 of Compound II Competitive slurries aiming to determine the order of stability between Form 1 and Form 2 were performed in a range of water activities (0.4-0.8).

Crystalline Form 1 (2 g) and Crystalline Hydrate Form 2 (2 g) were lightly ground together using a mortar and pestle and then mixed using a roller mixer for approximately 2 hours. An XRPD was collected on this sample.

Saturated solutions at 5° C./25° C. were prepared by suspending the mixed sample (200 mg) in 4 ml of the selected solvent and saturated solutions were prepared at 50° C. by suspending the mixed sample (100 mg) in 1 ml of the selected solvent. The saturated solutions were left stirring for 3 hrs at 25° C. and 50° C. The saturated solutions at 25° C. were filtered and split into solutions at 5° C. and 25° C. The mixed sample (50 mg) was added to the filtered solutions. Two control samples of Form 2 (50 mg) were prepared in 1 ml of acetone:water (99:1) and EtOH:water (95:5) and left stirring at 5° C., 25° C. and 50° C.

The samples were monitored at three different temperatures in a range of different water activities. Form 1 was present in most cases with no evidence of Form 2. From acetone and acetone:water (99:1) only Form 1 was observed. Form 5 peaks were observed in mixture with Form 1 for the slurry in EtOAc:Water (99:1). Form 4 was observed from the samples analyzed from THF:Water (98:2). Only Form 1 was observed from EtOH:Water (95:5) and IPA:Water (94:6).

Finally, a new pattern was identified from ACN:Water (93:7), denoted as Pattern 12. The material was later isolated by filtration and re-analyzed by XRPD. The sample maintained the same XRPD pattern, Pattern 12.

Example 15. X-Ray Powder Diffraction (XRPD)

XX.1 Bruker AXS C2 GADDS

XRPD diffractograms were collected on a Bruker AXS C2 GADDS diffractometer using Cu Kα radiation (40 kV, 40 mA), an automated XYZ stage, a laser video microscope for auto-sample positioning and a Våntec-500 2-dimensional area detector. X-ray optics consists of a single Göbel multilayer mirror coupled with a pinhole collimator of 0.3 mm.

The beam divergence, i.e. the effective size of the X-ray beam on the sample, was approximately 4 mm. A θ-θ continuous scan mode was employed with a sample—detector distance of 20 cm which gives an effective 2θ range of 1.5°-32.5°. Typically, the sample was exposed to the X-ray beam for 120 seconds. The software used for data collection and analysis was GADDS for Win7/XP and Diffrac Plus EVA respectively.

Samples run under ambient conditions (post VAC-XRPD) were analyzed as prepared for the vacuum experiment, using the sample retained within the Anton Parr metal recessed holder.

XX 2 Bruker AXS D8 Advance

XRPD diffractograms were collected on a Bruker D8 diffractometer using Cu Kα radiation (40 kV, 40 mA) and a 0-2θ goniometer fitted with a Ge monochromator. The incident beam passes through a 2.0 mm divergence slit followed by a 0.2 mm antiscatter slit and knife edge. The diffracted beam passes through an 8.0 mm receiving slit with 2.5° Soller slits followed by the Lynxeye Detector. The software used for data collection and analysis was Diffrac Plus XRD Commander and Diffrac Plus EVA respectively.

Samples were run under ambient conditions as flat plate specimens. The sample was prepared on a polished, zero-background (510) silicon wafer by gently pressing onto the flat surface or packed into a cut cavity. The sample was rotated in its own plane.

The details of the standard Pharmorphix data collection method are:

Angular range: 2 to 42° 2θ
Step size: 0.05° 2θ
Collection time: 0.5 s/step (total collection time: 6.40 min)

XX.3 PANalytical Empyrean

XRPD diffractograms were collected on a PANalytical Empyrean diffractometer using Cu Kα radiation (45 kV, 40 mA) in transmission geometry. A 0.5° slit, 4 mm mask and 0.04 rad Soller slits with a focusing mirror were used on the incident beam. A PIXcel3D detector, placed on the diffracted beam, was fitted with a receiving slit and 0.04 rad Soller slits. The software used for data collection was X'Pert Data Collector using X'Pert Operator Interface. The data were analyzed and presented using Diffrac Plus EVA or HighScore Plus.

Samples were prepared and analyzed in either a metal or Millipore 96 well-plate in transmission mode. X-ray transparent film was used between the metal sheets on the metal well-plate and powders (approximately 1-2 mg) were used as received. The Millipore plate was used to isolate and analyze solids from suspensions by adding a small amount of suspension directly to the plate before filtration under a light vacuum.

The scan mode for the metal plate used the gonio scan axis, whereas a 2θ scan was utilized for the Millipore plate.

The details of the standard screening data collection method are:

Angular range: 2.5 to 32.0° 2θ
Step size: 0.0130° 2θ
Collection time: 12.75 s/step (total collection time of 2.07 min)

Non-Ambient Conditions

XRPD diffractograms were collected on a PANalytical Empyrean diffractometer using Cu Kα radiation (45 kV, 40 mA) in reflection geometry. The instrument is fitted with an Anton Paar CHC plus+ stage fitted with graphite/Kapton windows and equipped with air cooling/and coupled with a proUmid MHG32 Modular Humidity Generator, or a low vacuum pump system using an Edwards RV3 pump. A programmable divergence slit (in automatic mode), with a 10 mm fixed incident beam mask, Ni filter and 0.04 rad Soller slits were used on the incident beam. A PIXcel3D detector, placed on the diffracted beam, was fitted with a programmable antiscatter slit (in automatic mode) and 0.04 rad Soller slits.

The software used for data collection was X'Pert Data Collector and the data analyzed and presented using Diffrac Plus EVA or Highscore Plus.

For vacuum (VAC-XRPD) experiments the sample was prepared and analyzed in an Anton Paar chromed sample holder. A reference XPRD pattern was collected before applying the vacuum. Measurements were taken every 5 min for 1.5 h then at 20 min intervals for 2 h, followed by hourly sampling for 3 h. The sample was left under vacuum for 72 h, a final measurement taken and then the vacuum released. Further measurement (post vac) were collected every 10 mins for 3 h, exposing the sample to ambient conditions. The measurement parameters are as per the standard screening data collection method (detailed above).

For variable temperature (VT-XRPD) experiments the samples were prepared and analyzed in an Anton Paar chromed sample holder. A heating/cooling rate of 10° C./min was used with a 2 min isothermal hold before the measurement started. The measurement parameters are as per the standard screening data collection method (detailed above). Measurements were taken at the following temperatures:

| Target Temperature (° C.) |
| --- |
| 25 |
| 75 |
| 80 |
| 90 |
| 100 |
| 110 |
| 120 |
| 130 |
| 140 |
| 145 |
| 25 |

For variable humidity (VH-XRPD, Form 1) experiments the sample was prepared and analyzed in an Anton Paar chromed sample holder. The measurement parameters are as per the standard screening data collection method (detailed above). Measurements were taken at the following humidities:

| Target RH/% | Hold Duration |
| --- | --- |
| 40 | 1 h |
| 60 | 1 h |
| 80 | 1 h |
| 90 | 12.5 h |
| 80 | 2 h |
| 60 | 2 h |
| 40 | 2 h |
| 20 | 2 h |
| 10 | 12.5 h |
| 20 | 2 h |
| 40 | 2 h |

Data collection occurs at start and end of each section, with 1 h sampling interval.

Characterization of Solid State Forms and Patterns of Compound II

The X-Ray powder diffraction pattern for crystalline Form 1 of Compound II is displayed in FIG. 1. The X-Ray powder diffraction pattern for crystalline hydrate Form 2 of Compound II is displayed in FIG. 6. The X-Ray powder diffraction pattern for crystalline 2-methyltetrahydrofuran solvate Form 3 of Compound II is displayed in FIG. 9. The X-Ray powder diffraction pattern for crystalline tetrahydrofuran solvate Form 4 of Compound II is displayed in FIG. 12. The X-Ray powder diffraction pattern for crystalline acetone solvate Form 5 of Compound II is displayed in FIG. 15. The X-Ray powder diffraction pattern for crystalline hydrate Pattern 9 of Compound II is displayed in FIG. 18. The X-Ray powder diffraction pattern for amorphous Compound II is displayed in FIG. 21. The X-Ray powder diffraction pattern for pattern 12 of Compound II is displayed in FIG. 24.

Characterization of Crystalline Form 1 of Compound II

The X-Ray powder diffraction pattern for crystalline Form 1 of Compound II is displayed in FIG. 1. Characteristic peaks include the peaks listed in the following table:

| Angle 2-Theta (°) | Rel. Intensity (%) |
|---|---|
| 2.8 | 100.0 |
| 6.7 | 17.0 |
| 7.2 | 22.6 |
| 13.4 | 24.2 |
| 17.8 | 23.5 |
| 19.7 | 24.6 |
| 19.9 | 25.6 |
| 20.6 | 22.9 |
| 21.8 | 23.7 |

Characterization of Crystalline Hydrate Form 2 of Compound II

The X-Ray powder diffraction pattern for crystalline hydrate Form 2 of Compound II is displayed in FIG. 6. Characteristic peaks include the peaks listed in the following table:

| Angle 2-Theta (°) | Rel. Intensity (%) |
|---|---|
| 4.5 | 100.0 |
| 13.8 | 42.5 |
| 17.6 | 65.3 |
| 18.3 | 48.8 |
| 19.0 | 64.2 |
| 19.6 | 55.2 |
| 19.9 | 68.4 |
| 20.5 | 62.9 |
| 23.0 | 52.5 |

Characterization of the Crystalline Tetrahydrofuran Solvate Form 4 of Compound II The X-Ray powder diffraction pattern for crystalline tetrahydrofuran solvate Form 4 of Compound II is displayed in FIG. 12. Characteristic peaks include the peaks listed in the following table:

| Angle 2-Theta (°) | Rel. Intensity (%) |
|---|---|
| 3.3 | 100.0 |
| 5.7 | 16.3 |
| 11.9 | 14.4 |
| 19.8 | 15.2 |
| 20.1 | 42.4 |
| 20.7 | 23.2 |
| 22.9 | 17.1 |
| 23.1 | 15.6 |

Crystalline tetrahydrofuran solvate Form 4 of sodium (E)-2-(4-((3-(4-fluorophenyl)-3-(4-(3-morpholinoprop-1-yn-1-yl)phenyl)allyl)oxy)-2-methylphenoxy)acetate has an unchanged XRPD after heating to 110° C.

Characterization of Crystalline Acetone Solvate Form 5 of Compound II

The X-Ray powder diffraction pattern for crystalline acetone solvate Form 5 of Compound II is displayed in FIG. 15. Characteristic peaks include the peaks listed in the following table:

| Angle 2-Theta (°) | Rel. Intensity (%) |
|---|---|
| 2.8 | 100.0 |
| 8.3 | 15.4 |
| 8.7 | 11.3 |
| 13.1 | 16.1 |
| 19.4 | 21.9 |
| 20.2 | 12.2 |
| 21.3 | 16.6 |
| 24.6 | 14.6 |

Example 16: Differential Scanning Calorimetry (DSC)

XX.1 TA Instruments Q2000

DSC data were collected on a TA Instruments Q2000 equipped with a 50 position auto-sampler. Typically, 0.5-3 mg of each sample, in a pin-holed aluminum pan, was heated at 10° C./min from 25° C. to 275° C. A purge of dry nitrogen at 50 ml/min was maintained over the sample.

Modulated temperature DSC was carried out using an underlying heating rate of 2° C./min and temperature modulation parameters of 0.626° C. (amplitude) every 60 seconds (period).

The instrument control software was Advantage for Q Series and Thermal Advantage and the data were analyzed using Universal Analysis or TRIOS.

XX.2 TA Instruments Discovery DSC

DSC data were collected on a TA Instruments Discovery DSC equipped with a 50 position auto-sampler. Typically, 0.5-2 mg of each sample, in a pin-holed aluminum pan, was heated at 10° C./min from 25° C. to 280° C. A purge of dry nitrogen at 50 ml/min was maintained over the sample.

The instrument control software was TRIOS and the data were analyzed using TRIOS or Universal Analysis.

The DSC thermogram for crystalline Form 1 of Compound II is displayed in FIG. 2. The DSC thermogram for crystalline hydrate Form 2 of Compound II is displayed in FIG. 7. The DSC thermogram for crystalline 2-methyltetrahydrofuran solvate Form 3 of Compound II is displayed in FIG. 10. The DSC thermogram for crystalline tetrahydrofuran solvate Form 4 of Compound II is displayed in FIG. 13. The DSC thermogram for crystalline acetone solvate Form 5 of Compound II is displayed in FIG. 16. The DSC thermogram for crystalline hydrate Pattern 9 of Compound II is displayed in FIG. 19. The DSC thermogram for amorphous Compound II is displayed in FIG. 22. The DSC thermogram for crystalline Pattern 12 of Compound II is displayed in FIG. 25.

Differential Scanning Calorimetry (DSC) thermogram endotherms for selected forms and patterns are as described in the following table:

| Solid State Form | DSC Endotherms |
|---|---|
| amorphous | broad endotherm with onset at 43.1° C. and peak at about 60.3° C., broad exotherm with onset at 107.0° C. and peak at 112.9° C.; and endotherm with onset at 125.0° C. peak a 130.4° C. |
| Form 1 | onset at about 179.5° C. and peak at about 181.6° C. |
| Form 2 | six endothermic events: onset at about 44.1° C. and peak at about 72.4° C.; peak at about 92.4° C.; onset at about 107.0° C. and peak at about 118.5° C.; onset at about 127.6° C. and peak at about 130.0° C.; onset at about 146.9° C. and peak at about 149.9° C.; and onset at about 179.5° C. and peak at about 181.1° C. |
| Form 3 | three endothermic events: onset at about 58.7° C. and peak at about 73.2° C.; onset at about 114.5° C. and peak at about 136.2° C.; and onset at about 172.5° C. and peak at about 178.6° C. |

-continued

| Solid State Form | DSC Endotherms |
|---|---|
| Form 4 | two endothermic events: onset at about 111.7° C. and peak at about 114.5° C. with a broad shoulder starting at about 70° C.; and onset at about 142.5° C. and peak at about 147.2° C. with a broad shoulder starting at about 130.6° C. |
| Form 5 | two endothermic events having: an onset at 75.8° C. and two peaks at about 85.8° C. and 97.2° C.; and onset at 180.4° C. and a peak at 182.2 |
| Pattern 9 | three endothermic events: onset at about 38.5° C. and two peaks at about 71.5° C. and 94.1° C.; onset at about 107.1° C. and two peaks at about 118.0° C. and 130.0° C.; and onset at about 146.8° C. and peak at about 150.0° C. |
| Pattern 5 | four endothermic events: onset at about 50.7° C. and two peaks at about 54.6° C. and 60.1° C.; onset at about 125.4° C. and peak at about 130.4° C.; onset at about 142.7° C. and peak at about 146.2° C.; and onset at about 172.4° C. and peak at about 181.0° C. |
| Pattern 6 | three endothermic events: onset at about 88.0° C. and two peaks at about 97.7° C. and 105.5° C.; onset at about 120.3° C. and four peaks at about 125.1° C., 132.4° C., 134.7° C., and 144.2° C.; and onset at about 176.5° C. and peak at about 180.3° C. |
| Pattern 12 | five endothermic events: onset at about 54.7° C. and peak at about 81.5° C.; onset at about 90.1° C. and peak at about 92.2° C.; onset at about 115.9° C. and peak at about 124.6° C.; onset at about 131.3° C. and peak at about 132.5° C.; and onset at about 146.8° C. and peak at about 150.6° C. |

Example 17: Thermogravimetric Analysis (TGA)

XX.1 TA Instruments Q500

TGA data were collected on a TA Instruments Q500 TGA, equipped with a 16 position auto-sampler. Typically, 5-10 mg of each sample was loaded onto a pre-tared aluminum DSC pan and heated at 10° C./min from ambient temperature to 350° C. A nitrogen purge at 60 ml/min was maintained over the sample.

The instrument control software was Advantage for Q Series and Thermal Advantage and the data were analyzed using Universal Analysis.

The TGA pattern for crystalline Form 1 of Compound II is displayed in FIG. 3. The TGA pattern for crystalline hydrate Form 2 of Compound II is displayed in FIG. 8. The TGA pattern for crystalline 2-methyltetrahydrofuran solvate Form 3 of Compound II is displayed in FIG. 11. The TGA pattern for crystalline tetrahydrofuran solvate Form 4 of Compound II is displayed in FIG. 14. The TGA pattern for crystalline hydrate Pattern 9 of Compound II is displayed in FIG. 20. The TGA pattern for amorphous Compound II is displayed in FIG. 23.

Thermogravimetric Analysis (TGA) patterns for selected forms and patterns are as described in the following table:

| Solid State Form | TGA Pattern |
|---|---|
| amorphous | 3.7% w/w loss from 25 to 150° C., and a degradation onset at about 260° C. |
| Form 1 | 0.1% w/w loss from 25 to 60° C. and degradation onset at about 250° C. |
| Form 2 | 17.2% w/w loss from 25 to 145° C., and degradation onset at about 275° C. |
| Form 3 | 2.3 % w/w loss from 25 to 82° C., a further 3.8% w/w loss from 82° C. to 155° C., and a degradation onset at about 275° C. |
| Form 4 | 14.3 % w/w loss from 25 to 175° C., and degradation onset at about 285° C. |

-continued

| Solid State Form | TGA Pattern |
|---|---|
| Pattern 9 | 8.6 % w/w loss from 25 to 105° C., and degradation onset at about 270° C. |
| Pattern 5 | 1.0% w/w loss from 25 to 51° C., a further 7.6% w/w loss from 51 to 91° C., a further 4.7% w/w loss from 91° C. to 156° C., and a degradation onset at about 275° C. |
| Pattern 6 | 15.6% w/w loss from 25 to 187° C., and a degradation onset at about 260° C. |

Example 18: Gravimetric Vapor Sorption (GVS)

Sorption isotherms were obtained using a SMS DVS Intrinsic moisture sorption analyzer, controlled by DVS Intrinsic Control software. The sample temperature was maintained at 25° C. by the instrument controls. The humidity was controlled by mixing streams of dry and wet nitrogen, with a total flow rate of 200 ml/min. The relative humidity was measured by a calibrated Rotronic probe (dynamic range of 1.0-100% RH), located near the sample. The weight change, (mass relaxation) of the sample as a function of % RH was constantly monitored by a microbalance (accuracy ±0.005 mg).

Typically, 5-30 mg of sample was placed in a tared mesh stainless steel basket under ambient conditions. The sample was loaded and unloaded at 40% RH and 25° C. (typical room conditions). A moisture sorption isotherm was performed as outlined below (2 scans per complete cycle). The standard isotherm was performed at 25° C. at 10% RH intervals over a 0-90% RH range. Typically, a double cycle (4 scans) was carried out. Data analysis was carried out within Microsoft Excel using the DVS Analysis Suite.

The method for SMS DVS Intrinsic experiments is outlined in the following table:

| Parameter | Value |
|---|---|
| Adsorption - Scan 1 (% RH) | 40-90 |
| Desorption, Adsorption - Scan 2 (% RH) | 90-0, 0-40 |
| Intervals (% RH) | 10 |
| Number of Scans | 4 |
| Flow rate (mL/min) | 200 |
| Temperature (° C.) | 25 |
| Stability (° C./min) | 0.2 |
| Sorption Time (hours) | 6 hour time out |
| Number of cycles | 2 |

Reversible water uptake for the crystalline forms and patterns as determined by Gravimetric Vapor Sorption (GVS) are as described in the following table:

| Solid State Form | Reversible Water Uptake between 0-90% RH |
|---|---|
| Form 1 | ~13.0% † |
| Form 2 | ~25% |
| Form 4 | ~23% |
| Form 5 | ~11% |
| Pattern 9 | ~27% |
| Form 3 | ~9.0% |

† GVS data for Form 1 can vary from batch to batch of synthesis

The samples were recovered after completion of the isotherm experiment at 900% RH and 25° C. and re-analyzed by XRPD. Results of the subsequent XRPD analysis are described in the following table:

| Solid State Form Before GVS | Solid State Form After GVS |
|---|---|
| Form 1 | Unchanged (Form 1) |
| Form 2 | Unchanged (Form 2) |
| Form 4 | Form 2 |
| Form 5 | Form 1 |
| Pattern 9 | Unchanged (Pattern 9) |
| Form 3 | Form 1 |

Example 19: Stability of Solid State Forms

Samples were assessed for stability under ambient or static storage conditions of 25° C./97% RH and 40° C./75% RH for 7 or 10 days. The samples were then re-analyzed by XRPD.

Results of the subsequent XRPD analysis for the crystalline forms are described in the following table:

| Solid State Form | 25° C./97% RH/7 days | 40° C./75% RH/7 days |
|---|---|---|
| Form 1 | Form 2 | Unchanged (Form 1) |
| Form 2 | Unchanged (Form 2) | Unchanged (Form 2) |
| Form 4 | Form 2 | Form 1 |
| Pattern 9 | some changes: similar to pattern 9 and Form 2 | some changes: similar to pattern 9 and Form 2 |
| Form 3 | — | Form 1 |

There was no change in the XRPD of the amorphous solid form under ambient storage conditions for 24 hours, 48 hours, 7 days, or 10 days. There was no change in the XRPD of the amorphous solid form under static storage of 40° C./75% RH for 10 days.

Example 20: High-Performance Liquid Chromatography (HPLC) Methods

Purity analysis was performed on an Agilent HP1100 series system (or equivalent) equipped with a diode array detector and using ChemStation software. The full method details are provided below:

| 8 Minute Method | | |
|---|---|---|
| Parameter | Value | |
| Type of method | Reverse phase with gradient elution | |
| Sample Preparation | 0.25 mg/mL in acetonitrile:water 1:1 | |
| Column | Supelco Ascentis Express C18, 100 × 4.6 mm, 2.7 μm | |
| Column Temperature (° C.) | 25 | |
| Injection (μL) | 5 | |
| Wavelength, Bandwidth (nm) | 255, 90 | |
| Flow Rate (mL/min) | 2 | |
| Phase A | 0.1% TFA in water | |
| Phase B | 0.085% TFA in acetonitrile | |
| | Time (mm) | % Phase A | % Phase B |
| Timetable | 0 | 95 | 5 |
| | 6 | 5 | 95 |
| | 6.2 | 95 | 5 |
| | 8 | 95 | 5 |

| 30 Minute Method | | |
|---|---|---|
| Parameter | Value | |
| Type of method | Reverse phase with gradient elution | |
| Sample Preparation | 0.25 mg/mL in acetonitrile:water 1:1 | |
| Column | Supelco Ascentis Express C18, 100 × 4.6 mm, 2.7 μm | |
| Column Temperature (° C.) | 25 | |
| Injection (μL) | 5 | |
| Wavelength, Bandwidth (nm) | 255, 90 | |
| Flow Rate (mL/min) | 2 | |
| Phase A | 0.1% TFA in water | |
| Phase B | 0.085% TFA in acetonitrile | |
| | Time (min) | % Phase A | % Phase B |
| Timetable | 0 | 95 | 5 |
| | 25 | 5 | 95 |
| | 25.2 | 95 | 5 |
| | 30 | 95 | 5 |

| 50 Minute Method | | |
|---|---|---|
| Parameter | Value | |
| Type of method | Reverse phase with gradient elution | |
| Sample Preparation | 0.2 mg/mL in acetonitrile:water 1:1 | |
| Column | Hichrom RPB C18, 250 × 4.6 mm, 5 μm | |
| Column Temperature (° C.) | 35 | |
| Injection (μL) | 20 | |
| Wavelength, Bandwidth (nm): (detection) | 248 (4) | |
| Wavelength, Bandwidth (nm): (reference) | 400 (100) | |
| Flow Rate (mL/min) | 1.0 | |
| Aqueous buffer | 0.1M Ammonium Dihydrogen Phosphate, pH 2.5 | |
| Phase A | 60:40 (Aqueous buffer: ACN) | |
| Phase B | 30:70 (Aqueous buffer: ACN) | |
| | Time (min) | % Phase A | % Phase B |
| Timetable | 0.0 | 100.0 | 0.0 |
| | 10.0 | 100.0 | 0.0 |
| | 27.0 | 66.5 | 33.5 |
| | 39.0 | 0.0 | 100.0 |
| | 40.0 | 100.0 | 0.0 |
| | 50.0 | 100.0 | 0.0 |

Purity analysis of the different solid state forms indicated >9900 purity of all forms. HPLC purity values are detailed in the table below:

| Solid State Form | HPLC Purity |
|---|---|
| amorphous | 99.5% (50 min method) |
| Form 1 | 99.6% (50 min method) |
| Form 2 | 99.3% (8 min method) |
| Form 3 | 99.5% (8 min method) |
| Form 4 | 99.6% (8 min method) |
| Pattern 9 | 99.7% (8 min method) |
| Pattern 5 | 99.6% (8 min method) |
| Pattern 6 | 99.1% (8 min method) |

Example 21: Karl Fisher (KF) Titration

The water content of each sample was measured on a Metrohm 874 Oven Sample Processor up to 150° C. with 851 Titrano Coulometer using Hydranal Coulomat AG oven reagent and nitrogen purge. Weighed solid samples were introduced into a sealed sample vial. Approximately 10 mg of sample was used per titration and duplicate determinations were made. An average of these results is presented unless otherwise stated. Data collection and analysis were performed using Tiamo software.

Results of the KF analysis for the crystalline forms are described in the following table:

| Solid State Form | KF |
|---|---|
| Form 1 | 0.7 wt % water (0.21 mol equiv) |
| Form 2 | 19.1 wt % water (150° C.) (7 mol equiv) |
| Pattern 9 | 1.7 wt %/2.3 wt % water (100° C.) (~0.6 mol equiv) |
| Form 3 | 0.5 wt % water (160° C.) (0.15 mol equiv) |
| amorphous | 3.0 wt % water (0.92 mol equiv) |

Example 22: Ion Chromatography

Data were collected on a Metrohm 930 Compact IC Flex with 858 Professional autosampler and 800 Dosino dosage unit monitor, using IC MagicNet software. Accurately weighed samples were prepared as stock solutions in a suitable solvent. Quantification was achieved by comparison with standard solutions of known concentration of the ion being analyzed. Analyzes were performed in duplicate and an average of the values is given unless otherwise stated.

| IC Method for Cation Chromatography | |
|---|---|
| Parameter | Value |
| Type of method | Cation exchange |
| Column | Metrosep C 4 - 250 (4.0 × 250 mm) |
| Column Temperature (° C.) | Ambient |
| Injection (µL) | Various |
| Detection | Conductivity detector |
| Flow Rate (mL/min) | 0.9 |
| Eluent | 1.7 mM Nitric Acid 0.7 mM Dipicolinic acid in a 5% acetone aqueous solution. |

| IC Method for Anion Chromatography | |
|---|---|
| Parameter | Value |
| Type of method | Anion exchange |
| Column | Metrosep A Supp 5 - 150 (4.0 × 150 mm) |
| Column Temperature (° C.) | Ambient |
| Injection (µL) | Various |
| Detection | Conductivity detector |
| Flow Rate (mL/min) | 0.7 |
| Eluent | 3.2 mM sodium carbonate, 1.0 mM sodium hydrogen carbonate in a 5% acetone aqueous solution. |

Ion chromatography of the crystalline Form 1 of Compound II indicated 1.1 mol equivalents of sodium (adjusted for water), with no other anions or cations present.

Ion chromatography of the crystalline 2-methyltetrahydrofuran solvate Form 3 of Compound II indicated 0.96 mol equivalents of sodium (adjusted for water), with no other anions or cations present.

Ion chromatography of the crystalline tetrahydrofuran solvate Form 4 of Compound II indicated 1.01 mol equivalents of sodium (adjusted for water), with no other anions or cations present.

Example 23: Fourier Transform Infrared (FTIR) Spectroscopy

Data were collected on a Perkin-Elmer Spectrum One fitted with a universal Attenuated Total Reflectance (ATR) sampling accessory from 4000-650 $cm^{-1}$ over 16 scans. The data were collected using Spectrum software and processed using ACD Spectrus Processor.

Characterization of Crystalline Form 1 of Compound II

The Fourier Transform Infrared (FTIR) spectrum for crystalline Form 1 of Compound II is shown in FIG. 4. Characteristic peaks include peaks at 810 $cm^{-1}$, 838 $cm^{-1}$, 1220 $cm^{-1}$, 1504 $cm^{-1}$, and 1612 $cm^{-1}$. Additional characteristic peaks are listed in the following table:

| Wavelength ($cm^{-1}$) | Rel. Intensity* |
|---|---|
| 798 | M |
| 810 | S |
| 838 | S |
| 864 | M |
| 1009 | M |
| 1035 | M |
| 1043 | M |
| 1052 | M |
| 1115 | S |
| 1160 | M |
| 1220 | VS |
| 1236 | M |
| 1333 | M |
| 1413 | M |
| 1425 | M |
| 1504 | S |
| 1612 | VS |

*M = medium; S = strong; VS = very strong

Characterization of Crystalline Acetone Solvate Form 5 of Compound II

The Fourier Transform Infrared (FTIR) spectrum for crystalline acetone solvate Form 5 of Compound II is shown in FIG. 17. Characteristic peaks include peaks at 810 $cm^{-1}$, 838 $cm^{-1}$, 1220 $cm^{-1}$, 1504 $cm^{-1}$, and 1612 $cm^{-1}$. Additional characteristic peaks are listed in the following table:

| Wavelength ($cm^{-1}$) | Rel. Intensity* |
|---|---|
| 798 | M |
| 810 | S |
| 838 | S |
| 864 | M |
| 1009 | M |
| 1042 | M |
| 1053 | M |
| 1116 | M |
| 1160 | M |
| 1220 | VS |
| 1236 | M |
| 1333 | M |
| 1412 | M |
| 1424 | M |
| 1504 | S |
| 1612 | VS |

*M = medium; S = strong; VS = very strong

Example 24: Raman Spectroscopy

Data were collected on a Renishaw inVia Qontor. Instrument control, data analysis and presentation software was WiRE.

Method: excitation source, $\lambda_{ex}$=785 nm laser, attenuated appropriately to avoid sample degradation Raman shift range: 100-3200 cm-1

Exposure time: 10 s

Accumulations: 1

Characterization of Crystalline Form 1 of Compound H

The Raman spectrum for crystalline Form 1 of Compound II is shown in FIG. 5. Characteristic peaks are listed in the following table:

| Wavelength (cm$^{-1}$) | Rel. Intensity* |
|---|---|
| 103 | M |
| 126 | M |
| 810 | M |
| 1158 | M |
| 1238 | M |
| 1604 | VS |
| 1629 | M |

*M = medium; S = strong; VS = very strong

Example 25: Single Crystal X-Ray Diffraction (SCXRD)

Preparation of Single Crystal

A crystal of Compound II (Form 1) was isolated from an aggregate of crystals obtained by evaporation from an EtOAc/H$_2$O (99:1 v/v %) solution. The approximate dimensions of the crystal were: 0.40×0.03×0.005 mm.

Collection and Characterization

Data were collected on a Rigaku Oxford Diffraction Supernova Dual Source, Cu at Zero, Atlas CCD diffractometer equipped with an Oxford Cryosystems Cobra cooling device. The data were collected using Cu Kα, radiation ($\lambda$=1.5418 Å) at a constant temperature with ω variable scan technique (2.807 to 50.989° θ). Additional collection and refinement parameters are outlined in Table 1, below.

Structures were solved and refined using the Bruker AXS SHELXTL suite or the OLEX$^2$ crystallographic software. Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter. A reference diffractogram for the crystal structure was generated in Mercury.

TABLE 1

Data collection and structure refinement for Compound II (Form 1)

| | |
|---|---|
| Diffractometer | SuperNova, Dual, Cu at zero, Atlas |
| Radiation source | SuperNova (Cu) X-ray Source, CuKα |
| Data collection method | omega scans |
| Theta range for data collection | 2.807 to 50.989° |
| Index ranges | $-31 \le h \le 31, -6 \le k \le 5, -27 \le l \le 27$ |
| Reflections collected | 28094 |
| Independent reflections | 5555 [R(int) = 0.1913] |
| Coverage of independent reflections | 58.4 % |
| Variation in check reflections | n/a |
| Absorption correction | Multi-scan |
| Max. and min. transmission | 1.00000 and 0.42918 |
| Structure solution technique | Direct Methods |
| Structure solution program | SHELXTL (Sheldrick, 2013) |
| Refinement technique | Full-matrix least-squares on F$^2$ |
| Refinement program | SHELXL-2014/6 (Sheldrick, 2014) |
| Function minimised | $\Sigma$ w $(F_o^2 - F_c^2)^2$ |
| Data/restraints/parameters | 5555/0/705 |
| Goodness-of-fit on F$^2$ | 1.007 |
| $\Delta/\sigma_{max}$ | 0.000 |
| Final R indices: | |
| 2657 data; I > 2σ(I) | R1 = 0.0945, wR2 = 0.2099 |
| all data | R1 = 0.1886, wR2 = 0.2771 |
| Weighting scheme | w = $1/[\sigma^2(F_o^2) + 0.1224P)^2$]where P = $(F_o^2 + 2F_c^2)/3$ |
| Extinction coefficient | n/a |
| Largest diff. peak and hole | 0.426 and -0.390 eÅ$^{-3}$ |
| Refinement summary: | |
| Ordered Non-H atoms, XYZ | Freely refining |
| Ordered Non-H atoms, U | Anisotropic |
| H atoms (on carbon), XYZ | Idealized positions riding on attached atoms |
| H atoms (on carbon), U | Appropriate multiple of U(eq) for bonded atom |
| H atoms (on heteroatoms), XYZ | Freely refined |
| H atoms (on heteroatoms), U | Isotropic |
| Disordered atoms, OCC | No Disorder |
| Disordered atoms, XYZ | No Disorder |
| Disordered atoms, U | No Disorder |

The crystal structure of Compound II (Form 1) was determined at 100 K and a summary of the structural data can be found in Tables 2, 3, and 4. The X-ray data were collected up to 1.0 Å resolution, using exposures of 100 seconds per frame at the low θ-angle and 200 seconds per frame at the higher θ-angle. At certain crystal orientations, the diffraction pattern shows split and streaky reflections which reflects the overall crystal quality and could indicate potential twinning.

The crystals are monoclinic, space group P2/c and refined with a final R1 [I>2σ(I)] value of 9.45%. Platon ADDSYM analysis was performed and no additional space group was found. Moreover, the structure solution was also attempted in the more common P2$_1$/c space group, however, no satisfactory structure solution was found. Despite only low resolution data being collected for this crystal structure, the data was sufficient to successfully determine the crystal structure of Compound II (Form 1) in P2/c space group and confirm the atomic connectivity which is consistent with the molecular 2D representation. The asymmetric unit contains two fully ordered Compound I anions and two independent Na$^+$ cations.

TABLE 2

Crystal Data of Compound II (Form 1) at 100 K

| | |
|---|---|
| Crystal System | Monoclinic |
| Space Group | P2/c |
| a (Å) | 31.581(3) |
| b (Å) | 6.1180(4) |
| c (Å) | 27.2046(18) |
| α | 90° |
| β | 94.447(7)° |
| γ | 90° |
| V (Å$^3$) | 5240.4(7) |
| Z | 8 |
| Calculated Density (Mg/m$^3$) | 1.363 |
| Absorption coefficient (mm$^{-1}$) | 0.937 |
| F(000) | 2256 |

TABLE 3

Fractional Atomic Coordinates for Compound II (Form 1) at 100 K

| | x/a | y/b | z/c |
|---|---|---|---|
| Na1A | 0.55177(12) | 0.7521(5) | 0.27685(13) |
| F1A | 0.11468(18) | 0.1067(9) | 0.5137(2) |
| O1A | 0.5084(2) | 1.6234(10) | 0.3364(2) |
| O2A | 0.4711(2) | 1.9101(10) | 0.3072(2) |
| O3A | 0.4420(2) | 1.4498(10) | 0.3786(2) |
| O4A | 0.3042(2) | 0.9658(10) | 0.4278(2) |
| O5A | −0.0492(2) | 0.8045(12) | 0.1069(3) |
| N1A | 0.0218(3) | 1.0358(13) | 0.1493(3) |
| C1A | 0.4750(3) | 1.7319(17) | 0.3316(3) |
| C2A | 0.4347(3) | 1.6488(15) | 0.3518(3) |
| C3A | 0.4054(3) | 1.3482(16) | 0.3910(3) |
| C4A | 0.3645(3) | 1.4107(15) | 0.3761(3) |
| C5A | 0.3295(3) | 1.2894(15) | 0.3868(3) |
| C6A | 0.3358(3) | 1.0998(17) | 0.4152(3) |
| C7A | 0.3763(3) | 1.0428(14) | 0.4321(3) |
| C8A | 0.4120(3) | 1.1565(16) | 0.4210(3) |
| C9A | 0.4557(3) | 1.0922(15) | 0.4400(3) |
| C10A | 0.2618(3) | 1.0346(15) | 0.4183(4) |
| C11A | 0.2352(3) | 0.8655(16) | 0.4405(3) |
| C12A | 0.1986(3) | 0.7796(15) | 0.4212(3) |
| C13A | 0.1766(3) | 0.6035(14) | 0.4464(3) |
| C14A | 0.1990(3) | 0.4644(16) | 0.4787(3) |
| C15A | 0.1781(3) | 0.2962(16) | 0.5027(3) |
| C16A | 0.1358(4) | 0.2724(16) | 0.4913(3) |
| C17A | 0.1116(3) | 0.4139(16) | 0.4608(3) |
| C18A | 0.1326(4) | 0.5764(16) | 0.4386(4) |
| C19A | 0.1763(3) | 0.8646(16) | 0.3748(3) |
| C20A | 0.1673(3) | 0.7262(15) | 0.3345(4) |
| C21A | 0.1426(3) | 0.7969(16) | 0.2942(4) |
| C22A | 0.1250(3) | 1.0087(18) | 0.2925(4) |
| C23A | 0.1354(3) | 1.1487(16) | 0.3320(4) |
| C24A | 0.1600(3) | 1.0762(16) | 0.3715(4) |
| C25A | 0.0966(4) | 1.0763(16) | 0.2511(4) |
| C26A | 0.0724(3) | 1.1350(17) | 0.2182(4) |
| C27A | 0.0403(3) | 1.2154(16) | 0.1803(4) |
| C28A | −0.0023(3) | 0.8873(15) | 0.1787(4) |
| C29A | −0.0221(4) | 0.7113(16) | 0.1459(4) |
| C30A | −0.0269(4) | 0.9488(18) | 0.0779(4) |
| C31A | −0.0076(3) | 1.1299(15) | 0.1108(4) |
| Na1B | 0.50100(12) | 1.2565(5) | 0.32498(12) |
| F1B | 0.94656(18) | 0.5969(8) | 0.4452(2) |
| O1B | 0.5610(2) | 1.1172(9) | 0.2949(2) |
| O2B | 0.5623(2) | 1.3963(11) | 0.2415(2) |
| O3B | 0.6224(2) | 0.9057(10) | 0.2598(2) |
| O4B | 0.7554(2) | 0.3890(10) | 0.2088(2) |
| O5B | 0.5490(2) | −0.7247(10) | 0.4023(2) |
| N1B | 0.6179(3) | −0.6391(12) | 0.4735(3) |
| C1B | 0.5754(4) | 1.2146(19) | 0.2598(4) |
| C2B | 0.6129(3) | 1.1120(15) | 0.2360(4) |
| C3B | 0.6584(3) | 0.7925(15) | 0.2471(3) |
| C4B | 0.6805(3) | 0.8379(16) | 0.2073(4) |
| C5B | 0.7135(3) | 0.7053(15) | 0.1952(3) |
| C6B | 0.7243(3) | 0.5240(16) | 0.2248(4) |
| C7B | 0.7029(3) | 0.4838(14) | 0.2653(3) |
| C8B | 0.6697(3) | 0.6152(15) | 0.2783(3) |
| C9B | 0.6461(3) | 0.5722(13) | 0.3234(3) |
| C10B | 0.7719(3) | 0.2156(14) | 0.2414(3) |
| C11B | 0.8036(3) | 0.2993(14) | 0.2795(4) |
| C12B | 0.8085(3) | 0.2600(14) | 0.3285(3) |
| C13B | 0.8438(3) | 0.3582(15) | 0.3596(3) |
| C14B | 0.8624(3) | 0.2370(14) | 0.3989(3) |
| C15B | 0.8962(3) | 0.3143(16) | 0.4279(4) |
| C16B | 0.9127(3) | 0.5176(18) | 0.4166(4) |
| C17B | 0.8953(3) | 0.6460(15) | 0.3782(4) |
| C18B | 0.8614(3) | 0.5608(16) | 0.3505(4) |
| C19B | 0.7785(3) | 0.1160(17) | 0.3530(4) |
| C20B | 0.7610(3) | 0.1914(15) | 0.3965(4) |
| C21B | 0.7357(3) | 0.0582(15) | 0.4221(3) |
| C22B | 0.7278(3) | −0.1574(16) | 0.4069(4) |
| C23B | 0.7446(3) | −0.2323(15) | 0.3643(3) |
| C24B | 0.7692(3) | −0.0950(15) | 0.3375(3) |
| C25B | 0.7035(3) | −0.3033(16) | 0.4361(3) |
| C26B | 0.6837(3) | −0.4190(15) | 0.4608(3) |
| C27B | 0.6583(3) | −0.5563(14) | 0.4930(3) |
| C28B | 0.5892(3) | −0.4684(15) | 0.4538(3) |
| C29B | 0.5462(3) | −0.5614(16) | 0.4400(3) |
| C30B | 0.5779(3) | −0.8945(15) | 0.4192(4) |
| C31B | 0.6209(3) | −0.8071(14) | 0.4349(3) |

TABLE 4

Hydrogen Atom Coordinates for Compound II (Form 1) at 100 K

| | x/a | y/b | z/c |
|---|---|---|---|
| H2AA | 0.4236 | 1.7608 | 0.3738 |
| H2AB | 0.4129 | 1.6239 | 0.3242 |
| H4A | 0.3602 | 1.5421 | 0.3577 |
| H5A | 0.3017 | 1.3339 | 0.3751 |
| H | 0.3799 | 0.9176 | 0.4526 |
| H9AA | 0.467 | 1.2009 | 0.464 |
| H9AB | 0.474 | 1.0846 | 0.4125 |
| HA | 0.4548 | 0.9488 | 0.4559 |
| H10A | 0.2543 | 1.0456 | 0.3823 |
| H10B | 0.2574 | 1.1792 | 0.4334 |
| H11A | 0.2453 | 0.8126 | 0.4721 |
| H14A | 0.2288 | 0.482 | 0.4848 |
| H15A | 0.1931 | 0.2031 | 0.526 |
| H17A | 0.0817 | 0.398 | 0.4556 |
| H18A | 0.1169 | 0.6743 | 0.4171 |
| H20A | 0.1785 | 0.5819 | 0.3351 |
| H21A | 0.1372 | 0.7016 | 0.2668 |
| H23A | 0.1251 | 1.2947 | 0.3312 |
| H24A | 0.1664 | 1.1738 | 0.3982 |
| H27A | 0.0535 | 1.3232 | 0.1592 |
| H27B | 0.0174 | 1.2905 | 0.1966 |
| H28A | −0.0248 | 0.9694 | 0.1943 |
| HB | 0.0168 | 0.8208 | 0.2052 |
| HC | 0.0005 | 0.6246 | 0.1319 |
| H29B | −0.0388 | 0.6118 | 0.1656 |
| H30A | −0.0465 | 1.0122 | 0.0515 |
| H30B | −0.0042 | 0.8691 | 0.0622 |
| H31A | 0.0077 | 1.2344 | 0.0908 |
| H31B | −0.0305 | 1.2103 | 0.126 |
| H2BA | 0.6055 | 1.0894 | 0.2003 |
| H2BB | 0.6379 | 1.2097 | 0.24 |
| H4B | 0.6731 | 0.9624 | 0.1875 |
| H5B | 0.7286 | 0.7368 | 0.1672 |
| H7B | 0.711 | 0.3617 | 0.2855 |
| H9BA | 0.6446 | 0.7071 | 0.3426 |
| H9BB | 0.661 | 0.4595 | 0.3436 |
| H9BC | 0.6172 | 0.522 | 0.3133 |
| H10C | 0.7851 | 0.1016 | 0.2218 |
| H10D | 0.7481 | 0.1474 | 0.2576 |
| H11B | 0.824 | 0.3966 | 0.2677 |
| H14B | 0.8512 | 0.097 | 0.4057 |
| H15B | 0.9083 | 0.2316 | 0.455 |
| H17B | 0.9064 | 0.7862 | 0.3715 |
| H18B | 0.8491 | 0.6445 | 0.3236 |
| H20B | 0.7669 | 0.3358 | 0.4079 |
| H21B | 0.7235 | 0.1126 | 0.4505 |
| H23B | 0.7393 | −0.378 | 0.3535 |
| H24B | 0.7798 | −0.147 | 0.3079 |
| H27C | 0.6761 | −0.6831 | 0.5041 |
| H27D | 0.6535 | −0.4694 | 0.5228 |
| H28C | 0.6006 | −0.4018 | 0.4244 |
| H28D | 0.5869 | −0.3525 | 0.4788 |
| H29C | 0.5347 | −0.6278 | 0.4693 |
| H29D | 0.5267 | −0.4435 | 0.4277 |
| H30C | 0.5803 | −1.0023 | 0.3924 |
| H30D | 0.5664 | −0.9711 | 0.4473 |
| H31C | 0.6395 | −0.9277 | 0.4478 |
| H31D | 0.6337 | −0.7425 | 0.4062 |

Figure 26:
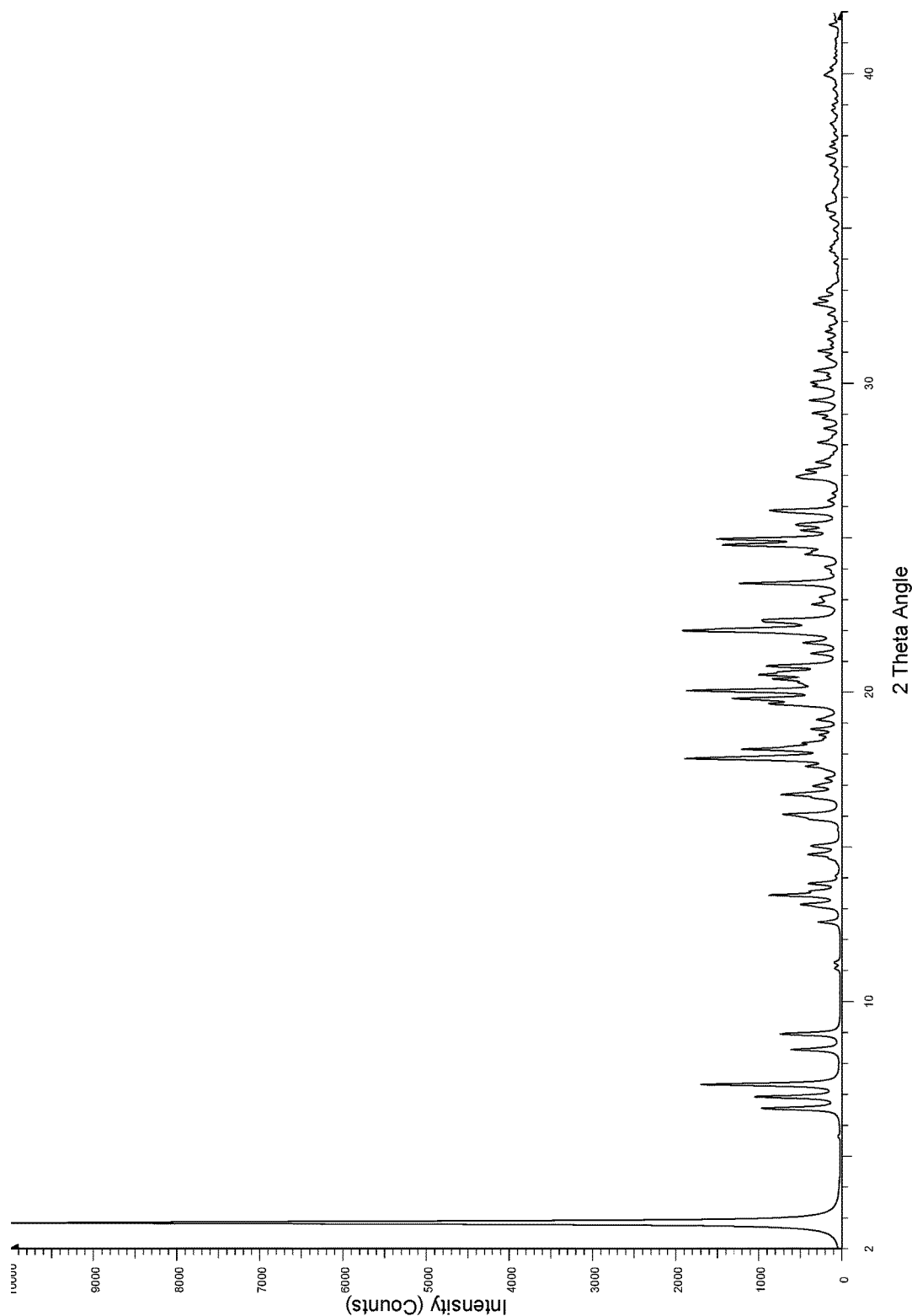
FIG. 26 illustrates a simulated XRPD pattern for Form 1 of Compound II.

The simulated XRPD pattern of Compound 11 (Form 1) at 100 K is shown in FIG. 26.

Figure 27:
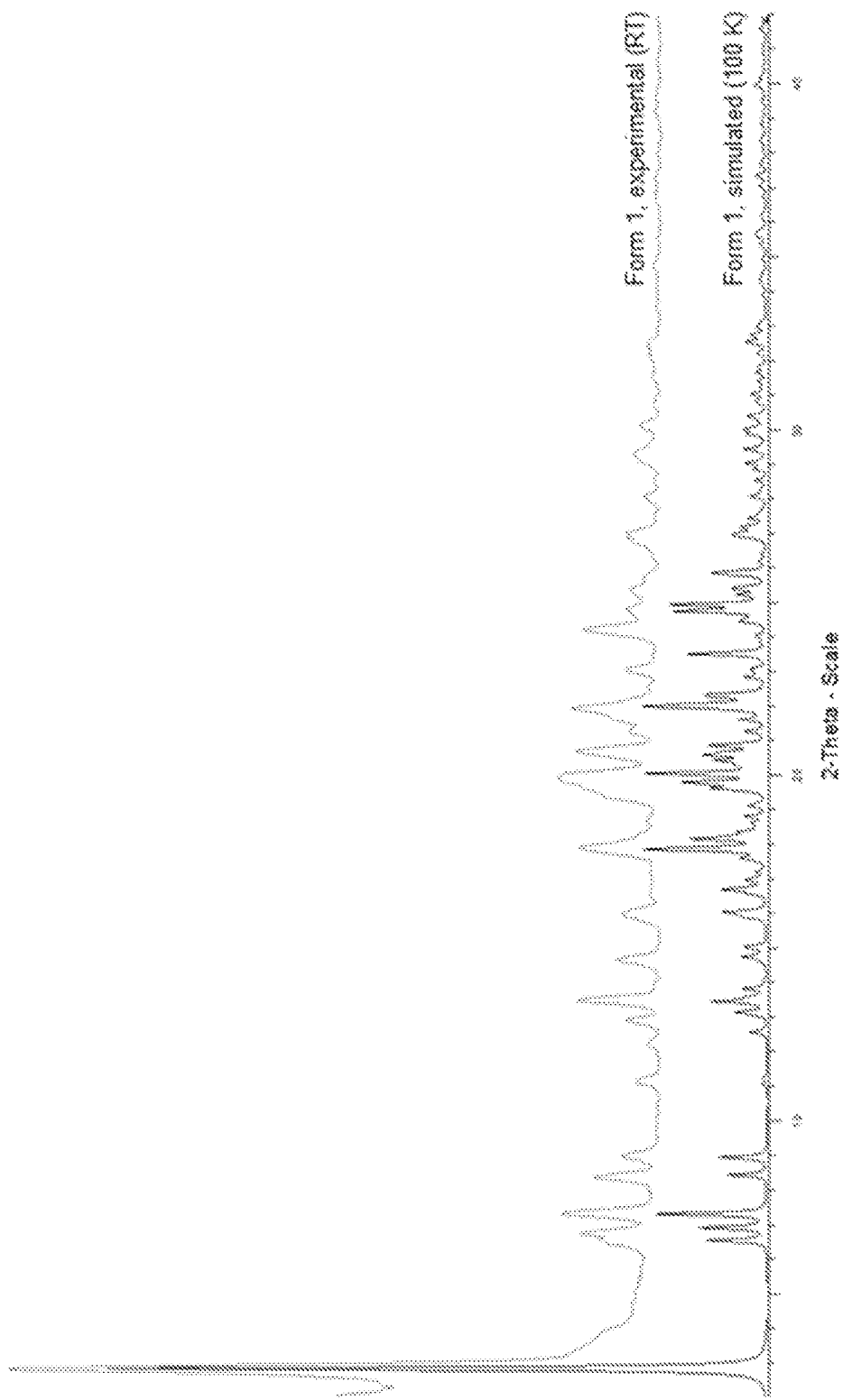
FIG. 27 illustrates the overlap of the simulated and experimental XRPD patterns for Form 1 of Compound II.

An overlay with the experimental diffractogram at RT confirms that the simulated diffractogram from the single crystal structure is consistent with the experimental Compound II (Form 1) diffractogram (FIG. 27).

Example A-1: Parenteral Pharmaceutical Composition

To prepare a parenteral pharmaceutical composition suitable for administration by injection (subcutaneous, intravenous), 1-100 mg of a water-soluble salt of a compound Formula (I), or a pharmaceutically acceptable salt or solvate thereof, is dissolved in sterile water and then mixed with 10 mL of 0.9% sterile saline. A suitable buffer is optionally added as well as optional acid or base to adjust the pH. The mixture is incorporated into a dosage unit form suitable for administration by injection

Example A-2: Oral Solution

To prepare a pharmaceutical composition for oral delivery, a sufficient amount of a compound disclosed herein, or a pharmaceutically acceptable salt thereof, is added to water (with optional solubilizer(s), optional buffer(s) and taste masking excipients) to provide a 20 mg/mL solution.

Example A-3: Oral Tablet

A tablet is prepared by mixing 20-50% by weight of a compound disclosed herein, or a pharmaceutically acceptable salt thereof, 20-50% by weight of microcrystalline cellulose, 1-10% by weight of low-substituted hydroxypropyl cellulose, and 1-10% by weight of magnesium stearate or other appropriate excipients. Tablets are prepared by direct compression. The total weight of the compressed tablets is maintained at 100-500 mg.

Example A-4: Oral Capsule

To prepare a pharmaceutical composition for oral delivery, 10-500 mg of a compound disclosed herein, or a pharmaceutically acceptable salt thereof, is optionally mixed with starch or other suitable powder blends. The mixture is incorporated into an oral dosage unit such as a hard gelatin capsule, which is suitable for oral administration.

In another embodiment, 10-500 mg of a compound disclosed herein, or a pharmaceutically acceptable salt thereof, is placed into Size 4 capsule, or size 1 capsule (hypromellose or hard gelatin) and the capsule is closed.

The examples and embodiments described herein are for illustrative purposes only and various modifications or changes suggested to persons skilled in the art are to be included within the spirit and purview of this application and scope of the appended claims.

What is claimed is:

1. Crystalline sodium (E)-2-(4-((3-(4-fluorophenyl)-3-(4-(3-morpholinoprop-1-yn-1-yl)phenyl)allyl)oxy)-2-methylphenoxy)acetate (Compound II), wherein crystalline Compound II is crystalline Form 1, characterized as having:
   (a) an X-ray powder diffraction (XRPD) pattern as shown in FIG. 1;
   (b) an XRPD pattern with peaks at about 2.8° 2-Theta, about 7.2° 2-Theta, about 13.4° 2-Theta, about 17.8° 2-Theta, about 19.7° 2-Theta, about 19.9° 2-Theta, and about 20.6° 2-Theta as measured using Cu Kα radiation;
   (c) a differential scanning calorimetry (DSC) thermogram as shown in FIG. 2;
   (d) a DSC thermogram with an endotherm having onset at about 179.5° C. and peak at about 181.6° C.;
   (e) a Thermogravimetric Analysis (TGA) pattern as shown in FIG. 3;
   (f) a TGA pattern with a 0.1% w/w loss from 25 to 60° C. and degradation onset at about 250° C.;
   (g) a Fourier transform infrared (FTIR) spectroscopy pattern as shown in FIG. 4;
   (h) an FTIR spectroscopy pattern with peaks at about 103 $cm^{-1}$, about 838 $cm^{-1}$, about 1220 $cm^{-1}$, about 1504 $cm^{-1}$, and about 1612 $cm^{-1}$;
   (i) a Raman spectroscopy pattern as shown in FIG. 5;
   (j) a Raman spectroscopy pattern with peaks at about 103 $cm^{-1}$, about 126 $cm^{-1}$, about 810 $cm^{-1}$, about 1158 $cm^{-1}$, about 1238 $cm^{-1}$, about 1604 $cm^{-1}$, and about 1629 $cm^{-1}$;
   (k) unit cell parameters equal to the following at 100 K:

| Crystal System | Monoclinic |
|---|---|
| Space Group | P2/c |
| a (Å) | 31.581(3) |
| b (Å) | 6.1180(4) |
| c (Å) | 27.2046(18) |
| α° | 90 |
| β° | 94.447(7) |
| γ° | 90 |
| V (Å$^3$) | 5240.4(7) |
| Z | 8 |
| Calculated Density (Mg/m$^3$) | 1.363 |
| Absorption coefficient (mm$^{-1}$) | 0.937 |
| F(000) | 2256 | or
   (l) combinations thereof.

2. Crystalline Form 1 of sodium (E)-2-(4-((3-(4-fluorophenyl)-3-(4-(3-morpholinoprop-1-yn-1-yl)phenyl)allyl)oxy)-2-methylphenoxy)acetate (Compound II) characterized as having:
   an X-ray powder diffraction (XRPD) pattern as shown in FIG. 1.

3. Crystalline Form 1 of sodium (E)-2-(4-((3-(4-fluorophenyl)-3-(4-(3-morpholinoprop-1-yn-1-yl)phenyl)allyl)oxy)-2-methylphenoxy)acetate (Compound II) characterized as having:
   an X-ray powder diffraction (XRPD) pattern with peaks at about 2.8° 2-Theta, about 7.2° 2-Theta, about 13.4° 2-Theta, about 17.8° 2-Theta, about 19.7° 2-Theta, about 19.9° 2-Theta, and about 20.6° 2-Theta as measured using Cu Kα radiation.

4. The crystalline Compound II of claim 1, characterized as having:
   an XRPD pattern as shown in FIG. 1; or
   an XRPD pattern with peaks at about 2.80° 2-Theta, about 7.2° 2-Theta, about 13.4° 2-Theta, about 17.8° 2-Theta, about 19.7° 2-Theta, about 19.9° 2-Theta, and about 20.6° 2-Theta as measured using Cu Kα radiation.

5. The crystalline Compound II of claim 1, characterized as having:
   a DSC thermogram as shown in FIG. 2; or
   a DSC thermogram with an endotherm having onset at about 179.5° C. and peak at about 181.6° C.

6. The crystalline Compound II of claim 1, characterized as having:

a TGA pattern as shown in FIG. 3; or a TGA pattern with a 0.1% w/w loss from 25 to 60° C. and degradation onset at about 250° C.

7. The crystalline Compound II of claim 1, is characterized as having:

an FTIR spectroscopy pattern as shown in FIG. 4; or an FTIR spectroscopy pattern with peaks at about 103 cm$^{-1}$, about 838 cm$^{-1}$, about 1220 cm$^{-1}$, about 1504 cm$^{-1}$, and about 1612 cm$^{-1}$.

8. The crystalline Compound II of claim 1, characterized as having:

a Raman spectroscopy pattern as shown in FIG. 5; or a Raman spectroscopy pattern with peaks at about 103 cm$^{-1}$, about 126 cm$^{-1}$, about 810 cm$^{-1}$, about 1158 cm$^{-1}$, about 1238 cm$^{-1}$, about 1604 cm$^{-1}$, and about 1629 cm$^{-1}$.

9. The crystalline Compound II of claim 1, characterized as having: unit cell parameters equal to the following at 100 K:

| Crystal System | Monoclinic |
|---|---|
| Space Group | P2/c |
| a (Å) | 31.581(3) |
| b (Å) | 6.1180(4) |
| c (Å) | 27.2046(18) |
| 60 +20 | 90 |
| β° | 94.447(7) |
| γ° | 90 |
| V (Å$^3$) | 5240.4(7) |
| Z | 8 |
| Calculated Density (Mg/m$^3$) | 1.363 |
| Absorption coefficient (mm$^{-1}$) | 0.937 |
| F(000) | 2256 |

10. The crystalline Compound II of claim 1, wherein crystalline Compound II is unsolvated.

11. The crystalline Compound II of claim 1, wherein crystalline Compound II is at least about 95% pure.

12. A pharmaceutical composition comprising the crystalline Compound II of claim 1 and at least one pharmaceutically acceptable excipient.

13. The pharmaceutical composition of claim 12, wherein the pharmaceutical composition is formulated for administration to a mammal by oral administration.

14. The pharmaceutical composition of claim 13, wherein the pharmaceutical composition is in the form of a solid form pharmaceutical composition.

15. The pharmaceutical composition of claim 14, wherein the pharmaceutical composition is in the form of a tablet, a pill, or a capsule.

16. The pharmaceutical composition of claim 12, comprising about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, and about 400 mg of crystalline Compound II.

\* \* \* \* \*